US009738941B2

(12) United States Patent
Poetter et al.

(10) Patent No.: US 9,738,941 B2
(45) Date of Patent: Aug. 22, 2017

(54) COMPOSITIONS AND METHODS OF DETECTING RESPIRATORY PATHOGENS USING NUCLEIC ACID PROBES AND SUBSETS OF BEADS

(71) Applicant: GENERA BIOSYSTEMS LIMITED, Victoria (AU)

(72) Inventors: Karl Frederick Poetter, Victoria (AU); Nick Vandegraaff, Victoria (AU)

(73) Assignee: Genera Biosystems Limited, Victoria (AU)

( * ) Notice: Subject to any disclaimer, the term of this patent is extended or adjusted under 35 U.S.C. 154(b) by 37 days.

(21) Appl. No.: 14/349,256

(22) PCT Filed: Oct. 4, 2012

(86) PCT No.: PCT/AU2012/001208

§ 371 (c)(1),
(2) Date: Apr. 2, 2014

(87) PCT Pub. No.: WO2013/049891

PCT Pub. Date: Apr. 11, 2013

(65) Prior Publication Data

US 2014/0309138 A1 Oct. 16, 2014

(30) Foreign Application Priority Data

Oct. 4, 2011 (AU) ................................ 2011904105

(51) Int. Cl.

| | |
|---|---|
| ***C12P 19/34*** | (2006.01) |
| ***C12Q 1/70*** | (2006.01) |
| ***C12Q 1/68*** | (2006.01) |

(52) U.S. Cl.

CPC ............. *C12Q 1/701* (2013.01); *C12Q 1/686* (2013.01); *C12Q 1/689* (2013.01); *C12Q 1/6895* (2013.01); *C12Q 1/70* (2013.01); *C12Q 2600/16* (2013.01)

(58) Field of Classification Search

USPC ................................................ 435/6.12, 91.2

See application file for complete search history.

(56) References Cited

U.S. PATENT DOCUMENTS

| | | | | |
|---|---|---|---|---|
| 7,972,786 | B2 | 7/2011 | Hartshorn et al. | |
| 2007/0092871 | A1 | 4/2007 | Lodes et al. | |
| 2009/0305229 | A1 * | 12/2009 | McBride ................ | C12Q 1/701 435/5 |
| 2010/0086908 | A1 | 4/2010 | Prudent et al. | |
| 2010/0279273 | A1 * | 11/2010 | Bergeron ................ | C40B 40/06 435/5 |
| 2010/0297630 | A1 * | 11/2010 | Reijans ................ | C12Q 1/6818 435/6.1 |
| 2011/0046001 | A1 * | 2/2011 | Corbeil .................. | C12Q 1/701 506/9 |

FOREIGN PATENT DOCUMENTS

| | | | |
|---|---|---|---|
| WO | WO 2006/060872 | A1 | 6/2006 |
| WO | WO 2007/068904 | A1 | 6/2007 |
| WO | WO 2008/042450 | A2 | 4/2008 |
| WO | WO 2008/124091 | A2 | 10/2008 |
| WO | WO 2009/102369 | A2 | 8/2009 |

* cited by examiner

*Primary Examiner* — Kenneth Horlick
(74) *Attorney, Agent, or Firm* — Knobbe Martens Olson & Bear LLP

(57) ABSTRACT

Methods for screening a multiplicity of respiratory pathogens by isolating nucleic acids from a sample include isolating a nucleic acid from a sample and using solid phase amplification with forward primers SEQ ID NOs: 1 to 16 or 33 or 35 and corresponding reverse primers SEQ ID NOs: 17 to 32 or 34 or 36 along with probes to generate amplicons. The method further includes employing bead sets which are homogenous with respect to bead size and optionally with respect to the intensity of the label. Binding of a particular amplicon to a subset of beads determines the identity of the respiratory pathogen.

15 Claims, 10 Drawing Sheets

*Control Construct Insert Sequences*

MS2P (RTI-C1)

taatacgactcactatagggagaaattaaccctcactaaagggagagtttcggcttctccctcgacgcacgctcctgctacagcctct
tccctgtaagccaaaacttgacttacatcgaagtgccgcagaacgttgcgaaccgggcgtcgaccgaagtcctgcaaaaggtcac
ccagggtaattttaaccttggtgttgctttagcagaggccaggtcgacagcctcacaactcgcgacgcaaaccattgcgctcgtgaa
ggcgtacactgccgctcgtcgcggtaattggcgccaggcgctccgctaccttgccctaaacgaagatcgaaagtttcgatcaaaac
acgtggccggcaggtggttggagttgcagttcggttggttaccactaatgagtgcggccgc (SEQ ID NO: 55)

InA (RTI-C2)

taatacgactcactatagggagaaattaaccctcactaaagggagactttggccccatggaatgttatctcccttttaagcttcctatac
agtttaactgctctgtccatgttatttggatccccattcccatttagggcattttggacaaagcgtctacgctgcagtcctcgctcactgg
gcacggtgagcgtgaacacaaatcctaaaatccccttagtcagaggtgacaggattggtcttgtctttagccattccatgagagcctc
aagatctgtgttcttccctgcaaagacatcttcaagtctctgcgcgatctcggctttgagggggcctgacgggacgatagagagaac
gtacgtttcgacctcggttagaagactcatctttcaatatctagcggccgc (SEQ ID NO:56)

InB (RTI-C3)

taatacgactcactatagggagaaattaaccctcactaaagggagacttctaagaaaccagcaatagctccgaagaaacccctttcc
tttaatagttttgcaggaggtctatatttggttccattggcaagcttcaaaggtgttttcacccatattgggcaatttcctatggcttttgcat
gttctcctgtgtagtaaggcttgcttttgtttaatccaccgtattttcgtgaaggcaatctgcttaatttggtcttctccttctgtacaaatgt
atggtacttctactgttagtggattcgttgctgttttgttgttgtcgttctttgggacagcccaagccattgttgcgaaaaatccgtttctac
tggtaacgttagggcaagatcctgaggttccaagtctgtagggtcctcctggtgccttttctgcattgataacgttagcggccgc
(SEQ ID NO:57)

H1 (RTI-C4)

taatacgactcactatagggagaaattaaccctcactaaagggagatttatcattaatgtaggatttgctgagctttgggtatgaatttc
ctttttaactagccatattaaatttttgtagaagctttttgctccagcatgaggacatgctgccgttacacctttgttcgagtcatgattgg
gccatgaacttgtcttggggaatatctcaaacctttcaaatgatgacactgagctcaattgctctcttagctcctcataatcgatgaaatc
tcctgggtaacacgttccattgtctgaactagatgtttccacaatgtaggaccatgagcttgctgtggagagtgattcacactctggatt
tcccaggatccagccagcaatgttacatttacccaaatgcaatggggctacccctcttagtttgcatagtttcccgttatgcttgtcttct
agaaggttaacagagtgtgttactgttacattcttttctagtactgtgtctgcggccgc (SEQ ID NO:58)

H5 (RTI-C5)

taatacgactcactatagggagaaattaaccctcactaaagggagacacaaatttaaatgcaaattctgcattgtaacgatccattgg
agcacatccataaagatagaccagccaccatgattgccagtgctagggaactcgccactgttgaataaattgacagtatttggtaag
ttcctattgattccaattttatttcagttcttcatagtcgttgaaattccctgggtaacagaggtcattggctggattggccttctccactat
gtaagaccattccggcacattgatgaattcgtcacacattgggtttccgaggagccatccagctacactacaatctcttaaaattaga
ggcttcactccatctagatcgcagagcttcccgttgtgtgtctgcggccgc (SEQ ID NO:59)

Figure 1A

RSVA (RTI-C6) – OBSOLETE (see RTI-C18)

taatacgactcactatagggagaaattaaccctcactaaagggagatagaaaatgtctttatgattccacgatttttattggatgctgta catttagttttgccatagcatgacacaatggctcctagagatgtgataacggagctgcttacatctgtttttgaagtcataattttgcaatc atatgtgtacctctgtattctcccattatgcctaggccagcagcattgcctaatactacactggagaagtgaggaaattgagtcaaaga caataatgatgcttttgggttgttcaatatatggtagaaccctgcttctccacccaatttttgggcatattcatatgctccgttggatggtg tatttgctggatgacagaagttgatctttgttgagtgtatcattcaacttgactttgctaagagccatttttgtatttgccccatctttcatctt atgtctctccttaatttaaattactataattttcaggctccatttgaactatggagtgtggtgcggccgc (SEQ ID NO:60)

RSVB (RTI-C7) – OBSOLETE (see RTI-C19)

taatacgactcactatagggagaaattaaccctcactaaagggagaataatcccacgattttgttggatgcagtgcatttagttttacc atagcatgacactatagctccaagagaagtaattactgagctgcttatgtctgtttttgatgtcatatactctcccattatgcctagacctg ctgcattgcctaggaccacacttgagaagttaggaaattgagttaatgacagcaatgatgcttttggattgttcaatatatggtagaatc cagcttctcctcccaacttctgtgcatactcataattgggagtgtcaatattatctcctgtactacgttgaatagtgtatttgctggatgac agcagctgatccttatttaatgtatcatttaacttgactttgctaagagccatctttgtatttgccccaatttatgttattggctttacttttattt ttaattactaaaacggattagctccttcttaactattgagcattgttgtttgaggaatagcttggtttggttgggttggttttttttgttggaat gcggccgc (SEQ ID NO:61)

Para1 (RTI-C8)

taatacgactcactatagggagaaattaaccctcactaaagggagattgaaccagttgcagtctgggtttcctggtcgcgacaggac tttatgaggcgcccaattaatggtcatggggttgttgatatctaatgatcctatttgcaggttggagtgccaacctgaaccccttgttcct gcagctattacagaacatgatttcctgttgtcgttgatgtcataggtatgagaaattaccgggtttaaatcaggatacatatctgaattta aggatatgtaacctaattgtaaaacctgatatgacttccctatatctgcacatccttgagtgattaagtttgatgaatacgcatatattgca tcaccaattgataatgaaggtagtctaacacatcctgaaattgtggtggatccagaaagtagacttggtccaggtaataatgagagc ggccgc (SEQ ID NO:62)

Para2 (RTI-C9)

taatacgactcactatagggagaaattaaccctcactaaagggagacattaagcggccacacatctgcgtacacccctgtgatgca attagcagggcaaaaacttgttgcattgcatggcatgactccaggacgaggaacttgataggacggtacccattgagcctcaatgat cggagctgcaggattgattgtggcccactgccctgttgtatttggaagagatatgactctttcaataaaggtatcattataataatagaa agcaagtctcagttcagctagatcagtcgtggcataatcttctttttcagaccttgtagctacatagcaatacaagacacaacctcctg gtatagcagtgactgaacagcttttgcgattgattccatcacttaggtaaatggttttcatagtcctgcggccgc (SEQ ID NO: 63)

Para3 (RTI-C10)

taatacgactcactatagggagaaattaaccctcactaaagggagatggacatgaatgtccccatggacattcattgtttcctggtctt gatagcacattatgccatgtccattttatccttatatcactgtagtcagtaatgtcaattattcctaattgtaacttgctgtgccaacttgtag atcttgtatatataaagtatgagagatcctgggatttaagtcaggtaccaagtctgagtttacagttattatccctatctgtaatacttgat atgattttcctatatcctgacaacctcgagtaattagatttgaggtgtaagcataaatcaggcggccgc (SEQ ID NO:64)

Figure 1B

Para4 (RTI-C11)

taatacgactcactatagggagaaattaaccctcactaaagggagactgttattttaagtgcatctatacgaacacctgctcgtctctc atcggtttttgtttggttccagataatatgggtcttgctaatgagtcaagtgtaattgtattgtcttgatcaacaaattttgagacgtctcc gttaccagtaacaattataggaacttgttctgattctttgtttaaactcctgagacttacttttgatgggactccaggatccattattttcatt gttgtgattaagccctcaattgtggcaagtgaacctttgatttgttgagtgtcattctttgtttgctgaattgtattttgagtaagcataattt gtcaactttcccttcaatcctgtctagtctcacttctaatgccttaattgcggccgc (SEQ ID NO:65)

HMPV (RTI-C12)

taatacgactcactatagggagaaattaaccctcactaaagggagaggaccatgctcactgcacttgattagtgctttcactgtcttgc agggcatatgaagagtcattgtcagcgcctgctgataagtcctatctggccaactccagtaattgtggttaaacttgcactcacttcct ctgttgcatttgccccgcacttcatatttgcatggagccttgcgagacattatgatttgtcatcctagagctgtgctaatatattgtattcct atttctgcagcatatttgtaatcagtatgtttagcatatagaatttctccacacaaaagtgttatttcttgttgcaatgatgagggtgtcact gcagttgttgtgcctacatctctttttattgtgtactgagactcttttaatatagcatgcttgtatgatagatcactcaggtgaatcccttga agagacattttcgcggccgc (SEQ ID NO:66)

AdV (RTI-C13)

taatacgactcactatagggagaaattaaccctcactaaagggagaatggccacccccatcgatgctgccccaatgggcatacatgc acatcgccggacaggatgcttcggagtacctgagtccgggtctggtgcagttcgcccgcgccacagacacctacttcaatctggg aaataagtttagaaatcccaccgtagcgccgacccacgatgtgaccaccgaccgtagccagcggctcatgttgcgcttcgtgactt gggacagaatatgctctatgccaactcagctcatgctctggacatgacctttgaggtggatcccatggatgagcccaccctgcttta cttctcttcgaagttttcgacgtggtcagagtgcatcagccacaccgcggcatcatcgaggcagtctacctgcgtacaccgttctcg gccggtaacgctaccacgtaagcggccgc (SEQ ID NO:67)

Rhino (RTI-C14)

taatacgactcactatagggagaaattaaccctcactaaagggagacaatagtagacctggcagatgaggctagaaattccccact ggcgacagtgttctagcctgcgtggctgcctgcacacccctttttgggctgtgaagccatatatttgacaaggtgtgaagagccccg tgtgctcacttttgagtcctccggcccctgaatgtggctaaccttaaccctgcagccattgcacacaatccagtgtgtatctggtcgta atgagcaattgcgggatgggaccaactactttgggtgtccgtgtttcatttttttcctttttatattttgcttatggtgacaatgtatatatagt atatatatatttgtcatcatgggcgctcaggtatctagacagaatgttgcggccgc (SEQ ID NO:68)

B. pertussis IS481 (RTI-C15)

taatacgactcactatagggagaaattaaccctcactaaagggagactaggtgtgaagattcaataggttgtatgcatggttcatccg aaccggatttgagaaactggaaatcgccaacccccagttcactcaaggagcccggccggatgaacacccataagcatgcccga ttgaccttcctacgtcgactcgaaatggtccagcaattgatcgcccatcaagtttgtgtgcctgaagcggcccgcttgctcaccgaca atggctcggcctttcgcagccgcgccttcgccgcgctgtgccatgagctgggcatcaagcaccgctttacccgaccttaccgccca cagaccaatggcaaggccgaacgcttcatccagtcggccttgcgtgagtgggcttacgctgcggccgc (SEQ ID NO: 69)

Figure 1C

C. pneumoniae (RTI-C16)

taatacgactcactatagggagaaattaaccctcactaaagggagacttgcgctacttggtgcgacgctattagcttacgtgctggat tttacggagactatgttttcgaccgtatcttaaaagtagatgcacctaaaacattttctatgggagccaacgctggcgtagcaacagct actggaacaaagtctgcgaccatcaattatcatgaatggcaagtaggagcctctctatcttacagactaaactctttagtgccatacat tggagtacaatggtctcgagcaacttttgatgctgataacatccgcattgctcagccaaaactacctacagctgttttaaacttaactgc atggaacccttctttactaggaaatgccacagcattgtctactactgattcgttctcaggcggccgc (SEQ ID NO:70)

M. pneumoniae (RTI-C17)

taatacgactcactatagggagaaattaaccctcactaaagggagagccagcaatttagctacacccgccctgacgaggtcgcgct gcgccacaccaatgccatcaacccgcgcttaaccccgtgaacgtatcgtaacacgagcttttcctccctccccctcacgggtgaaa atcccggggcgtgggccttagtgcgcgacaacagcgctaagggcatcactgccggcagtggcagtcaacaaaccacgtatgatc ccacccgaaccgaagcggctttgaccgcatcaaccacctttgcgttacgccggtatgacctcgccgggcgcgccttatacgacct cgatttttcgaagttaaacccgcaaacgcccacgcgcgaccaaaccgggcagatcacctttaaccccttggcggctttggtttgag tggggctgcaccccaacagtgaaacgcggccgc (SEQ ID NO:71)

RSV-A Pol Control (RTI-C18)

taatacgactcactatagggagaaattaaccctcactaaagggagaaataattctgttaggacatacattagtaaattgttctactactg acattaagctaaggccaaagcttatacagttttggaatactatatcaatatcttcatcaccatacttttctgttaatatgcgattaataggg ctagtatcaaagtgataatttgtagttctataagctggtattgatgcagggaattcacatggtctactactgactgtaaggcgatgcaaa tagttaacacttaaatattgtggaaataatttttggctttctcatatgttaacccaagaattcctatgctaaggcggccgc (SEQ ID NO:72)

RSV-B Pol Control (RTI-C19)

taatacgactcactatagggagaaattaaccctcactaaagggagaataattctattaggacatatgtttgtgaattgttccacaaccg acatcaggctaagaccaaaacttatgcaattttgaaacacaatgtcgatatcttcatctccatacttttctgttaatacatgattgatagga ctagtatcgaaatgataatttgttgttctataagctggtattgatgcagggaattcacatggtctactactgactgttaaacggtgtaaat aattgacacttagatattgtggaaacaactttttggctttttcatatgacagtccaagtgttccagtactcagtgcggccgc (SEQ ID NO:73)

Figure 1D

| Primer | [primer] uM |
|---|---|
| MS2 F | 0.4 |
| MS2 R | |
| InfA F | 0.3 |
| InfA R | |
| InfB F | 0.5 |
| InfB R | |
| H1N1 F | 0.5 |
| H1N1 R | |
| H5N1 F | 0.5 |
| H5N1 R | |
| RSV F | 0.8 |
| RSV R | |
| Para1 F | 0.6 |
| Para1 R | |
| Para2 F | 0.3 |
| Para2 R | |
| Para3 F | 0.75 |
| Para3 R | |
| Para4 F | 0.8 |
| Para4 R | |
| HMPV F | 1.2 |
| HMPV R | |
| AdV F | 0.7 |
| AdV R | |
| Rhi F | 1 |
| Rhi R | |
| Bper F | 0.2 |
| Bper R | |
| Cpn F | 0.4 |
| Cpn R | |
| Mpneu F | 0.35 |
| Mpneu R | |

| Primer | final [primer] (μM) |
|---|---|
| P-InfA R | 0.3 |
| Am-InfA F | 0.3 |
| P-InfB-2 R | 0.6 |
| Am-InfB-2 F | 0.6 |
| P-H1N1 R | 0.4 |
| Am-H1N1 F | 0.4 |
| P-H5N1 R | 0.7 |
| Am-H5N1 F | 0.7 |
| P-RSV-3 R | 0.6 |
| Am-RSV-3 F | 0.6 |
| P-Para1 R | 0.6 |
| Am-Para1 F | 0.6 |
| P-Para2 R | 0.4 |
| Am-Para2 F | 0.4 |
| P-Para3 R | 1 |
| Am-Para3 F | 1 |
| P-Para4 R | 0.7 |
| Am-Para4 F | 0.7 |
| P-hMPV R | 0.6 |
| Am-hMPV F | 0.6 |
| P-AdV F | 0.7 |
| AdV R | 0.7 |
| P-Rhi F | 1.5 |
| Rhi R | 1.5 |
| P-Bper F | 0.1 |
| Bper R | 0.1 |
| P-Cpn F | 0.8 |
| Cpn R | 0.8 |
| P-Mpneu F | 0.4 |
| Mpneu R | 0.4 |
| P-MS2-2 F | 0.8 |
| Am-MS2-2 R | 0.8 |
| P B-act F | 0.1 |
| B-act R | 0.1 |

COMPOSITIONS AND METHODS OF DETECTING RESPIRATORY PATHOGENS USING NUCLEIC ACID PROBES AND SUBSETS OF BEADS

FILING DATA

This application is associated with and claims priority from Australian Provisional Patent Application No. 2011904105, filed on 4 Oct. 2011, entitled "An Assay", the entire contents of which, are incorporated herein by reference.

REFERENCE TO SEQUENCE LISTING

This application incorporates by reference the sequence listing submitted as ASCII text filed via EFS-Web on Apr. 2, 2014. The Sequence Listing is provided as a file entitled "seq_1st_DAVI304_005apc.txt," created on Apr. 2, 2014, and which is approximately 35 kilobytes in size.

FIELD

The present disclosure is instructional for a multiplex nucleic acid amplification assay to detect and identify multiple respiratory pathogens.

BACKGROUND

Bibliographic details of the publications referred to by author in, this specification are collected alphabetically at the end of the description.

Reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The Australian Lung Foundation has reported that upper respiratory tract infections account for approximately 3-4 million visits to general practitioners (GPs) each year in Australia, costing taxpayers more than AU$150 million in direct cost and considerably more in indirect costs. Lower respiratory tract infections account for almost 3 million visits to GPs each year in Australia. The social and economic impact is further compounded by the number of hospitalizations attributed to respiratory infection. For example, community-acquired pneumonia is associated with an overall mortality rate in Australia of approximately 12% per annum for hospitalized patients aged greater than 65 years. This mortality rate increases to approximately 20% if co-morbid diseases are present (e.g. chronic obstructive pulmonary disease, congestive cardiac failure, diabetes). Furthermore, up to 30,000 hospital admissions for asthma and up to 40,000 hospital admissions for chronic obstructive pulmonary disease are precipitated by viral infections, implicated in 50 to 80% of all hospitalizations for asthma and chronic obstructive pulmonary disease. As a result, the direct and indirect cost burden of in Australia is estimated to be more than AU$500 million each year.

Etiological agents associated with respiratory infection can be classified into bacterial (including *Bordetella pertussis*), fungal and viral. Influenza types A or B viruses cause epidemics of disease almost every winter. Seasonal vaccinations (flu shots) can prevent illness from Influenza Types A and B, but do not protect against Influenza Type C.

Respiratory syncytial virus (RSV) is the leading cause of acute lower respiratory tract infections in infants and young children, with the majority of hospitalizations occurring in infants less than 1 year of age. Worldwide, RSV is believed to be associated with an annual mortality rate of 160,000-600,000 deaths. Those at increased risk of severe RSV disease include premature infants, and infants with congenital heart disease, neuromuscular disease, structural airway abnormalities and immunodeficiencies. Human parainfluenza viruses (HPIVs) are second only to RSV as a common cause of lower respiratory tract disease in young children. HPIVs can also cause serious lower respiratory tract disease with repeat infection, including pneumonia, bronchitis, and bronchiolitis, especially among the elderly and among patients with compromised immune systems.

Despite the magnitude of respiratory diseases worldwide, treatments are primarily supportive in nature. The use of bronchodilators, corticosteroids and leukotriene receptor antagonists (e.g. montelukast) has generally failed to demonstrate conclusive clinical benefit and antiviral drugs such as ribavirin have demonstrated only marginal clinical benefit. Current approaches to the treatment and prevention of respiratory infections include second-generation monoclonal antibodies and the highly potent antiviral compounds such as Oseltamivir (Tamiflu [Registered Trade Mark]) and Zanamivir (Relenza [Registered Trade Mark]) for the treatment of Influenza. Vaccine compositions are also in development. However, the effectiveness of existing treatment regimes is largely dependent on identifying the respiratory pathogen in question. Unfortunately, given the large number of possible respiratory pathogens and corresponding strains, the use of standard diagnostics to identify a particular respiratory pathogen in a sample is time-consuming, costly and frequently leads to incorrect or inconclusive diagnoses. A typical diagnostic virology laboratory uses viral culture, immunofluorescence staining and polymerase chain reaction (PCR) to screen for respiratory viruses. However, existing techniques have significant limitations. For example, viral culture is time-consuming and lacks the requisite sensitivity for detection, particularly of viruses that are labile during transport and/or have fastidious growth requirements. Immunofluorescence staining is insensitive, often leading to false-negative results and current PCR assays typically lack the high-throughput detection capability to effectively handle a large number of samples containing multiple targets.

There is a need to develop an assay to screen for multiple respiratory pathogens with a high level of rapidity and sensitivity.

SUMMARY

Provided herein is a method of screening a sample for a multiplicity of respiratory pathogens to detect a particular pathogen, the method comprising:

(a) isolating nucleic acid from the sample, which nucleic acid putatively comprises a nucleic acid from one or more respiratory pathogens;

(b) subjecting the nucleic acid to amplification, wherein an aqueous primer pair directs the amplification of a region of nucleic acid from a respiratory pathogen, the number of primer pairs being selected on the basis of the number of pathogens desired to be screened and wherein at least one member of the primer pair comprises a first optically detectable label that is incorporated into a resulting amplicon following amplification; wherein the amplicon is captured by hybridizing to an oligonucleotide probe that is complementary to a region of the amplicon and immobilized to a bead in a beadset, the beadset having subsets of beads, each subset being homogenous with respect to bead size and, optionally, intensity of a second optically detectable label, thereby creating a heterogeneous beadset based on size and/or second detectable label intensity and wherein the number of subsets corresponds to the number of respiratory pathogens to be screened;

(c) determining to which of the beads an amplicon has bound on the basis of the intensity of the first detectable label and, where amplicons are bound to multiple subsets of beads, distinguishing between the multiple subsets of beads on the basis of bead size and, optionally, on the basis of second optically detectable label intensity; wherein binding of an amplicon to a particular subset of beads is indicative of the presence of a particular respiratory pathogen in the sample.

In an embodiment, the amplification is a solid phase amplification.

In an embodiment, the amplicon initiated by extension of the primer comprising the first optically detectable label serves as a template for hybridization and extension of an oligonucleotide (hemi-nested primer) comprising a second optically detectable label, wherein the oligonucleotide is immobilized to a bead in a bead set.

Further taught is a method of screening a sample for a multiplicity of respiratory pathogens to detect a particular pathogen, the method comprising:

(a) isolating nucleic acid from the sample, which nucleic acid putatively comprises a nucleic acid from one or more respiratory pathogens;

(b) subjecting the nucleic acid to Solid phase amplification; wherein an aqueous primer pair directs the amplification of a region of nucleic acid from a respiratory pathogen, the number of primer pairs being selected on the basis of the number of pathogens desired to be screened and wherein at least one member of the primer pair comprises a first optically detectable label that is incorporated into a resulting amplicon following amplification, wherein the resulting amplicon initiated by extension of the primer comprising the first optically detectable label serves as a template for hybridization and extension of an oligonucleotide (hemi-nested primer) comprising a second optically detectable label, wherein the oligonucleotide is immobilized to a bead in a beadset, the beadset having subsets of beads, each subset being homogenous with respect to bead size and, optionally, intensity of a second optically detectable label, thereby creating a heterogeneous beadset based on size and/or second detectable label intensity and wherein the number of subsets corresponds to the number of respiratory pathogens to be screened;

(c) determining to which of the beads an amplicon has bound on the basis of the intensity of the first detectable label and, where amplicons are bound to multiple subsets of beads, distinguishing between the multiple subsets of beads on the basis of bead size and, optionally, on the basis of second optically detectable label intensity;

wherein binding of an amplicon to a particular subset of beads is indicative of the presence of a particular respiratory pathogen in the sample.

In an embodiment, the method comprises distinguishing between multiple subsets of beads on the basis of second optically detectable label intensity.

In an embodiment, the respiratory pathogen is selected from the group consisting of Influenza A, Influenza B, Influenza A H1N1, Influenza A H5N1, Respiratory Syncytial Virus subtype A, Respiratory Syncytial Virus subtype B, Human Parainfluenza Virus 1, Human Parainfluenza Virus 2. Human Parainfluenza Virus 3, Human Parainfluenza Virus 4, Human Metapneumovirus, Human Adenovirus subtype B, Human Adenovirus subtype C, Human Adenovirus subtype E, Human Enterovirus, Human Rhinovirus *Bordetella pertussis, Chlamydophila pneumoniae, Mycoplasma pneumoniae* and other microbes from the genera *Streptococcus, Haemophilus, Moraxella, Pseudomonas, Klebsiella, Stenotrophomonas, Acinetobacter, Staphylococcus, Mycoplasma, Legionella, Chlamydophila, Mycobacterium, Coxiella, Nocardia, Pneumocystis, Nocardia*, and *Aspergillus*.

In an embodiment, the nucleic acid from the respiratory pathogen is selected from the group consisting of the gene encoding Segment 7 of Influenza A matrix protein, the gene encoding Segment 4 of the Influenza B hemagglutinin, the gene encoding Segment 4 of the 2009 H1N1 pandemic strain of Influenza A, the gene encoding Segment 4 of the H5N1 pandemic strain of Influenza A, polymerase gene of the Respiratory Syncytial Virus (types A and B), the gene encoding hemagglutinin-neuraminidase glycoprotein of Human Parainfluenza Virus 1, 2 and 3, phosphoprotein gene of Human Parainfluenza Virus 4, the gene encoding the M2 region of the matrix protein of Human Metapneumovirus, the gene encoding the Hexon region of Adenovirus Types B, C and E, 5'UTR region of Human Rhinovirus/Enterovirus, the Insertion Element (IS) 481 of *Bordetella pertussis*, the gene encoding Major Outer Membrane Protein of *Chlamidophila pneumoniae* and the gene encoding P1 Cytadhesin of *Mycoplasma pneumoniae*.

In an embodiment, the primer pair comprises a forward primer selected from the group consisting of SEQ ID NOs:1 to 16 and SEQ ID NO:33 and 35 and a corresponding reverse primer selected from the group consisting of SEQ ID NOs:17 to 32 and SEQ ID NO:34 and 36.

In an embodiment, the oligonucleotide probe/hemi-nested primer is selected from the group consisting of SEQ ID NOs:37 to 52. In an embodiment, the oligonucleotide probe is a control oligonucleotide probe selected from SEQ ID NOs:53 and 54.

In an embodiment, the method comprises amplifying a control nucleic acid sequence using a primer pair comprising a forward primer selected from SEQ ID NO:33 and 35 and a corresponding reverse primer selected from SEQ ID NO:34 and 36.

In an embodiment, the method comprises subjecting the nucleic acid to amplification conditions with 16 primer pairs comprising forward primers of SEQ ID NOs:1 to 16 and corresponding reverse primers of SEQ ID NOs:17 to 32, and wherein the oligonucleotide probes/hemi-nested primers are selected from the group consisting of SEQ ID NOs:37 to 52.

In an embodiment, the method comprises amplifying a nucleic acid sequence using a primer pair comprising a forward and reverse primer and corresponding probe selected from SEQ ID NO:74 to 126.

In an embodiment, the method comprises subjecting the nucleic acid to solid phase amplification conditions with primer pairs comprising forward and reverse primers and corresponding probe selected from SEQ ID NOs:74 to 126 and wherein the primers are hemi-nested primers.

In an embodiment, the first and second optically detectable labels are fluorophores selected from the group consisting of hydroxycoumarin, aminocoumarin, methoxyciumarin, cascade blue, Lucifer yellow, NBD, Phyccerythrin (PE), PerCP, allophycocyanin, hoechst 33342, DAPI, SYTOX Blue, hoechst 33258, chromomycin A3; mithramycin, YOYO-I, SYTOX green, SYTOX orange, 7-AAD, acridine orange, TOTO-1, To-PRO-I, thiazole orange, TOTO-3, TO-PRO-3, LDS 751, Alexa Fluor dyes including Alexa Fluoro-350, -430, -488, -532, -546, -555, -556, -594, -633, -647, -660, -680, -700 and -750; BoDipy dyes, including BoDipy 630/650 and BoDipy 650/665; CY dyes, particularly Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4',5'-dichloro-2', T-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; $TRITC_3$ Tetramethylrhodamine (TMR); Carboxytetramethylrhodamine (TAMRA); Tetrachlorofluorescein (TET); Red $6B_5$ Fluor X, BODIPY-FL and Texas Red.

In an embodiment, the first optically detectable label is AlexaFluor-647.

In an embodiment, the second optically detectable label is boron-dipyrromethene (BoDipy)-TMR. In an embodiment, the second optically detectable label is attached to the oligonucleotide probe. In an embodiment, the second optically detectable label is attached to the oligonucleotide probe via an amino C6 modification of an internal thymidine residue of the oligonucleotide probe.

In an embodiment, the oligonucleotide probe is a hemi-nested oligonucleotide. In an embodiment, the oligonucleotide probe is covalently attached to the bead via a thiol or a methacryl linkage.

In an embodiment, the size of the beads within each subset is selected from the group consisting of 3.0 μm, 5.0 μm, 5.2 μm and 5.7 μm in diameter.

Further taught herein is a kit comprising two or more oligonucleotide primer pairs selected from SEQ ID NOs:1 and 17, 2 and 18, 3 and 19, 4 and 20, 5 and 21, 6 and 22, 7 and 23, 8 and 24, 9 and 25, 10 and 26, 11 and 27, 12 and 28, 13 and 29, 14 and 30, 15 and 31 and 16 and 32 and a corresponding probe selected from SEQ ID NOs:37 to 52, respectively.

Further taught herein is a kit comprising two or more oligonucleotide primer pairs and a corresponding primer probe as listed in Table 8 (SEQ ID NOs:74 to 126).

Nucleotide and amino acid sequences are referred to by a sequence identifier number (SEQ ID NO). A sequence listing is attached to the end of the specification and is incorporated herein by reference. The SEQ ID NOs correspond numerically to the sequence identifiers <400>1 (SEQ ID NO:1), <400>2 (SEQ ID NO:2) etc. A summary of the sequence identifiers used throughout the subject specification is provided in Table 1. A list of these sequences is provided in Table 2.

TABLE 1

Summary of sequence identifiers

| SEQUENCE ID NO: | DESCRIPTION |
|---|---|
| 1 | Forward primer for segment 7 of influenza A matrix protein |
| 2 | Forward primer for segment 4 of influenza B hemagglutinin |
| 3 | Forward primer for segment 4 of H1N1 |
| 4 | Forward primer for segment 4 of H5N1 |
| 5 | Froward primer for polymerase gene of Respiratory syncytial virus (types A and B) |
| 6 | Forward primer for hemagglutinin-neuraminidase glycoprotein of Human parainfluenza virus 1 |
| 7 | Forward primer for primer for hemagglutinin-neuraminidase glycoprotein of Human parainfluenza virus 2 |
| 8 | Forward primer for hemagglutinin-neuraminidase glycoprotein of Human parainfluenza virus 3 |
| 9 | Forward primer for hemagglutinin-neuraminidase glycoprotein of Human parainfluenza virus 4 |
| 10 | Forward primer for gene encoding M2 region of matrix protein of Human metapneumovirus |
| 11 | Forward primer for gene encoding the Hexon region of Adenovirus types B and E |
| 12 | Forward primer for gene encoding the Hexon region of Adenovirus type C |
| 13 | Forward primer of 5'UTR region of Human rhinovirus/enterovirus |
| 14 | Forward primer from *Bordetella pertussis* |
| 15 | Forward primer from *Chlamidophila pneumoniae* |
| 16 | Forward primer from *Mycoplasma pneumoniae* |
| 17 | Reverse primer for segment 7 of influenza A matrix protein |
| 18 | Reverse primer for segment 4 of influenza B hemagglutinin |
| 19 | Reverse primer for segment 4 of H1N1 |
| 20 | Reverse primer for segment 4 of H5N1 |
| 21 | Reverse primer for polymerase gene of Respiratory syncytial virus (types A and B) |
| 22 | Reverse primer for hemagglutinin-neuraminidase glycoprotein of Human parainfluenza virus 1 |
| 23 | Reverse primer for hemagglutinin-neuraminidase glycoprotein of Human parainfluenza virus 2 |
| 24 | Reverse primer for hemagglutinin-neuraminidase glycoprotein of Human parainfluenza virus 3 |
| 25 | Reverse primer for hemagglutinin-neuraminidase glycoprotein of Human parainfluenza virus 4 |
| 26 | Reverse primer for gene encoding M2 region of matrix protein of Human metapneumovirus |
| 27 | Reverse primer for gene encoding the Hexon region of Adenovirus types B and E |
| 28 | Reverse primer for gene encoding the Hexon region of Adenovirus type C |
| 29 | Reverse primer of 5'UTR region of Human rhinovirus/enterovirus |
| 30 | Reverse primer from *Bordetella pertussis* |
| 31 | Reverse primer from *Chlamidophila pneumoniae* |
| 32 | Reverse primer from *Mycoplasma pneumoniae* |
| 33 | Forward primer of MYL3 |
| 34 | Reverse primer of MYL3 |
| 35 | Forward primer of Matrix MS-2 |
| 36 | Reverse primer of Matrix MS-2 |
| 37 | Oligonucleotide probe complementary to a region of the amplicon generated by primer pairs SEQ ID NO: 1 and 17 |
| 38 | Oligonucleotide probe complementary to a region of the amplicon generated by primer pairs SEQ ID NO: 2 and 18 |
| 39 | Oligonucleotide probe complementary to a region of the amplicon generated by primer pairs SEQ ID NO: 3 and 19 |
| 40 | Oligonucleotide probe complementary to a region of the amplicon generated by primer pairs SEQ ID NO: 4 and 20 |
| 41 | Oligonucleotide probe complementary to a region of the amplicon generated by primer pairs SEQ ID NO: 5 and 21 |
| 42 | Oligonucleotide probe complementary to a region of the amplicon generated by primer pairs SEQ ID NO: 6 and 22 |
| 43 | Oligonucleotide probe complementary to a region of the amplicon generated by primer pairs SEQ ID NO: 7 and 23 |
| 44 | Oligonucleotide probe complementary to a region of the amplicon generated by primer pairs SEQ ID NO: 8 and 24 |
| 45 | Oligonucleotide probe complementary to a region of the amplicon generated by primer pairs SEQ ID NO: 9 and 25 |
| 46 | Oligonucleotide probe complementary to a region of the amplicon generated by primer pairs SEQ ID NO: 10 and 26 |
| 47 | Oligonucleotide probe complementary to a region of the amplicon generated by primer pairs SEQ ID NO: 11 and 27 |
| 48 | Oligonucleotide probe complementary to a region of the amplicon generated by primer pairs SEQ ID NO: 12 and 28 |
| 49 | Oligonucleotide probe complementary to a region of the amplicon generated by primer pairs SEQ ID NO: 13 and 29 |
| 50 | Oligonucleotide probe complementary to a region of the amplicon generated by primer pairs SEQ ID NO: 14 and 30 |
| 51 | Oligonucleotide probe complementary to a region of the amplicon generated by primer pairs SEQ ID NO: 15 and 31 |
| 52 | Oligonucleotide probe complementary to a region of the amplicon generated by primer pairs SEQ ID NO: 16 and 32 |

TABLE 1-continued

Summary of sequence identifiers

| SEQUENCE ID NO: | DESCRIPTION |
|---|---|
| 53 | Oligonucleotide probe complementary to a region of the amplicon generated by primer pairs SEQ ID NO: 33 and 34 |
| 54 | Oligonucleotide probe complementary to a region of the amplicon generated by primer pairs SEQ ID NO: 35 and 36 |
| 55 | MS2P (RTI-C1) |
| 56 | InA (RTI-C2) |
| 57 | InB (RTI-C3) |
| 58 | H1 (RTI-C4) |
| 59 | H5 (RTI-C5) |
| 60 | RSVA (RTI-C5) - Obsolete (see RTI-C18) |
| 61 | RSVB (RTI-C7) - Obsolete (see RTI-C19) |
| 62 | Para1 (RTI-C8) |
| 63 | Para2 (RTI-C9) |
| 64 | Para3 (RTI-C10) |
| 65 | Para4 (RTI-C11) |
| 66 | HMPV (RTI-C12) |
| 67 | AdV (RTI-C13) |
| 68 | Rhino (RTI-C14) |
| 69 | B. pertussis IS481 (RTI-C15) |
| 70 | C. pneumoniae (RTI-C16) |
| 71 | M. pneumoniae (RTI-C17) |
| 72 | RSV-A Pol Control (RTI-C18) |
| 73 | RSV-B Pol Control (RTI-C19) |
| 74 | Forward primer Am-InfA2 |
| 75 | Reverse primer InfA2 |
| 76 | Acry InfA2 |
| 77 | Forward primer Am-InfB-2 |
| 78 | Reverse InfB-2 |
| 79 | Acry AS InfB-2 |
| 80 | Reverse primer H1N1 |
| 81 | Forward primer H1N1 |
| 82 | Acry H1N1 |
| 83 | Forward primer Am-H5N1 |
| 84 | Reverse primer H5N1 |
| 85 | Acry AS-H5N1 |
| 86 | Forward primer Am-RSV-3 |
| 87 | Reverse primer RSV-3 |
| 88 | Acry AS-RSV-3 |
| 89 | Forward primer Am GB HPIV1 |
| 90 | Reverse primer GB HPIV1 |
| 91 | Acry GB HPIV1 |
| 92 | Forward primer Am-Para2 |
| 93 | Reverse primer Para2 |
| 94 | Acry AS-Para2 |
| 95 | Forward primer Am-Para3 |
| 96 | Reverse primer Para3 |
| 97 | Acry AS-Para3 |
| 98 | Forward primer Am-Para4 |
| 99 | Reverse primer Para4 |
| 100 | Acry GB HPIV-4 Pr1 |
| 101 | Acry GB HPIV-4 Pr2 |
| 102 | Forward primer Am-hMPV |
| 103 | Reverse primer hMPV |
| 104 | Acry AS-hMPV |
| 105 | Forward primer AdV |
| 106 | Reverse primer AdV |
| 107 | Acry AdV B/E |
| 108 | Acry AdV C |
| 109 | Reverse primer truncRhi |
| 110 | Forward primer T7truncRhi |
| 111 | Acry Rhi |
| 112 | Forward primer Bper |
| 113 | Reverse primer Bper |
| 114 | Acry Bper |
| 115 | Forward primer Cpn |
| 116 | Reverse primer Cpn |
| 117 | Acry Cpn |
| 118 | Forward primer Mpneu |
| 119 | Reverse primer Mpneu |
| 120 | Acry Mpneu |
| 121 | Reverse primer MS2-2 |
| 122 | Forward primer MS2-2 |
| 123 | Acry MS2-2 |
| 124 | Forward primer MYL3 |
| 125 | Reverse primer MYL3 |
| 126 | Pap type ProbeMLC_Int Oligonucleotide |
| 127 | Forward primer Am-InfA |
| 128 | Reverse primer P-InfA |
| 129 | AS InfA |
| 130 | Forward primer alt Am-InfA |
| 131 | Reverse primer P-InfA |
| 132 | AS InfA |
| 133 | Forward primer InfB |
| 134 | Reverse primer InfB |
| 135 | InfB |
| 136 | Forward primer RSV |
| 137 | Reverse primer RSV |
| 138 | RSV |
| 139 | Forward primer Am-Para1 |
| 140 | Reverse primer P-Para1 |
| 141 | AS-Para1 |

TABLE 2

Summary of sequences

| SEQUENCE ID NO: | DESCRIPTION |
|---|---|
| 1 | CGAGGTCGAAACGTAYGTTCTYTCTAT |
| 2 | TACGGTGGATTAAACAAAAGCAAGCC |
| 3 | CCCAAGACAAGTTCATGGCCCAATCA |
| 4 | GCTCTGCGATCTAGATGGAGTGAAGCC |
| 5 | ACAGTCAGTAGTAGACCATGTGAATTC |
| 6 | TGGTGATGCAATATATGCGTATTCATC |
| 7 | CYCGTCCTGGAGTCATGCCATGCAA |
| 8 | CAAGTTGGCAYAGCAAGTTACAATTAGGA |
| 9 | GTTGATCAAGACAATACAATTACACTTGA |

TABLE 2-continued

Summary of sequences

| SEQUENCE ID NO: | DESCRIPTION |
|---|---|
| 10 | GACAAATCATMATGTCTCGYAARGCTCC |
| 11 | TGCCSCARTGGKCDTACATGCACATC |
| 12 | TGCCSCARTGGKCDTACATGCACATC |
| 13 | GAAACACGGACACCCAAAGTAGT |
| 14 | CCGGCCGGATGAACACCCATAAGCA |
| 15 | CATGAATGGCAAGTAGGAGCCTCTC |
| 16 | GAACCGAAGCGGCTTTGACCGCATC |
| 17 | GCCATTCCATGAGAGCCTCRAGATC |
| 18 | CAGGAGGTCTATATTTGGTTCCATTGGC |
| 19 | GCTTTTTGCTCCAGCATGAGGACAT |
| 20 | YCTTCTCCACTATGTAAGACCATTCCGG |
| 21 | RTCRATATCTTCATCACCATACTTTTCTGTTA |
| 22 | CCGGGTTTAAATCAGGATACATATCTG |
| 23 | CRTTAAGCGGCCACACATCTGCGT |
| 24 | GTCCCCATGGACATTCATTGTTTCCTGGT |
| 25 | TAAGTGCATCTATACGAACRCCTGCTC |
| 26 | CTATCWGGCCAACTCCAGTAATTGTG |
| 27 | GCRCGGGCRAACTGCACCAG |
| 28 | GCRCGGGCRAACTGCACCAG |
| 29 | ACTCACTATAGGAGCCTGCGTGGCKGCC |
| 30 | GGGCCGCTTCAGGCACACAAACTTG |
| 31 | AGTTTTGGCTGAGCAATGCGGATGT |
| 32 | GCGTGGGCGTITGCGGGTTTAACTT |
| 33 | GCACCCAGACAATACACACAGGTGT |
| 34 | GGCGGAAGTCAGCATGTGTCTG |
| 35 | GCACGCTCCTGCTACAGCCTCTTCC |
| 36 | CTTTTGCAGGACTTCGGTCGACGCC |
| 37 | GAATTCGGATCCAGTCTCTGCGCGATCTCGGCTTTGAG |
| 38 | GAATTCGGATCCGGTGTTTTCACCCATATTGGGCAATT |
| 39 | GAATTCGGATCCCATGCTGCCGTTACACCTTTGTTCG |
| 40 | GAATTCGGATCCCCCAGGAGCCAT CCAGCTACACTAC |
| 41 | GAATTCGGATCCGTTCTATAAGCTGGTATTGATGCAGG |
| 42 | GAATTCGGATCCCCTATATCTGCACATCCTTGAGTGATT |
| 43 | GAATTCGGATCCACCCCTGTGATGCAATTAGCAGGGCA |
| 44 | GAATTCGGATCCAGCACATTATGCCATGTCCATTTTATCC |
| 45 | GAATTCGGATCCGGTTCCAGAYAAWATGGGTCTTGCTA |
| 46 | GAATTCGGATCCTTGCCCCGYACTTCATATTTGCA |

TABLE 2-continued

Summary of sequences

| SEQUENCE ID NO: | DESCRIPTION |
|---|---|
| 47 | GAATTCGGATCCGCTTCGGAGTACCTGAGTCCGGGT |
| 48 | GAATTCGGATCCTCGGGCCAGGACGCCTCGGAGTAC |
| 49 | GAATTCGGATCCTCCTCCGGCCCCTGAATGYGGCTAA |
| 50 | GAATTCGGATCCTGCCCGATTGACCTTCCTACGTCGA |
| 51 | GAATTCGGATCCTGGTCTCGAGCAACTTTTGATGCTG |
| 52 | GAATTCGGATCCGGGCGCGCCTTATACGACCTCGATT |
| 53 | AAAGGGAGGACAGCTATGGACCAAACACAGACACAGAGAG<br>ACCCACAGACA |
| 54 | GAATTCGGATCCGAAGTGCCGCAGAACGTTGCGAACC |
| 55 | taatacgactcactatagggagaaattaaccctcactaaagggagagtttcggcttctccctcgacgc<br>acgctcctgctacagcctcttccctgtaagccaaaacttgacttacatcgaagtgccgcagaacgttg<br>cgaaccgggcgtcgaccgaagtcctgcaaaaggtcacccagggtaattttaaccttggtgttgcttta<br>gcagaggccaggtcgacagcctcacaactcgcgacgcaaaccattgcgctcgtgaaggcgtacac<br>tgccgctcgtcgcggtaattggcgccaggcgctccgctaccttgccctaaacgaagatcgaaagttt<br>cgatcaaaacacgtggccggcaggtggttggagttgcagttcggttggttaccactaatgagtgcgg<br>ccgc |
| 56 | taatacgactcactatagggagaaattaaccctcactaaagggagactttggccccatggaatgttatc<br>tcccttttaagcttcctatacagtttaactgctctgtccatgttatttggatccccattcccatttagggcatt<br>ttggacaaagcgtctacgctgcagtcctcgctcactgggcacggtgagcgtgaacacaaatcctaaa<br>atccccttagtcagaggtgacaggattggtcttgtctttagccattccatgagagcctcaagatctgtgt<br>tcttccctgcaaagacatcttcaagtctctgcgcgatctcggctttgaggggggcctgacgggacgata<br>gagagaacgtacgtttcgacctcggttagaagactcatctttcaatatctagcggccgc |
| 57 | taatacgactcactatagggagaaattaaccctcactaaagggagacttctaagaaaccagcaatag<br>ctccgaagaaacccctttcctttaatagttttgcaggaggtctatatttggttccattggcaagcttcaaa<br>ggtgttttcacccatattgggcaatttcctatggcttttgcatgttctcctgtgtagtaaggcttgcttttgttt<br>aatccaccgtatttttcgtgaaggcaatctgcttaatttggtcttctccttctgtacaaatgtatggtacttct<br>actgttagtggattcgttgctgttttgttgttgtcgttctttgggacagcccaagccattgttgcgaaaaat<br>ccgtttctactggtaacgttagggcaagatcctgaggttccaagtctgtagggtcctcctggtgcctttt<br>ctgcattgataacgttagcggccgc |
| 58 | taatacgactcactatagggagaaattaaccctcactaaagggagatttatcattaatgtaggatttgct<br>gagctttgggtatgaatttcctttttaactagccatattaaatttttgtagaagctttttgctccagcatgag<br>gacatgctgccgttacacctttgttcgagtcatgattgggccatgaacttgtcttggggaatatctcaaa<br>cctttcaaatgatgacactgagctcaattgctctcttagctcctcataatcgatgaaatctcctgggtaac<br>acgttccattgtctgaactagatgtttccacaatgtaggaccatgagcttgctgtggagagtgattcaca<br>ctctggatttcccaggatccagccagcaatgttacatttacccaaatgcaatggggctacccctcttag<br>tttgcatagtttcccgttatgcttgtcttctagaaggttaacagagtgtgttactgttacattcttttctagtac<br>tgtgtctgcggccgc |
| 59 | aatacgactcactatagggagaaattaaccctcactaaagggagacacaaatttaaatgcaaattctg<br>cattgtaacgatccattggagcacatccataaagatagaccagccaccatgattgccagtgctaggg<br>aactcgccactgttgaataaattgacagtatttggtaagttcctattgattccaattttatttcagttcttcat<br>agtcgttgaaattccctgggtaacagaggtcattggctggattggccttctccactatgtaagaccattc<br>cggcacattgatgaattcgtcacacattgggtttccgaggagccatccagctacactacaatctcttaa<br>aattagaggcttcactccatctagatcgcagagcttcccgttgtgtgtctgcggccgc |
| 60 | taatacgactcactatagggagaaattaaccctcactaaagggagatagaaaatgtctttatgattcca<br>cgatttttattggatgctgtacatttagttttgccatagcatgacacaatggctcctagagatgtgataac<br>ggagctgcttacatctgtttttgaagtcataattttgcaatcatatgtgtacctctgtattctcccattatgcc<br>taggccagcagcattgcctaatactacactggagaagtgaggaaattgagtcaaagacaataatgat<br>gcttttgggttgttcaatatatggtagaaccctgcttctccacccaatttttgggcatattcatatgctccgt<br>tggatggtgtatttgctggatgacagaagttgatctttgttgagtgtatcattcaacttgactttgctaaga<br>gccattttgtatttgccccatctttcatcttatgtctctccttaattttaaattactataattttcaggctccatt<br>tgaactatggagtgtggtgcggccgc |
| 61 | taatacgactcactatagggagaaattaaccctcactaaagggagaataatcccacgatttttgttgga<br>tgcagtgcatttagttttaccatagcatgacactatagctccaagagaagtaattactgagctgcttatgt<br>ctgtttttgatgtcatatactctcccattatgcctagacctgctgcattgcctaggaccacacttgagaag<br>ttaggaaattgagttaatgacagcaatgatgcttttggattgttcaatatatggtagaatccagcttctcct<br>cccaacttctgtgcatactcataattgggagtgtcaatattatctcctgtactacgttgaatagtgtatttg<br>ctggatgacagcagctgatccttatttaatgtatcatttaacttgactttgctaagagccatctttgtatttg<br>ccccaatttatgttattggctttacttttatttttaattactaaaacggattagctccttcttaactattgagcat<br>tgttgtttgaggaatagcttggtttggttgggttggtttttttttgttggaatgcggccgc |

TABLE 2-continued

Summary of sequences

| SEQUENCE ID NO: | DESCRIPTION |
|---|---|
| 62 | taatacgactcactatagggagaaattaaccctcactaaagggagattgaaccagttgcagtctgggt<br>ttcctggtcgcgacaggactttatgaggcgcccaattaatggtcatggggttgttgatatctaatgatcc<br>tatttgcaggttggagtgccaacctgaaccccttgttcctgcagctattacagaacatgatttcctgttgt<br>cgttgatgtcataggtatgagaaattaccgggtttaaatcaggatacatatctgaatttaaggatatgtaa<br>cctaattgtaaaacctgatatgacttccctatatctgcacatccttgagtgattaagtttgatgaatacgca<br>tatattgcatcaccaattgataatgaaggtagtctaacacatcctgaaattgtggtggatccagaaagta<br>gacttggtccaggtaataatgagagcggccgc |
| 63 | taatacgactcactatagggagaaattaaccctcactaaagggagacattaagcggccacacatctg<br>cgtacacccctgtgatgcaattagcagggcaaaaacttgttgcattgcatggcatgactccaggacg<br>aggaacttgataggacggtacccattgagcctcaatgatcggagctgcaggattgattgtggcccac<br>tgccctgttgtatttggaagagatatgactctttcaataaaggtatcattataataatagaaagcaagtct<br>cagttcagctagatcagtcgtggcataatcttctttttcagaccttgtagctacatagcaatacaagaca<br>caacctcctggtatagcagtgactgaacagcttttgcgattgattccatcacttaggtaaatggttttcat<br>agtcctgcggccgc |
| 64 | taatacgactcactatagggagaaattaaccctcactaaagggagatggacatgaatgtccccatgg<br>acattcattgtttcctggtcttgatagcacattatgccatgtccattttatccttatatcactgtagtcagtaa<br>tgtcaattattcctaattgtaacttgctgtgccaacttgtagatcttgtatatataaagtatgagagatcctg<br>ggatttaagtcaggtaccaagtctgagtttacagttattatccctatctgtaatacttgatatgattttcctat<br>atcctgacaacctcgagtaattagatttgaggtgtaagcataaatcaggcggccgc |
| 65 | taatacgactcactatagggagaaattaaccctcactaaagggagactgttattttaagtgcatctatac<br>gaacacctgctcgtctctcatcggtttttttgtttggttccagataatatgggtcttgctaatgagtcaagtg<br>taattgtattgtcttgatcaacaaattttgagacgtctccgttaccagtaacaattataggaacttgttctga<br>ttctttgtttaaactcctgagacttacttttgatgggactccaggatccattattttcattgttgtgattaagc<br>cctcaattgtggcaagtgaacctttgatttgttgagtgtcattctttgtttgctgaattgtattttgagtaagc<br>ataattttgtcaactttcccttcaatcctgtctagtctcacttctaatgccttaattgcggccgc |
| 66 | taatacgactcactatagggagaaattaaccctcactaaagggagaggaccatgctcactgcacttg<br>attagtgctttcactgtcttgcagggcatatgaagagtcattgtcagcgcctgctgataagtcctatctg<br>gccaactccagtaattgtggttaaacttgcactcacttcctctgttgcatttgccccgcacttcatatttgc<br>atggagccttgcgagacattatgatttgtcatcctagagctgtgctaatatattgtattcctatttctgcag<br>catatttgtaatcagtatgtttagcatatagaatttctccacacaaaagtgttatttcttgttgcaatgatga<br>gggtgtcactgcagttgttgtgcctacatctctttttattgtgtactgagactcttttaatatagcatgcttgt<br>atgatagatcactcaggtgaatcccttgaagagacattttcgcggccgc |
| 67 | taatacgactcactatagggagaaattaaccctcactaaagggagaatggccaccccatcgatgctg<br>ccccaatgggcatacatgcacatcgccggacaggatgcttcggagtacctgagtccgggtctggtg<br>cagttcgcccgcgccacagacacctacttcaatctgggaaataagtttagaaatcccaccgtagcgc<br>cgacccacgatgtgaccaccgaccgtagccagcggctcatgttgcgcttcgtgacttgggacagaa<br>tatgctctatgccaactcagctcatgctctggacatgacctttgaggtggatcccatggatgagcccac<br>cctgctttatcttctcttcgaagttttcgacgtggtcagagtgcatcagccacaccgcggcatcatcga<br>ggcagtctacctgcgtacaccgttctcggccggtaacgctaccacgtaagcggccgc |
| 68 | taatacgactcactatagggagaaattaaccctcactaaagggagacaatagtagacctggcagatg<br>aggctagaaattccccactggcgacagtgttctagcctgcgtggctgcctgcacaccccttttttgggc<br>tgtgaagccatatatttgacaaggtgtgaagagccccgtgtgctcacttttgagtcctccggcccctga<br>atgtggctaaccttaaccctgcagccattgcacacaatccagtgtgtatctggtcgtaatgagcaattg<br>cgggatgggaccaactactttgggtgtccgtgtttcatttttttttcctttttatattttgcttatggtgacaatgt<br>atatatagtatatatatatttgtcatcatgggcgctcaggtatctagacagaatgttgcggccgc |
| 69 | taatacgactcactatagggagaaattaaccctcactaaagggagactaggtgtgaagattcaatagg<br>ttgtatgcatggttcatccgaaccggatttgagaaactggaaatcgccaacccccccagttcactcaag<br>gagcccggccggatgaacacccataagcatgcccgattgaccttcctacgtcgactcgaaatggtc<br>cagcaattgatcgcccatcaagtttgtgtgcctgaagcggcccgcttgctcaccgacaatggctcgg<br>cctttcgcagccgcgccttcgccgcgctgtgccatgagctgggcatcaagcaccgctttacccgacc<br>ttaccgcccacagaccaatggcaaggccgaacgcttcatccagtcggccttgcgtgagtgggcttac<br>gctgcggccgc |
| 70 | taatacgactcactatagggagaaattaaccctcactaaagggagacttgcgctacttggtgcgacgc<br>tattagcttacgtgctggattttacggagactatgttttcgaccgtatcttaaaagtagatgcacctaaaa<br>cattttctatgggagccaacgctggcgtagcaacagctactggaacaaagtctgcgaccatcaattat<br>catgaatggcaagtaggagcctctctatcttacagactaaactctttagtgccatacattggagtacaat<br>ggtctcgagcaacttttgatgctgataacatccgcattgctcagccaaaactacctacagctgttttaaa<br>cttaactgcatggaacccttctttactaggaaatgccacagcattgtctactactgattcgttctcaggcg<br>gccgc |
| 71 | taatacgactcactatagggagaaattaaccctcactaaagggagagccagcaatttagctacaccc<br>gccctgacgaggtcgcgctgcgccacaccaatgccatcaacccgcgcttaaccccgtgaacgtatc<br>gtaacacgagcttttcctccctcccccctcacgggtgaaaatcccggggcgtgggccttagtgcgcga<br>caacagcgctaagggcatcactgccggcagtggcagtcaacaaaccacgtatgatcccacccgaa |

TABLE 2-continued

| Summary of sequences | |
|---|---|
| SEQUENCE ID NO: | DESCRIPTION |
| | ccgaagcggctttgaccgcatcaaccacctttgcgttacgccggtatgacctcgccgggcgcgcctt atacgacctcgatttttcgaagttaaacccgcaaacgcccacgcgcgaccaaaccgggcagatcac ctttaacccctttggcggctttggtttgagtggggctgcaccccaacagtgaaacgcggccgc |
| 72 | taatacgactcactatagggagaaattaaccctcactaaagggagaaataattctgttaggacatacat tagtaaattgttctactactgacattaagctaaggccaaagcttatacagttttggaatactatatcaatat cttcatcaccatacttttctgttaatatgcgattaatagggctagtatcaaagtgataatttgtagttctata agctggtattgatgcagggaattcacatggtctactactgactgtaaggcgatgcaaatagttaacact taaatattgtggaaataatttttttggctttctcatatgttaacccaagaattcctatgctaaggcggccgc |
| 73 | taatacgactcactatagggagaaattaaccctcactaaagggagaataattctattaggacatatgtttg tgaattgttccacaaccgacatcaggctaagaccaaaacttatgcaattttgaaacacaatgtcgatatct tcatctccatacttttctgttaatacatgattgataggactagtatcgaaatgataatttgttgttctataagct ggtattgatgcagggaattcacatggtctactactgactgttaaacggtgtaaataattgacacttagatat tgtggaaacaacttttttggctttttcatatgacagtccaagtgttccagtactcagtgcggccgc |
| 74 | CGAGGTCGAAACGTAYGTTCTYTCTAT |
| 75 | GCCATTCCATGAGAGCCTCRAGATC |
| 76 | AATTGAATTCGGATCCAGTCTCTGCGCGATCTCGGCTTTGAG |
| 77 | TACGGTGGATTAAACAAAAGCAAGCC |
| 78 | CAGGAGGTCTATATTTGGTTCCATTGGC |
| 79 | GAATTCGGATCCGGTGTTTTCACCCATATTGGGCAATT |
| 80 | GCTTTTTGCTCCAGCATGAGGACAT |
| 81 | CCCAAGACAAGTTCATGGCCCAATCA |
| 82 | AATTGAATTCGGATCCCGAACAAAGGTGTAACGGCAGCATG |
| 83 | GCTCTGCGATCTAGATGGAGTGAAGCC |
| 84 | YCTTCTCCACTATGTAAGACCATTCCGG |
| 85 | AATTGAATTCGGATCCCCGAGGAGCCATCCAGCTACACTAC |
| 86 | ACAGTCAGTAGTAGACCATGTGAATTC |
| 87 | RTCRATATCTTCATCACCATACTTTTCTGTTA |
| 88 | AATTGAATTCGGATCCGTTCTATAAGCTGGTATTGATGCAGG |
| 89 | TGGTGATGCAATATATGCGTATTCATC |
| 90 | CCGGGTTTAAATCAGGATACATATCTG |
| 91 | GAATTCGGATCCCCTATATCTGCACATCCTTGAGTGATT |
| 92 | CYCGTCCTGGAGTCATGCCATGCAA |
| 93 | CRTTAAGCGGCCACACATCTGCGT |
| 94 | GAATTCGGATCCACCCCTGTGATGCAATTAGCAGGGCA |
| 95 | CAAGTTGGCAYAGCAAGTTACAATTAGGA |
| 96 | GTCCCCATGGACATTCATTGTTTCCTGGT |
| 97 | GAATTCGGATCCAGCACATTATGCCATGTCCATTTTATCC |
| 98 | GTTGATCAAGACAATACAATTACACTTGA |
| 99 | TAAGTGCATCTATACGAACRCCTGCTC |
| 100 | GAATTCGGATCC GGTTCCAGACAAAATGGGTCTTGCTA |
| 101 | GAATTCGGATCC GGTTCCAGATAATATGGGTCTTGCTA |
| 102 | GACAAATCATMATGTCTCGYAARGCTCC |

TABLE 2-continued

| Summary of sequences | |
|---|---|
| SEQUENCE ID NO: | DESCRIPTION |
| 103 | CTATCWGGCCAACTCCAGTAATTGTG |
| 104 | GAATTCGGATCCTTGCCCCGYACTTCATATTTGCA |
| 105 | TGCCSCARTGGKCDTACATGCACATC |
| 106 | GCRCGGGCRAACTGCACCAG |
| 107 | AATTGAATTCGGATCCGCTTCGGAGTACCTGAGTCCGGGT |
| 108 | AATTGAATTCGGATCCTCGGGCCAGGACGCCTCGGAGTAC |
| 109 | GAAACACGGACACCCAAAGTAGT |
| 110 | ACTCACTATAGGAGCCTGCGTGGCKGCC |
| 111 | GAATTCGGATCCTCCTCCGGCCCCTGAATGYGGCTAA |
| 112 | CCGGCCGGATGAACACCCATAAGCA |
| 113 | GGGCCGCTTCAGGCACACAAACTTG |
| 114 | GAATTCGGATCCTGCCCGATTGACCTTCCTACGTCGA |
| 115 | CATGAATGGCAAGTAGGAGCCTCTC |
| 116 | AGTTTTGGCTGAGCAATGCGGATGT |
| 117 | GAATTCGGATCCTGGTCTCGAGCAACTTTTGATGCTG |
| 118 | GAACCGAAGCGGCTTTGACCGCATC |
| 119 | GCGTGGGCGTTTGCGGGTTTAACTT |
| 120 | GAATTCGGATCCGGGCGCGCCTTATACGACCTCGATT |
| 121 | CTTTTGCAGGACTTCGGTCGACGCC |
| 122 | GCACGCTCCTGCTACAGCCTCTTCC |
| 123 | AATTGAATTCGGATCCGAAGTGCCGCAGAACGTTGCGAACC |
| 124 | GCACCCAGACAATACACACAGGTGT |
| 125 | GGCGGAAGTCAGCATGTGTCTG |
| 126 | AAAGGGAGGACAGCTATGGACCAAACACAGACACAGAGAGA CCCACAGACA |
| 127 | TRGGRTTTGTGTTCACGCTCACCGTG |
| 128 | GGGCATTTTGGACAAAGCGTCTACGC |
| 129 | GAATTCGGATCCTGCAGTCCTCGCTCACTGGGCA |
| 130 | GACAAGACCAATCCTGTCACCTCTGAC |
| 131 | GGGCATTTTGGACAAAGCGTCTACGC |
| 132 | GAATTCGGATCCTGCAGTCCTCGCTCACTGGGCA |
| 133 | GCACCAGGAGGACCCTACARAMTTGGA |
| 134 | TTGGGACRGCCCAAGCCATTGTTGCG |
| 135 | ACCTCAGGRTCTTGCCCTAACGYTACCA |
| 136 | TTGGGWGGAGAAGCWGGWTTCTACCA |
| 137 | ATTATGCCTAGRCCWGCWGCATTGCC |
| 138 | ARYARTGATGCTTTTGGRTTGTTCAATAT |
| 139 | TGGCACTCCAACCTGCAAATAGGATCA |

TABLE 2-continued

| Summary of sequences | |
|---|---|
| SEQUENCE ID NO: | DESCRIPTION |
| 140 | CCAGTTGCAGTCTTGGTTTCCTGGTCG |
| 141 | GAATTCGGATCCACAGGACTTYATGAGGCGCCCA |

BRIEF DESCRIPTION OF THE FIGURES

FIG. 1A through D show the control construct insert sequences and their identifiers.

DETAILED DESCRIPTION

Figure 2:
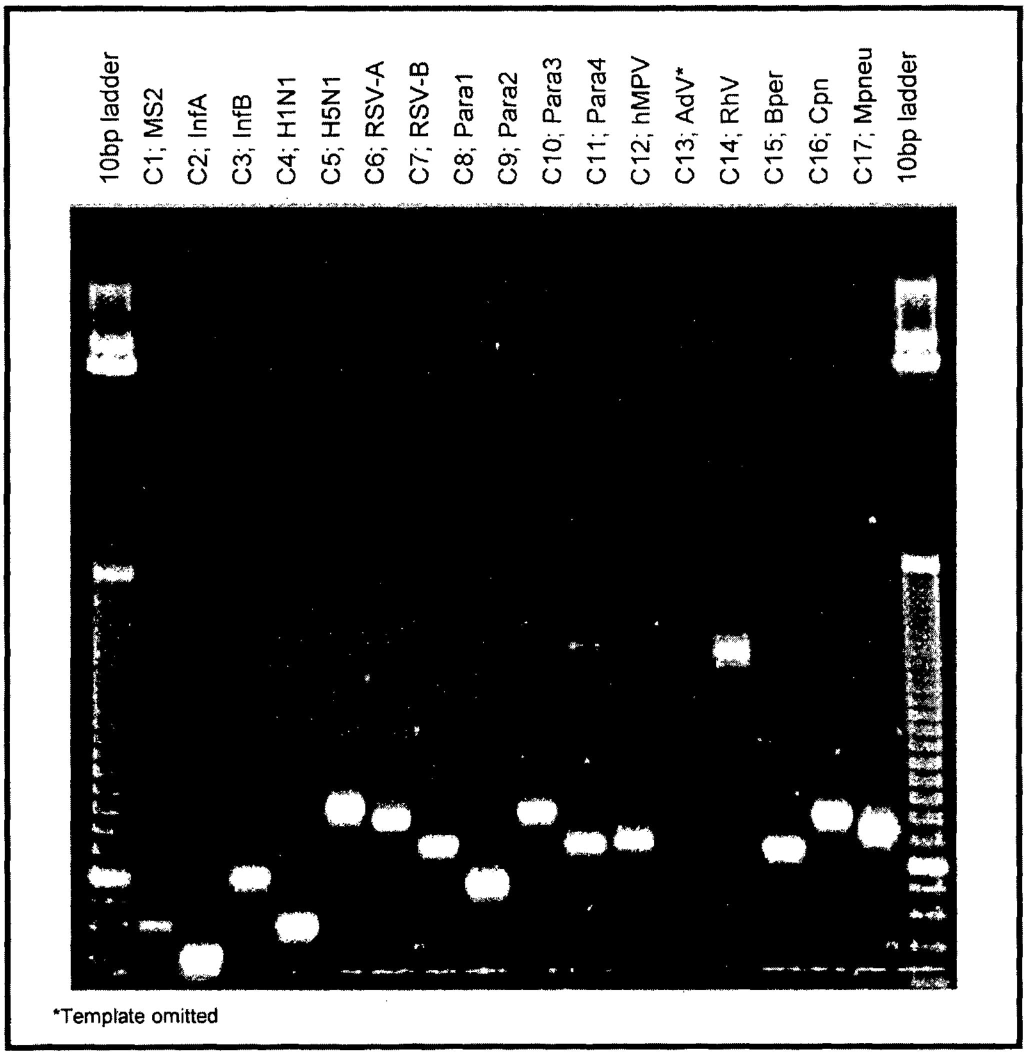
FIG. 2 is a photographical representation showing the confirmation of the identity of RNA templates by specific RT-PCR.

Throughout this specification, unless the context requires otherwise, the word “comprise” or variations such as “comprises” or “comprising”, will be understood to imply the inclusion of a stated element or integer or method step or group of elements or integers or method steps but not the exclusion of any element or integer or method step or group of elements or integers or method steps.

As used in the subject specification, the singular forms “a”, “an” and “the” include singular and plural aspects unless the context clearly dictates otherwise. Thus, for example, reference to “a respiratory pathogen” includes a single respiratory pathogen, as well as two or more different respiratory pathogens; reference to “an agent” includes a single agent, as well as two or more agents; reference to “the disclosure” includes a single or multiple aspects taught by the disclosure. The aspects taught herein are encompassed by the term “invention”. All such aspects are enabled within the width of the claims.

The present disclosure teaches the detection and differentiation of multiple respiratory pathogens in a sample.

Enabled herein is a method of screening a sample for a multiplicity of respiratory pathogens to detect a particular pathogen, the method comprising:

(a) isolating nucleic acid from the sample, which nucleic acid putatively comprises a nucleic acid from one or more respiratory pathogens;

(b) subjecting the nucleic acid to amplification, wherein an aqueous primer pair directs the amplification of a region of nucleic acid from a respiratory pathogen, the number of primer pairs being selected on the basis of the number of pathogens desired to be screened and wherein at least one member of the primer pair comprises a first optically detectable label that is incorporated into a resulting amplicon following amplification; wherein the amplicon is captured by hybridizing to an oligonucleotide probe that is complementary to a region of the amplicon and immobilized to a bead in a beadset, the beadset having subsets of beads, each subset being homogenous with respect to bead size and, optionally, intensity of a second optically detectable label, thereby creating a heterogeneous beadset based on size and/or second detectable label intensity and wherein the number of subsets corresponds to the number of respiratory pathogens to be screened;

(c) determining to which of the beads an amplicon has bound on the basis of the intensity of the first detectable label and, where amplicons are bound to multiple subsets of beads, distinguishing between the multiple subsets of beads on the basis of bead size and, optionally, on the basis of second optically detectable label intensity;

wherein binding of an amplicon to a particular subset of beads is indicative of the presence of a particular respiratory pathogen in the sample.

In an embodiment, the amplification is a solid phase amplification.

In an embodiment, the amplicon initiated by extension of the primer comprising the first optically detectable label serves as a template for hybridization and extension of an oligonucleotide (hemi-nested primer) comprising a second optically detectable label, wherein the oligonucleotide is immobilized to a bead in a beast set.

Further enabled is a method of screening a sample for a multiplicity of respiratory pathogens to detect a particular pathogen, the method comprising:

(a) isolating nucleic acid from the sample, which nucleic acid putatively comprises a nucleic acid from one or more respiratory pathogens;

(b) subjecting the nucleic acid to solid phase amplification; wherein an aqueous primer pair directs the amplification of a region of nucleic acid from a respiratory pathogen, the number of primer pairs being selected on the basis of the number of pathogens desired to be screened and wherein at least one member of the primer pair comprises a first optically detectable label that is incorporated into a resulting amplicon following amplification, wherein the resulting amplicon initiated by extension of the primer comprising the first optically detectable label serves as a template for hybridization and extension of an oligonucleotide (hemi-nested primer) comprising a second optically detectable label, wherein the oligonucleotide is immobilized to a bead in a beadset, the beadset having subsets of beads, each subset being homogenous with respect to bead size and, optionally, intensity of a second optically detectable label, thereby creating a heterogeneous beadset based on size and/or second detectable label intensity and wherein the number of subsets corresponds to the number of respiratory pathogens to be screened;

(c) determining to which of the beads an amplicon has bound on the basis of the intensity of the first detectable label and, where amplicons are bound to multiple subsets of beads, distinguishing between the multiple subsets of beads on the basis of bead size and, optionally, on the basis of second optically detectable label intensity;

wherein binding of an amplicon to a particular subset of beads is indicative of the presence of a particular respiratory pathogen in the sample.

The term "pathogen" refers to a microorganism or virus that is capable of infecting or colonizing a host. A host may be a single cell or a subject comprising a multiplicity of cells. Hence, a "host" includes a subject. Exemplary pathogens include viruses, bacteria, fungi and eukaryotic microorganisms. A "respiratory pathogen" refers to a pathogen that is capable of infecting or colonizing the respiratory tract of a host, also referred to herein as a colonizing pathogen, an indigenous pathogen, a commensal pathogen or a commensal organism. It will be understood by those skilled in the art that a pathogen can be present in a healthy subject free from infection. In the normal, healthy state, these pathogens do not cause infection while the subject does not develop respiratory symptoms. However, following a trigger (e.g., poor health, stress), the pathogen can become a causative pathogen of a chronic/acute respiratory infection.

Respiratory pathogens are known to those skilled in the art. Examples include, but are not limited to, Influenza A, Influenza B, Influenza A H1N1, Influenza A H5N1, Respiratory Syncytial Virus subtype A, Respiratory Syncytial Virus subtype B, Human Parainfluenza Virus 1, Human Parainfluenza Virus 2, Human Parainfluenza Virus 3, Human Parainfluenza Virus 4, Human Metapneumovirus, Human Adenovirus subtype B, Human Adenovirus subtype C, Human Adenovirus subtype E, Human Enterovirus, Human Rhinovirus, *Bordetella pertussis, Chlamydophila pneumoniae* and *Mycoplasma pneumoniae*, and strains thereof. Also envisaged are microbes from the genera *Streptococcus, Haemophilus, Moraxella, Pseudomonas, Klebsiella, Stenotrophomonas, Acinetobacter, Staphylococcus, Mycoplasma, Legionella, Chlamydophila, Mycobacterium, Coxiella, Nocardia, Pneumocystis, Nocardia*, and *Aspergillus*, including those listed above.

Taught herein is also a method of detecting and/or differentiating between one or more particular strains of a respiratory pathogen in a sample. Reference herein to "strains" includes any variants of the species or taxon of the analyte. Examples of "strains" of a respiratory pathogen include sub-species of the pathogen, variants of the pathogen with differing levels of virulence, variants of the pathogen that indicate different prognoses when infecting or colonizing a host, biochemical variants of the pathogen and the like.

The term "sample", as used herein, is used interchangeably with the term "analyte" to refer to any matter of composition that putatively comprises one or more respiratory pathogens. Examples include biological samples from a subject, including, but are not limited to, blood, serum, plasma, saliva, faeces, urine, lymph, amniotic fluid, cerebrospinal fluid, tissue fluid, semen, exudate, pus, respiratory fluid and mucus and swabs from topical sores, cancers and lesions and tissue or cell samples such as cell scrapes, biopsies and the like.

Samples contemplated by the method disclosed herein also include industrial samples such as air, water and soil and the like. Samples may also include ice, rock, hydrothermal vents and air; health care environments including hospitals, hospital equipment, surgical equipment, health care staff garments and the like; "industrial" environments including manufacturing facilities, pharmaceutical facilities, breweries, wineries and the like; and "laboratory" environments including fermenters, cultures, benches, equipment and the like.

As used herein, the term "subject" refers to any organism that may be susceptible to infection or colonization by a respiratory pathogen. Examples of a subject include, but are not limited to, animals, plants, fungi and bacteria (which may be infected by bacteriophage). A subject includes a host cell or a multiplicity of host cells. As used herein the term "animal" includes a mammal including a primate such as a lower primate and a higher primer including a human. However, the term "animal" also specifically includes livestock species such as cattle, horses, sheep, pigs, goats and donkeys as well as laboratory animals. Examples of laboratory test animals include mice, rats, rabbits, guinea pigs and hamsters. Rabbits and rodent animals, such as rats and mice, provide a convenient test system or animal model as do primates and lower primates. Non-mammalian animals such as avian species, zebrafish, amphibians (including cane toads) and *Drosophila* species such as *Drosophila melanogaster* are also contemplated. The subject may also be a non-animal such as a plant.

In an embodiment, the subject is human.

Respiratory infection in animals, particularly livestock species, can cause significant economic losses. For example, bovine respiratory disease (BRD), which includes upper respiratory tract infections, diphtheria and pneumonia, has been attributed to more than 60-70% of sickness and deaths in feedlot cattle. Both viral and bacterial agents can cause BRD and can be extremely difficult to control. Whilst the animals recover from the disease in most cases, they typically present with some degree of long term injury. For example, studies have shown 30-50% of all cattle showing signs of lung lesions at slaughter are the result of past respiratory disease. To control respiratory diseases in this setting, many livestock managers actively diagnose and treat outbreaks by quarantining and treated the infected animals with antibiotic and/or antiviral medications. However, these remedial efforts are typically expensive and often fail to cure the disease. Moreover, the success of treatment invariably depends on the respiratory heath of the animal prior to onset of the disease and identifying the respiratory pathogen(s) at play. Thus, the method disclosed herein has application to the livestock industry for identifying the respiratory pathogen(s) in an infected animal or population of animals, thereby allowing better diagnosis and the implementation of more effective treatment regimes.

In addition to affecting how animals respond to treatment, pathological damage arising from a previously respiratory disease can adversely impact an animal's performance at the feedlot. For instance, feedlot cattle with greater respiratory damage have been shown to gain less weight than those animals with less respiratory damage. In addition, the meat derived from cattle with greater damage is often of lower quality than the meat derived from cattle with lesser damage.

In an embodiment, the subject is a livestock animal. In a related embodiment, the respiratory pathogen is selected from a feedlot virus including, but not limited to, bovine herpesvirus 1 (BHV-1 or IBR), parainfluenza 3 virus (P13), bovine viral diarrhea virus (BVDV) and bovine respiratory syncytial virus (BRSV) and a feedlot bacterium or bacterium-like organism including, but not limited to, *Mannheimia haemolytica, Pasteurella multocida, Haemophilus somnus, Mycoplasma* spp. and *Chlamydia.*

The terms "nucleic acid", "nucleotide" and "polynucleotide" are used interchangeably herein and include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art Such modifications include, for example, labels, methylation, substitution of one or more of the naturally occurring nucleotides with an analog (such as a morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids etc.). Also included are synthetic molecules that mimic polynucleotides in their ability to bind a designated sequence via hydrogen bonding and other chemical interactions. Such molecules are known in the art and include, for example, those in which peptide linkages substitute for phosphate linkages in the backbone of the molecule.

Nucleic acids may be isolated from the subject sample using any method known to those skilled in the art. Isolation of a nucleic acid is to be understood to mean a nucleic acid that has generally been separated from other components with which it is naturally associated or linked in its native state. In an embodiment, the isolated nucleic acid is at least 50% free, or at least 75% free, or at least 90% free from other components with which it is naturally associated. The degree of isolation expressed may relate to purity from interfering substances.

DNA may be isolated from the sample using any convenient means known to the skilled addressee. For example, in the case of a virus putatively expressed in a human cell, guanidine or a functionally equivalent agent may be used to lyse the cells. In some embodiments, the DNA is purified from the sample using a limiting amount of a DNA binding agent such as, but not limited to, silica. By using a limiting amount of the DNA binding agent, a uniform amount of DNA may be isolated from different samples as the amount of DNA recovered in each case is equal to the maximum amount of DNA that can be bound by the limiting amount of DNA binding agent. The DNA bound to the DNA binding agent may then be recovered or eluted from the DNA binding agent using any convenient means.

Depending on the circumstances, which would be evident to one skilled in the art, RNA is isolated, for example, when the respiratory pathogen of interest is an RNA virus. If RNA is isolated, the RNA may be amplified, or the RNA may be reverse transcribed into cDNA using methods known to those skilled in the art, for subsequent amplification and analysis. In an embodiment, the viral RNA or corresponding DNA is isolated from an infected host cell.

The method taught herein comprises the use of specific primers to amplify a nucleic acid sequence in a sample that is highly conserved across members of the taxon of interest. Schematically, the amplified region has the general structure of:

$$C_F\text{-}X\text{—}C_R,$$

wherein:

$C_F$ is a nucleotide sequence which is conserved across members of the target taxon and is the binding site of the "forward" (F) primer;

X is a nucleotide sequence, part of which comprises a region conserved across members of the target, taxon; and $C_R$ is a nucleotide sequence which is conserved across members of the target taxon and is the binding site of the corresponding "reverse" (R) primer.

Amplification from primer sites such as those described herein effectively produces labeled nucleic acid strands (amplicons) that are then be loaded onto solid supports following hybridization to oligonucleotide capture probes immobilized to beads. In an embodiment, the labeled amplicons are loaded onto solid supports following hybridization and extension of hemi-nested probe oligonucleotides immobilized to beads.

In an embodiment, the primer pair is designed to amplify a region of nucleic acid from Influenza A. For example, the primer pair can be designed to amplify a region of the gene encoding Segment 7 of Influenza A matrix protein. In an embodiment, the primer pair comprises 5'AmMC6/CGAGGTCGAAACGTAYGTTCTYTCTAT (SEQ ID NO:1; forward primer; F) and GCCATTCCATGAGAGCCTCRAGATC (SEQ ID NO:17; reverse primer; R).

In an embodiment, the primer pair is designed to amplify a region of nucleic acid from Influenza B. For example, the primer pair can be designed to amplify a region of the gene encoding Segment 4 of Influenza B hemagglutinin. In an embodiment, the primer pair comprises 5'AmMC6/TACGGTGGATTAAACAAAAGCAAGCC (SEQ ID NO:2; forward primer; F) and CAGGAGGTCTATATTTGGTTCCATTGGC (SEQ ID NO:18; reverse primer; R).

In an embodiment, the primer pair is designed to amplify a region of nucleic acid from the 2009 H1N1 pandemic strain of Influenza A. For example, the primer pair can be designed to amplify a region of the gene encoding Segment 4 of the 2009 H1N1 pandemic strain of Influenza A. In an embodiment, the primer pair comprises 5'AmMC6/CCCAAGACAAGTTCATGGCCCAATCA (SEQ ID NO:3; forward primer; F) and GCTTTTTGCTCCAGCATGAGGACAT (SEQ ID NO:19; reverse primer; R).

In an embodiment, the primer pair is designed to amplify a region of nucleic acid from the H5N1 pandemic strain of Influenza A. For example, the primer pair can be designed to amplify a region of the gene encoding Segment 4 of the H5N1 pandemic strain of Influenza A. In an embodiment, the primer pair comprises 5'AmMC6/GCTCTGCGATCTAGATGGAGTGAAGCC (SEQ ID NO:4; forward primer; F) and YCTTCTCCACTATGTAAGACCATTCCGG (SEQ ID NO:20; reverse primer; R).

In an embodiment, the primer pair is designed to amplify a region of nucleic acid from the Respiratory Syncytial Virus (types A and B). For example, the primer pair can be designed to amplify a region of the polymerase gene of the Respiratory Syncytial Virus (types A and B). In an embodiment, the primer pair comprises 5'AmMC6/ACAGTCAGTAGTAGACCATGTGAATTC (SEQ ID NO:5; forward primer; F) and RTCRATATCTTCATCACCATACTTTTCTGTTA (SEQ ID NO:21; reverse primer; R).

In an embodiment, the primer pair is designed to amplify a region of nucleic acid from the Human Parainfluenza Virus 1. For example, the primer pair can be designed to amplify a region of the gene encoding the hemagglutinin-neuraminidase glycoprotein of Human Parainfluenza Virus 1. In an embodiment, the primer pair comprises 5'AmMC6/TGGTGATGCAATATATGCGTATTCATC (SEQ ID NO:6; forward primer; F) and CCGGGTTTAAATCAGGATACATATCTG (SEQ ID NO:22; reverse primer; R).

In an embodiment, the primer pair is designed to amplify a region of nucleic acid from the Human Parainfluenza Virus 2. For example, the primer pair can be designed to amplify a region of the gene encoding the hemagglutinin-neuraminidase glycoprotein of Human Parainfluenza Virus 2. In an embodiment, the primer pair comprises 5'AmMC6/CYCGTCCTGGAGTCATGCCATGCAA (SEQ ID NO:7; forward primer; F) and CRTTAAGCGGCCACACATCT-GCGT (SEQ ID NO:23; reverse primer; R).

In an embodiment, the primer pair is designed to amplify a region of nucleic acid from the Human Parainfluenza Virus 3. For example, the primer pair can be designed to amplify a region of the gene encoding the hemagglutinin-neuraminidase glycoprotein of Human Parainfluenza Virus 3. In an embodiment, the primer pair comprises 5'AmMC6/CAAGT-TGGCAYAGCAAGTTACAATTAGGA (SEQ ID NO:8; forward primer; F) and GTCCCCATGGACATTCATT-GTTTCCTGGT (SEQ ID NO:24; reverse primer; R).

In an embodiment, the primer pair is designed to amplify a region of nucleic acid from the Human Parainfluenza Virus 4. For example, the primer pair can be designed to amplify a region of the phosphoprotein gene of Human Parainfluenza Virus 4. In an embodiment, the primer pair comprises 5'AmMC6/GTTGATCAAGACAATACAATTACACTTGA (SEQ ID NO:9; forward primer; F) and TAAGTGCATC-TATACGAACRCCTGCTC (SEQ ID NO:25; reverse primer; R).

In an embodiment, the primer pair is designed to amplify a region of nucleic acid from the Human Metapneumovirus. For example, the primer pair can be designed to amplify a region of the gene encoding the M2 region of the matrix protein of Human Metapneumovirus. In an embodiment, the primer pair comprises 5'AmMC6/GACAAATCATMAT-GTCTCGYAARGCTCC (SEQ ID NO:10; forward primer; F) and CTATCWGGCCAACTCCAGTAATTGTG (SEQ ID NO:26; reverse primer; R).

In an embodiment, the primer, pair is designed to amplify a region of nucleic acid from Adenovirus Types B and/or E. For example, the primer pair can be designed to amplify a region of the gene encoding the Hexon region of Adenovirus Types B and E. In an embodiment, the primer pair comprises TGCCSCARTGGKCDTACATGCACATC (SEQ ID NO:11; forward primer; F) and 5'AmMC6/GCRCGGGCRAACTGCACCAG (SEQ ID NO:27; reverse primer; R).

In an embodiment, the primer pair is designed to amplify a region of nucleic acid from Adenovirus Type C. For example, the primer pair can be designed to amplify a region of the gene encoding the Hexon region of Adenovirus Types C. In an embodiment, the primer pair comprises 5'Phos/TGCCSCARTGGKCDTACATGCACATC (SEQ ID NO:12; forward primer; F) and 5'AmMC6/GCRCGGGCRAACTGCACCAG (SEQ ID NO:28; reverse primer; R).

In an embodiment, the primer pair is designed to amplify a region of nucleic acid from Human Rhinovirus/Enterovirus. For example, the primer pair can be designed to amplify the 5'UTR region of Human Rhinovirus/Enterovirus. In an embodiment, the primer pair comprises 5'AmMC6/GAAACACGGACACCCAAAGTAGT (SEQ ID NO:13; forward primer; F) and ACTCACTATAGGAGCCT-GCGTGGCKGCC (SEQ ID NO:29; reverse primer; R).

In an embodiment, the primer pair is designed to amplify a region of nucleic acid from *Bordetella pertussis*. For example, the primer pair can be designed to amplify a region of the Insertion Element (IS) 481 of *Bordetella pertussis*. In an embodiment, the primer pair comprises CCGGCCGGAT-GAACACCCATAAGCA (SEQ ID NO:14; forward primer; F) and 5'AmMC6/GGGCCGCTTCAGGCACA-CAAACTTG (SEQ ID NO:30; reverse primer; R).

In an embodiment, the primer pair is designed to amplify a region of nucleic acid from *Chlamidophila pneumoniae*. For example, the primer pair can be designed to amplify a region of the gene encoding Major Outer Membrane Protein of *Chlamidophila pneumoniae*. In an embodiment, the primer pair comprises CATGAATGGCAAGTAGGAGC-CTCTC (SEQ ID NO:15; forward primer; F) and 5'AmMC6/AGTTTTGGCTGAGCAATGCGGATGT (SEQ ID NO:31; reverse primer; R).

In an embodiment, the primer pair is designed to amplify a region of nucleic acid from *Mycoplasma pneumoniae*. For example, the primer pair can be designed to amplify a region of the gene encoding P1 Cytadhesin of *Mycoplasma pneumoniae*. In an embodiment, the primer pair comprises GAACCGAAGCGGCTTTGACCGCATC (SEQ ID NO:16; forward primer; F) and 5'AmMC6/GCGTGGGCGTTT-GCGGGTTTAACTT (SEQ ID NO:32; reverse primer; R).

The present disclosure is instructional for amplification of control sequences. In an embodiment, the control sequence may include a region of the genome of the subject from which a biological sample is derived. However, the method disclosed herein is not in any way limited to these particular control sequences and other control sequences that would be evident to one of skill in the art are also contemplated, including artificially created nucleic acid constructs comprising sequences derived from the genome of a respiratory pathogen. Furthermore, the methods disclosed herein may also be performed without the amplification of a control sequence. Where amplification of a control sequence is performed, the amplicon that is generated is also referred to herein as a "control amplicon".

In an embodiment, the primer pair is designed to amplify a region of the MYL3 gene. For example, the primer pair can comprise GCACCCAGACAATACACACAGGTGT (SEQ ID NO:33; forward primer; F) and 5'AmMC6/GGCG-GAAGTCAGCATGTGTCTG (SEQ ID NO:34; reverse primer; R).

In an embodiment, the control sequence includes a gene sequence to determine that intact RNA has been successfully isolated from a sample. For example, the primer pair can be designed to amplify a region of the Matrix MS-2 gene. In an embodiment, the primer pair comprises GCACGCTCCT-GCTACAGCCTCTTCC (SEQ ID NO:35; forward primer; F) and 5'AmMC6/CTTTTGCAGGACTTCGGTC-GACGCC (SEQ ID NO:36; reverse primer; R).

Other primer pairs and probes are those listed in Table 8 (SEQ ID NOs:74 to 126).

Isolated DNA may be amplified using any DNA amplification protocol known to those skilled in the art. A range of exemplary methods for the amplification of DNA which in no way limit the method disclosed herein are presented in "DNA Amplification: Current Technologies and Applications" (Demidov and Broude Eds. (2004) *Horizon Bioscience*). Isolated RNA may be amplified using any RNA methods known in the art and number of RNA amplification technologies have been developed. Two major categories of these are: (i) those that utilize thermal cycling such as RT-PCR and (ii) isothermal assays such as nucleic acid sequence-based amplification (NASBA) (Compton (1991) *Nature* 350:91-92; Kievits et al. (1991) *J. Virol. Methods* 35:273-286) and transcription-mediated amplification (TMA) [Hill (1996) *J. Clin. Ligand Assay* 7P:43-51]. Isothermal assays may be sub-divided, based on whether: (i) they copy and amplify the target sequence, such as TMA, NASBA and self-sustained sequence replication (3SR) [Guatelli et al. (1990) *Proc. Natl Acad. ScI USA* 57:1874-1878; Chadwick et al. (1998) *J. Virol. Methods* 70:59-70; for review see Chart and Fox (1999) *Rev. Med. Microbiol.* 70:185-196]; or (ii) they generate a target-dependent signal which can be further amplified, e.g. invader assays (Lyamichev et al. (1999) *Nat. Biotechnol.* 77:292-296; Ryan et al.

(1999) *Mol. Diagn.* 4:135-144). However, it should be understood that the method disclosed herein also contemplates any method of RNA amplification that would be evident to one of skill in the art. Furthermore, it, should be understood that the method disclosed herein also contemplates the use of reverse transcriptase or a functional equivalent thereof to convert RNA to DNA which may then be subsequently amplified.

In the method taught herein, at least one member of the primer pair comprises a detectable label, referred to herein as a "first detectable label" or "first optically detectable label", including, but not limited to, a molecule, atom or ion which emits fluorescence, phosphorescence and/or incandescence.

In an embodiment, the first optically detectable label is a "fluorescent marker" or "fluorophore". Many different fluorescent markers will be familiar to those of skill in the art, and the choice of fluorescent marker in, no way limits the method disclosed herein. Exemplary fluorescent markers comprise any fluorescent marker which is excitable using a light source selected from the group below:

(i) Argon ion lasers: comprise a blue, 488 run line, which is suitable for the excitation of many dyes and fluorochromes that fluoresce in the green to red region. Tunable argon lasers are also available that emit at a range of wavelengths (458 nm, 488 nm, 496 nm, 515 nm and others);

(ii) Diode lasers: have an emission wavelength of 635 nm. Other diode lasers which are now available operate at 532 nm. Interestingly, this wavelength excites propidium iodide (PI) optimally. PI staining is widely used for DNA analysis, live/dead counting and ploidy determination. Blue diode lasers emitting light around 476 nm are also available;

(iii) HeNe gas lasers: operate with the red 633 nm line;

(iv) HeCd lasers: operate at 325 nm;

(v) 100 W mercury arc lamp: the most efficient light source for excitation of UV dyes like Hoechst and DAPI.

Exemplary fluorophores (also referred to herein as a fluorochrome) include, but are not limited to, hydroxycoumarin, aminocoumarin, methoxyciumarin, cascade blue, Lucifer NBD, Phyccerythrin (PE), PerCP, allophycocyanin, hoechst 33342, DAP1, SYTOX Blue, hoechst 33258, chromomycin A3, mithramycin, YOYO-I, SYTOX green, SYTOX orange, 7-AAD, acridine orange, TOTO-I, To-PRO-I, thiazole orange, TOTO-3, TO-PRO-3, LDS 751, Alexa Fluor dyes including Alexa Fluoro-350, -430, -488, -532, -546, -555, -556, -594, -633, -647, -660, -680, -700 and -750; BoDipy dyes, including BoDipy 630/650 and BoDipy 650/665; CY dyes, particularly Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4',5'-dichloro-2', T-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; TRITC, Tetramethylrhodamine (TMR); Carboxytetramethylrhodamine (TAMRA); Tetrachlorofluorescein (TET); Red 6B, Fluor X, BODIPY-FL and Texas Red. In some embodiments; the first detectable label is AlexaFluor-647.

In an embodiment, at least one member of a first primer pair is labeled with a detectable label and at least one member of a second primer pair is labeled with a different detectable label so as to allow differentiation between amplicons within a set of multiple amplicons.

At least one member of a primer pair may be labeled using any convenient means known to those skilled in the art. Exemplary methods include both pre- and post-synthesis methods. Pre-synthesis labeling methods include labeling of a PCR primer that is subsequently used for amplification of, and thereby incorporated into, an amplicon via PCR. In this method, the label is typically attached to the 5' end of a primer suitable for the amplification of the amplicon, although labeling at other positions within the primer, such as 3' labeling or non-terminal labeling, is also contemplated.

A chemical linker may also be used between the label and the primer that is labeled. Exemplary linker sequences will be readily ascertained by those of skill in the art, and are likely to include linkers such as C6, C7 and C12 amino modifiers and linkers comprising thiol groups. As will be readily ascertained, a primer may comprise the linker and label, or the linker alone, to which the label may be attached at a later stage.

The method taught herein is useful in screening a sample for a multiplicity of respiratory pathogens due to its ability to have two or more subsets of beads, the beads of each subset being physiochemically distinguishable from those of another subset of the basis of bead size and, optionally, the intensity of a detectable label immobilized on the beads. Thus, the beads within any one subset may have a common optically detectable label and/or a common size. The beads within any one subset may also have a common oligonucleotide probe. Hence, multiple respiratory pathogens may be detected using a multiplicity of subsets of beads, referred to herein as a beadset.

In an embodiment, the beads comprise a "microparticle". As will be evident to those of skill in the art, almost any material, homogenous or otherwise, may be used for the microparticle. The microparticles contemplated herein may also comprise more than one substance, and as such may comprise shells, alloys or mixtures of organic and/or inorganic substances. Useful materials which may be used include materials selected from the group consisting of silica (for example: quartz or glass), latex, titania, tin dioxide, yttria, alumina, and other binary metal oxides (such as ZnO), perovskites and other piezoelectric metal oxides (such as $BaTiO_3$), ZnS, sucrose, agarose and other polymeric beads. In some embodiments, the microparticle comprises silica.

The term "physiochemically distinguishable", as used herein, refers to a measurable difference in any of bead size, the presence or absence of a particular detectable label and/or the intensity of a detectable label.

Beads contemplated for use in the method disclosed herein may be produced in any convenient regular or irregular 3-dimensional shape. However, it is generally practical to synthesize small spheres or spheroidal particles. Such spheres or spheroidal particles are also referred to herein as "beads". Accordingly, in a related embodiment, the "microparticles" are substantially spherical or spheroidal or comprise a "microsphere".

Although the beads may be referred to as "microspheres", the actual size of the beads depends on a variety of factors and the beads may or may not actually comprise measurements in the micrometer range. For example, the bead comprises a diameter (or equivalent measurement in a non-spheroidal particle) of about 300 nm to about 30 μm, including 300 nm, 350 nm, 400 nm, 450 nm, 500 nm, 550 nm, 600 nm, 650 nm, 700 nm, 750 nm, 800 nm, 850 nm, 900 $nm_5$ 950 nm, 1.0 μm, 1.1 μm, 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, 2.5 μm, 2.6 μm, 2.7 μm, 2.8 μm, 2.9 μm, 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, 5.0 μm, 5.1 μm, 5.2 μm, 5.3 μm, 5.4 μm, 5.5 μm, 5.6 μm, 5.7 μm, 5.8 μm, 6.0 μm, 6.1 μm, 6.2 μm, 6.3 $μm_5$ 6.4 μm, 6.5 μm, 6.6 μm, 6.7 μm, 6.8 μm, 6.9 μm, 7.0 μm 7.1 μm, 7.2 μm, 7.3 μm, 7.4 μm, 7.5 μm, 7.6 μm, 7.7 μm, 7.8 μm, 7.9 μm, 8.0 μm, 8.1 μm, 8.2 μm, 8.3 μm, 8.4 μm, 8.5 μm, 8.6 μm, 8.7 μm, 8.8 μm, 8.9 μm, 9.0 μm, 9.1 μm, 9.2 μm, 9.3 μm, 9.4 μm, 9.5 μm, 9.6 μm, 9.7 μm, 9.8 μm, 9.9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm and 30 μm. In some embodiments, the bead comprises a diameter (or equivalent measurement in a non-spheroidal particle) of between 3 μm and 6 μm.

In an embodiment, the beads are AmpaSand beads produced by Genera Biosystems, Victoria, Australia. However, the method described herein should not be considered in any way limited to the use of these beads specifically.

The beads may be distinguished on the basis of the presence or absence of a detectable label, referred to herein as a "second detectable labels" or "second optically detectable label" and includes, but is not limited to, any molecule, atom or ion which emits fluorescence, phosphorescence and/or incandescence. Convenient optically detectable labels include those which emit in the ultraviolet (wavelength range of about 350 nm to about 3 nm), visible (wavelength range of about 350 nm to about 800 nm, near infrared (NIR) (wavelength range of about 800 nm to about 1500 nm) and/or infrared (IR) (wavelength range of about 1500 nm to about 10 μm) ranges. However, due to the ease of detection, in some embodiments, the optically detectable label is detectable in the visible wavelength range.

The optically detectable label may comprise one or more labels selected from the group consisting of a fluorophore, a semiconductor particle, phosphor particle, a doped particle and a nanocrystal or quantum dot. In a related embodiment, the second optically detectable label is a fluorophore.

There are many fluorescent dyes that are available in the art which may be used as fluorophores in accordance with the method disclosed herein. An important property of a fluorescent dye or other fluorophore that determines its potential for use is the excitation wavelength of the fluorophore, which typically matches the available wavelength(s) of the light source. However, many different fluorescent dyes and other fluorophores will be familiar to those of skill in the art, and the choice of fluorescent marker in no way limits the method described herein. Particularly convenient fluorescent dyes which may be used for the labeling of a substrate include those discussed supra with regard to labeling of the PCR amplicon. However, when choosing a fluorescent label, the emission spectra of the fluorescent label immobilized to the bead (second detectable label) should be distinct from the emission spectrum of the detectable label used for the at least one member of the primer pair (first detectable label).

Methods of fluorescently labeling beads and microspheres would be familiar to those skilled in the art, including internal dyeing and external dyeing (surface-labeling). The two techniques produce beads with unique properties, each beneficial for different applications. Internal dyeing produces extremely stable particles with typically narrow fluorescence emissions. These beads often display a greater resistance to photobleaching. As the fluorophore is inside the beads, surface groups are available for use in conjugating ligands (proteins, antibodies, nucleic acids, etc.) to the surface of the bead. For this reason, internally labeled beads are typically used in analyte-detection and immunoassay applications. Surface-labeling involves conjugation of the fluorophore to the bead surface. Because the fluorophores are on the surface of the bead, they are able to interact with their environment just as the fluorophores on a stained cell. The result is a bead standard that exhibits the same excitation and emission properties as stained cell samples, under a variety of different conditions, such as the presence of contaminants or changes in pH. The "environmentally responsive" nature of surface-labeled beads makes them ideally suited for mimicking biological samples. Externally labeled beads are frequently used as controls and standards in a number of applications utilizing fluorescence detection. However, the method disclosed herein contemplates the association of a bead with a fluorescent label via any means.

The second optically detectable label may also be incorporated into the immobilized oligonucleotide probe, rather than being a label directly associated with the bead per se. For example, the beads comprise an immobilized "tag" or oligonucleotide probe. The tag may carry an internal amine ($NH_2$) which is then modified by conjugation with a succinimidyl ester of a dye. In some embodiments, the second detectable label is BoDipy-TMR.

By mixing labeled and unlabeled oligonucleotide probes or labels and then conjugating this mix to the beads, one can produce classes of beads with different levels of the fluorescent marker and hence second detectable label intensity.

The second detectable label may be applied to a bead at a range of concentrations or intensities, thereby providing another basis on which particular beads may be "physiochemically distinguishable". For example, if the maximum detectable intensity of the signal of a particular optically detectable is deemed to be 100%, the label may be applied to a range of beads to give intensities of 0%, 2%, 4%, 6%, 8%, 10%, 15%, 20%, 25%, 30%, 35%, 40%, 45%, 50%, 60%, 70%, 80%, 90%, 100%.

In some embodiments, the beadset comprises 6 subsets of beads of 3.0 μm, 3.5 μm, 3.8 μm, 5.0 μm, 5.2 μm and 5.7 μm in diameter (or equivalent measurement in a non-spheroidal particle) and wherein each of the 6 subsets of beads comprise a further 3 subsets (secondary subsets) comprising 1) beads conjugated to unlabeled oligonucleotide probe (TO:FLO=0; No TMR), 2) beads conjugated to a mixed 1:50-200 ratio of labeled:unlabeled oligonucleotide probe (TO:FLO=50-200; Medium TMR), respectively, and 3) beads conjugated to a mixed 1:1.5-2 ratio of labeled:unlabeled oligonucleotide probe (TO:FLO=1.5-2; High TMR), respectively.

Reference to an oligonucleotide probe that is "immobilized" to the bead is reference to an oligonucleotide attached to or otherwise associated with the bead. An oligonucleotide probe can be attached to or otherwise associated with the bead by any convenient mean known to those skilled in the art. For example, the oligonucleotide probe may be encapsulated in beads during their production or may be attached to their surface post-production. The method used to associate the oligonucleotide probe with the bead will depend on the material used, as would be readily ascertained by the skilled addressee. In addition, further treatments, including silanization (coating of the substrate with silanes), may be performed on the beads prior to attachment of the oligonucleotide probe in order to increase the binding of the probe to the bead.

Beads may be coated with any compound that will covalently attach, or otherwise adsorb, to the surface of the bead, and in addition the oligonucleotide probe could also have a chemical moiety for the attachment of an oligonucleotide probe, such as a thiol, amine or carboxyl group. Examples of compounds with these characteristics include amino-terminated silanes such as amino-propyltrimethoxysilane or amino-propyltriethoxysilane. In addition to silanes, compounds such as poly-L-lysine that non-covalently attach to the glass surface and electrostatically adsorb the phosphate groups of the polynucleotide are also within the scope of the method, disclosed herein. Therefore, other compounds, including other silanes suitable for the attachment of an oligonucleotide probe to a surface of the bead would be readily identified by the skilled person and the method disclosed herein is not limited by the choice of compound.

For example, the oligonucleotide probe can be attached to the bead by physical adsorption or chemical linking. In addition, beads may be further coated with an agent that promotes or increases the adsorption or binding of the oligonucleotide probe to the surface of the bead, such as amino-silanes. However, other agents that perform this function will be readily identified by persons of skill in the art.

For example, the oligonucleotide probe can be attached to the bead via the Universal Anchoring System (UAS) by Genera Biosystems, Victoria, Australia. Briefly, this system involves the use of a "bridge" nucleic acid molecule to ligate a nucleic acid "tag" sequence on the substrate with a target sequence. The "bridge" sequence is partially complementary to the tag sequence and partially complementary to the target sequence, such that the bridge sequence may bind to both the tag and target sequences and hold them in alignment such that the tag and target sequences may be ligated using a ligase. The UAS is also commercially available. However, the method disclosed herein should not be considered in any way limited to this particular method of linking a nucleic acid molecule to a substrate.

Determination of whether binding has occurred between an amplicon and an oligonucleotide probe may be done using any methodology known to those skilled in the art that allows localization of a bound labeled amplicon to an oligonucleotide probe immobilized to a physiochemically distinguishable bead. In an embodiment, flow cytometry is used. The method disclosed herein is, however, in no way limited to the particular flow cytometry method or apparatus.

Using flow cytometry, the size of a given bead may be determined by the light scatter of the object. For example, flow cytometry can be used to distinguish between beads of about 3.0 μm, 3.5 μm, 3.8 μm, 5.0 μm, 5.2 μm and 5.7 μm in diameter (or equivalent measurement in a non-spheroidal particle).

In addition to size detection, flow cytometers typically have one or more lasers and detectors for the detection of fluorescence. There are many fluorophores that are useful for flow cytometry, as herein described. A key property of a fluorophore that determines its potential for use in a flow cytometric assay is the excitation wavelength; that is, it must match the available wavelengths of the light source. Flow cytometers can also be used to distinguish between subsets of beads based on the intensity of fluorescence; namely, the intensity of the second detectable label. For instance, the present inventors have determined that flow cytometry is able to distinguish between beads labeled with levels of a second optically detectable label equivalent to No TMR, Medium TMR and High TMR.

In another aspect, there is provided a beadset for screening a sample for a multiplicity of respiratory pathogens to detect a particular pathogen, wherein the beadset comprises a plurality of subsets of beads wherein:

(a) the beads of each subset are homogenous with respect to size;

(b) the beads within each subset are coupled to a nucleic acid oligonucleotide probe that is capable of binding to an analyte specific region of the genome of a respiratory pathogen; and (c) optionally, the beadset comprises a subset of beads labeled with a detectable label with each subset of beads having a different detectable label intensity to create a heterogeneous mixture of beads based on the intensity of the detectable label; wherein the subset bead identity and therefore the type and/or strain of respiratory pathogen is identifiable on the basis of bead size and/or detectable label intensity.

The beadset may comprise 2, 3, 4, 5, 6, 7, 8, 10, 11, 12, 13, 14, 15, 16, 17, 18, 19, 20 or more subsets of beads, each subset comprising an oligonucleotide probe that is complementary to a region of the amplicon generated following amplification with the primer pair(s). In an embodiment, the oligonucleotide probe comprise a nucleic acid selected from the group consisting of SEQ ID NOs:37 to 54. Reference to these sequence specific oligonucleotide probes includes nucleic acid molecules having at least 90% identity to these sequences or capable of hybridizing thereto or their complementary forms under low stringency conditions. Reference to at least 90% includes 90, 91, 92, 93, 94, 95, 96, 97, 98, 99 and 100%.

The number of subsets of beads in a beadset will typically correspond to the number of analytes (i.e., types and/or strains of respiratory pathogens) to be screened. The beadset may also include one or more additional subsets for the detection of a control sequence, as herein described.

The term "oligonucleotide probe" is used herein to denote a polynucleotide immobilized to a bead (i.e., attached to or otherwise associated with the bead). Each oligonucleotide probe comprises a polynucleotide comprising a sequence that is complementary to a region of an amplicon generated in accordance with the methods described herein. An oligonucleotide probe may also comprise a sequence that is complementary to a control sequence, as herein described.

Accordingly, a beadset of oligonucleotide probes may comprise:

$$[B_1\text{-}CX_1,\ B_2\text{-}CX_2,\ B_3\text{-}cX_3,\ B_n\text{-}cX_n,\ B_y\text{-}cY,\ B_z\text{-}cZ]$$

wherein:

$B_1$, $B_n$, $B_y$, $B_z$ are each physiochemically distinguishable beads;

$cX_n$ is a polynucleotide immobilized to a bead wherein said polynucleotide comprises a nucleotide sequence which is complementary to a particular nucleic acid sequence which is specific to a particular type and/or strain of a respiratory pathogen (i.e., a type- and/or strain-specific sequence);

n is the number of respiratory pathogens or particular strains of a subject pathogen to be detected using the beadset;

cY is an optional member of the beadset and is a polynucleotide immobilized to a bead wherein said polynucleotide comprises a nucleotide sequence which is complementary to a sequence which is conserved among the pathogens or strains of a pathogen;

cZ is an optional member of the beadset and is a polynucleotide immobilized to a bead wherein said polynucleotide comprises a nucleotide sequence which is complementary to a control sequence which is amplified from a multicellular subject. In some embodiments, the control sequence is a human genomic DNA sequence. In some embodiments, the control sequence is derived from the human MYL3 gene.

The oligonucleotide probe may be attached to or otherwise associated with the beads during their production or may be attached to their surface post-production. The choice method used to associate the polynucleotide with the bead will depend on the material used, as would be readily ascertained by the skilled artisan. In addition, further treatments, including silanization (coating of the substrate with silanes), may be performed on the beads prior to attachment of the polynucleotide in order to increase the binding of said polynucleotide to the bead.

As used herein, the phrase "bound to, or otherwise associated with" refers to any process by which a molecule may be associated with a bead. Exemplary modes by which such associations may be mediated include, but are not limited to: covalent binding, hydrogen bonding, van der Waals forces, ionic bonding, metallic bonding, polar bonding and dative (covalent) bonding and the like.

A molecule including an oligonucleotide probe may also be attached to a microspheroidal particle via an agent that promotes or increases the adsorption or binding of the oligonucleotide probe to the surface of the bead, such an agent is referred to herein as a "linker". For example, polynucleotides may be associated with a microspheroidal particle via a linker which comprises a thiol, amine or carboxyl group. Examples of suitable linkers include amino-terminated silanes such as amino-propyltrimethoxysilane or amino-propyltriethoxysilane. In addition to silanes, compounds such as poly-L-lysine that non-covalently attach to surfaces such as glass and electrostatically adsorb the phosphate groups of a polynucleotide are also envisaged. Therefore, other molecules, including other silanes, which are suitable to promote the binding or association of an oligonucleotide probe to the surface of a bead would be readily identified by the skilled artisan, and the method disclosed herein is not limited by the choice of linker.

By "complementary", it is to be understood that the oligonucleotide probe should hybridize to an amplicon generated according to the methods described herein under low stringency conditions. Preferably the immobilized oligonucleotide probe should hybridize to the amplicon under medium stringency conditions, and most preferably the immobilized oligonucleotide probe should hybridize to the amplicon under high stringency conditions.

In an embodiment, where the primer pair is SEQ ID NOs:1 and 17, the complementary oligonucleotide probe is 5'ThioMC6-D/AAT/iAmMC6T/GAATTCGGATCCA-GTCTCTGCGCGATCTCGGCTTTGAG (SEQ ID NO:37).

In an embodiment, where the primer pair is SEQ ID NOs:2 and 18, the complementary oligonucleotide probe is 5ThioMC6-D/AAT/iAmMC6T/GAATTCGGATCCGGT-GTTTTCACCCATATTGGGCAATT (SEQ ID NO:38).

In an embodiment, where the primer pair is SEQ ID NOs:3 and 19, the complementary oligonucleotide probe is 5'ThioMC6-D/AAT/iAmMC6T/GAATTCGGATCCCAT-GCTGCCGTTACACCTTTGTTCG (SEQ ID NO:39).

In an embodiment, where the primer pair is SEQ ID NOs:4 and 20, the complementary oligonucleotide probe is 5'ThioMC6-D/AAT/iAmMC6T/GAATTCGGATC-CCCGAGGAGCCAT CCAGCTACACTAC (SEQ ID NO:40).

In an embodiment, where the primer pair is SEQ ID NOs:5 and 21, the complementary oligonucleotide probe is 5'ThioMC6-D/AAT/iAmMC6T/GAATTCGGATCCGTTC-TATAAGCTGGTATTGATGCAGG (SEQ ID NO:41).

In an embodiment, where the primer pair is SEQ ID NOs:6 and 22, the complementary oligonucleotide probe is 5'ThioMC6-D/AAT/iAmMC6T/GAATTCGGATC-CCCTATATCTGCACATCCTTGAGTGATT (SEQ ID NO:42).

In an embodiment, where the primer pair is SEQ ID NOs:7 and 23, the complementary oligonucleotide probe is 5'ThioMC6-D/AAT/iAmMC6T/GAATTCGGATCCAC-CCCTGTGATGCAATTAGCAGGGCA (SEQ ID NO:43).

In an embodiment, where the primer pair is SEQ ID NOs:8 and 24, the complementary oligonucleotide probe is 5'ThioMC6-D/AAT/iAmMC6T/GAATTCGGATCCAG-CACATTATGCCATGTCCATTTTATCC (SEQ ID NO:44).

In an embodiment, where the primer pair is SEQ ID NOs:9 and 25, the complementary oligonucleotide probe is 5'ThioMC6-D/AAT/iAmMC6T/GAATTCGGATCCGGT-TCCAGAYAAWATGGGTCTTGCTA (SEQ ID NO:45).

In an embodiment, where the primer pair is SEQ ID NOs:10 and 26, the complementary oligonucleotide probe is 5'ThioMC6-D/AAT/iAmMC6T/GAATTCGGATCCTTGC-CCCGYACTTCATATTTGCA (SEQ ID NO:46).

In an embodiment, where the primer pair is SEQ ID NOs:11 and 27, the complementary oligonucleotide probe is 5ThioMC6-D/AAT/iAmMC6T/GAATTCGGATCCGCT-TCGGAGTACCTGAGTCCGGGT (SEQ ID NO:47).

In an embodiment, where the primer pair is SEQ ID NOs:12 and 28, the complementary oligonucleotide probe is 5'ThioMC6-D/AAT/iAmMC6T/GAATTCGGATC-CTCGGGCCAGGACGCCTCGGAGTAC (SEQ ID NO:48).

In an embodiment, where the primer pair is SEQ ID NOs:13 and 29, the complementary oligonucleotide probe is 5'ThioMC6-D/AAT/iAmMC6T/GAATTCGGATCCTC-CTCCGGCCCCTGAATGYGGCTAA (SEQ ID NO:49).

In an embodiment, where the primer pair is SEQ ID NOs:14 and 30, the complementary oligonucleotide probe is 5ThioMC6-D/AAT/iAmMC6T/GAATTCGGATCCTGC-CCGATTGACCTTCCTACGTCGA (SEQ ID NO:50).

In an embodiment, where the primer pair is SEQ ID NOs:15 and 31, the complementary oligonucleotide probe is 5'ThioMC6-D/AAT/iAmMC6T/GAATTCGGATCCTG-GTCTCGAGCAACTTTTGATGCTG (SEQ ID NO:51).

In an embodiment, where the primer pair is SEQ ID NOs:16 and 32, the complementary oligonucleotide probe is 5'ThioMC6-D/AAT/iAmMC6T/GAATTCGGATC-CGGGCGCGCCTTATACGACCTCGATT (SEQ ID NO:52).

In an embodiment, where the primer pair is SEQ ID NOs:33 and 34, the complementary oligonucleotide probe is 5'Acryd/AAT/iAmMC6T/AAAGGGAGGACAGCTATG-GACCAAACACAGACACAGA GAGACCCACAGACA (SEQ ID NO:53).

In an embodiment, where the primer pair is SEQ ID NOs:35 and 36, the complementary oligonucleotide probe is 5'ThioMC6-D/AAT/iAmMC6T/GAATTCGGATC-CGAAGTGCCGCAGAACGTTGCGAACC (SEQ ID NO:54).

In an embodiment, the primer pairs and corresponding probes are selected from those listed in Table 8 (SEQ ID NOs:74 to 126). In an embodiment, 2 or more primer pairs and corresponding probes are selected. By "2 or more" includes from about 2 to about 18, such as 2, 3, 4, 5, 6, 7, 8, 9, 10, 11, 12, 13, 14, 15, 16, 17 or 18.

Conditions of low, medium and high stringency would be known to those skilled in the art. For example, low stringency includes from at least about 0 to at least about 15% v/v formamide (including 1%, 2%, 3%, 4%, 5%, 6%, 7%, 8%, 9%, 10% 11%, 12%, 13% and 14% v/v formamide) and from at least about 1 M to at least about 2 M salt for hybridization, and at least about 1 M to at least about 2 M salt for washing conditions. Medium stringency may include, for example, from at least about 16% v/v to at least about 30% v/v formamide, including 16%, 17%, 18%, 19%, 20%, 21%, 22%, 23%, 24%, 24%, 26%, 27%, 28%, 29% and 30% v/v formamide, and from at least about 0.5 M to at least about 0.9 M salt for hybridization, and at least about 0.5 M to at least about 0.9 M salt for washing conditions. High stringency may include, for example, from at least about 31% v/v to at least about 50% v/v formamide and from at least about 0.01 M to at least about 0.15 M salt for hybridization, and at least about 0.01 M to at least about 0.15 M salt for washing conditions. The temperature of the hybridization and wash steps may be altered and higher temperatures used to replace formamide and/or to give alternative stringency conditions.

In an embodiment, the oligonucleotide probe of a subset of beads is labeled with a second detectable label, which allows the method disclosed herein to differentiate between multiple respiratory pathogens or between multiple members of a class of respiratory pathogens. It is generally convenient to use a second detectable label that can be readily differentiated from the first detectable label, for example, on the basis of their respective wavelengths of fluorescence.

An oligonucleotide probe may be labeled with a detectable label, as herein described, using any convenient means, including those exemplified hereinbefore with respect to labeling of the strain-specific amplicon. For example, a chemical linker can be used between the label and the oligonucleotide probe which is labeled. Exemplary linker sequences will be readily ascertained by those of skill in the art, and are likely to include linkers such as C6, C7 and C12 amino modifiers and linkers comprising thiol groups. As will be readily ascertained, a primer may comprise the linker and label, or the linker alone, to which the label may be attached at a later stage. In some embodiments, the linker is a C6 amino acid modification.

In an embodiment, the label used is a quorophores (also referred to herein as a fluorochrome) selected from: hydroxycoumarin, aminocoumarin, methoxyciumarin, cascade blue, Lucifer yellow, NBD, Phyccerythrin (PE), PerCP, allophycocyanin, hoechst 33342, DAPI, SYTOX Blue, hoechst 33258, chromomycin A3, mithramycin, YOYO-I, SYTOX green, SYTOX orange, 7-AAD, acridine orange, TOTO-I, To-PRO-I, thiazole orange, TOTO-3, TO-PRO-3, LDS 751, Alexa Fluor dyes including Alexa Fluoro-350, -430, -488, -532, -546, -555, -556, -594, -633, -647, -660, -680, -700 and -750; BoDipy dyes, including BoDipy 630/650, BoDipy 650/665 and BoDipy-TMR; CY dyes, particulary Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4',5'-dichloro-2', T-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; TRITC, Tetramethylrhodamine (TMR); Carboxytetramethylrhodamine (TAMRA); Tetrachlorofluorescein (TET); Red 6B, Fluor X, BODIPY-FL and Texas Red. In some embodiments, the second detectable label is BoDipy-TMR.

In an embodiment, the oligonucleotide probe is labeled with more than one detectable label that further allow differentiation between beads within a beadset.

In an embodiment, the amount of labeled oligonucleotide probe attached to or otherwise associated with a bead within a beadset can be controlled to produce a bead with a predetermined or requisite second detectable label intensity, as hereinbefore described. Such methods are known to those skilled in the art. For example, a mixture of labeled and unlabeled oligonucleotide probes can be brought into contact with the beads, wherein ratio of labeled and unlabeled oligonucleotide probes dictates the amount of labeled oligonucleotide probe attached to or otherwise associated with a bead within a beadset, and hence the intensity of the second detectable label on each bead. The mixture of labeled and unlabeled oligonucleotide probes can be prepared, for example, using the two sequential formulae indicated below:

$$H=G*C*((E/D)-1)/F \qquad 1)$$

Where H=Vol (μL) of unlabeled stock oligonucleotide (oligonucleotide probe) required G=Vol (μL) of labeled oligonucleotide required C=Concentration of labeled oligonucleotide E=desired TO:FLO ratio D=TO:FLO ratio of stock labeled oligonucleotide F=Concentration of unlabeled stock oligonucleotide $$\text{Water}(\mu L)=(0.01*((G*C)+(H*F)))-(G+H) \qquad 2)$$

Where G=Vol (μL) of labeled oligonucleotide required

C=Concentration of labeled oligonucleotide

H=Vol (μL) of unlabeled stock oligonucleotide required [derived from 1)]

F=Concentration of unlabeled stock oligonucleotide

Thus, the beads $B_1 \ldots B_n$, $B_y$, $B_z$ of the beadsets may be physiochemically distinguishable beads. The term "physiochemically distinguishable" refers to any physical or chemical characteristic which allows one bead, e.g. $B_1$, to be differentiated from another bead, e.g. $B_2$. Accordingly, the physiochemically distinguishable beads allow differentiation of multiple respiratory pathogens or strains thereof. In accordance with the method disclosed herein, the beads of the beadset are distinguishable on the basis of size and/or second detectable label intensity. In some embodiments, the term "physiochemically distinguishable" refers to a measurable difference in any of bead size, the presence or absence of a particular optically detectable label and/or the intensity of the optically detectable label.

In an embodiment, the beads within the beadsets are distinguishable on the basis of size, the level of intensity of the second detectable label, the type of fluorophore and the sequence of the oligonucleotide probe immobilized thereon.

The present disclosure further teaches a diagnostic kit for use in accordance with the method disclosed herein, including diagnosing respiratory infection in a human subject, determining the presence of a respiratory pathogen in a sample and/or assessing the risk of a human subject developing a respiratory infection.

In an embodiment, the kit comprises a beadset comprising a subset of beads, wherein the beads within each comprise an oligonucleotide probe immobilized to the beads of a physiochemically distinguishable subset of beads, wherein the oligonucleotide probe is complementary to a nucleotide sequence of a respiratory pathogen. Optionally, the kit may comprise a primer pair capable of binding to conserved sequences among different strains of respiratory pathogens to generate an amplicon that comprises a distinct nucleotide sequence for a particular strain of respiratory pathogen, wherein the amplicon generated is putatively complementary to an oligonucleotide probe immobilized to the beads of the kit.

In an embodiment, the kit comprises at least two primer pairs comprising a forward primer selected from SEQ ID NOs:1 to 16 and SEQ ID NOs:33 and 35 and a corresponding reverse primer selected from SEQ ID NOs:17 to 32 and SEQ ID NOs:34 and 36 and at least two complementary oligonucleotide probes selected from SEQ ID NOs:37 to 54.

The specification further provides analytes detected by the method disclosed herein.

Also enabled herein is a kit comprising labeled or pre-labeled beads that may be used in the methods disclosed herein. In an embodiment, taught herein is a kit comprising two or more oligonucleotide primer pairs selected from SEQ ID NOs: 1 and 17, 2 and 18, 3 and 19, 4 and 20, 5 and 21, 6 and 22, 7 and 23, 8 and 24, 9 and 25, 10 and 26, 11 and 27, 12 and 28, 13 and 29, 14 and 30, 15 and 31 and 16 and 32 and a corresponding probe selected from SEQ ID NOs:37 to 52, respectively. In an embodiment, taught herein is a kit comprising two or more oligonucleotide primer pairs and a corresponding primer probe as listed in Table 8 (SEQ ID NOs:74 to 126). By "two or more" or "at least 2" includes from 2 to about 18 including 2, 3, 4, 5, 6, 7, 8, 9, 10, 11, 12, 13, 14, 15, 16, 17 or 18.

Aspects taught herein are further described by the following non-limiting Examples.

EXAMPLE 1

Primer Design

General considerations with respect to multiplex primer design included:

- In silico melting temperatures (T° m's) of greater than 58° C., where possible
- % GC content of 40-65%, where possible
- Avoid runs of more than 3 consecutive G's or C's
- Amplicon length minimized (to less than 150 bp where possible)

In the case of RNA targets, the AlexaFluor-labeled (5' amino modified) primer was the primer responsible for priming the cDNA synthesis from the RNA template during RT-PCR. Probe oligonucleotides were synthesized with a 5' thiol (Thio) or acrydite (AmM) modification to enable coupling to silica beads, and an internal amino modification was made to the probe oligonucleotides to allow labeling with fluorescent dye (BoDipy-TMR). Amplification primer pairs (Forward and Reverse) were designed at regions highly conserved across all strains analyzed, with particular emphasis on maximizing conservation and minimizing degeneracy at the 3' ends.

Influenza A

Target amplicon alternatives: Segment 7 (MP)

Target Gene: Segment 7 (MP)

Number of sequences analyzed: 16026

Control Construct: RTI-C2

Comments:

Sequences for Influenza A from human hosts were obtained through the Influenza Primer Design Resource (IPDR). A total of 16026 sequences of the Influenza A Matrix Protein (MP) were used to generate the consensus sequence that was then used to create a consensus sequence file in Vector NTI. Primers were designed at regions highly conserved across all strains with particular emphasis on maximizing conservation and minimizing degeneracy at the 3' ends.

Primers/Probe 1: Obsolete

| Name | Sequence | T° m | % GC | Primary Amplicon (bp) | Nested Amplicon (bp) |
|---|---|---|---|---|---|
| Am-InfA F | /5AmMC6/TRGGRTTTGTGTTCACGCTCACCGTG (SEQ ID NO: 127) | 60 | 50 | 72 | |
| P-InfA R | GGGCATTTTGGACAAAGCGTCTACGC (SEQ ID NO: 128) | 61 | 54 | | |
| AS InfA P | /5ThioMC6-D/AAT/iAmMC6T/GAATTCGGATCCTGCAGTCCTCGCTCACTGGGCA (SEQ ID NO: 129) | 62 | 64 | | 46 |

The efficiency of target amplification using Primers/Probe 1 was deemed to be too great for practical diagnostic purposes. Repeat tests confirmed that a positive InfA signal was sporadically observed in samples devoid of Influenza A input template. Due to the irregularity of these false positive results, spot contamination of the workspace environment with low amounts of Influenza A was accepted to be the likely cause. Consequently, the forward primer was re-designed (alt Am-InfA F) such that the amplicon length was increased and amplification efficiency reduced (see Primers/Probe 2, below):

Primers/Probe, 2: Obsolete

| Name | Sequence | T° m | % GC | Primary Amplicon (bp) | Nested Amplicon (bp) |
|---|---|---|---|---|---|
| alt Am-InfA F | /5AmMC6/GACAAGACCAATCCTGTCACCTCTGAC (SEQ ID NO: 130) | 59 | 52 | 110 | |
| P-InfA R | GGGCATTTTGGACAAAGCGTCTACGC (SEQ ID NO: 131) | 61 | 54 | | |
| AS InfA P | /5ThioMC6-D/AAT/iAmMC6T/GAATTCGGATCCTGCAGTCCTCGCTCACTGGGCA (SEQ ID NO: 132) | 62 | 64 | | 84 |

The use of alt Am-InfA F (Primers/Probe 2) resulted in the highly sensitive detection of Influenza A target DNA. However, false-positive results continued to be obtained under these amplification conditions. As a consequence, an alternative set of primers/probe allowing the amplification of Influenza A was designed and synthesized—Primers/Probe 3—below Primers/Probe 3:

| Name | Sequence | T° m | % GC | Primary Amplicon (bp) | Nested Amplicon (bp) |
|---|---|---|---|---|---|
| Am-InfA2 F | /5AmMC6/CGAGGTCGAAACGTAYGTTCTYTCTAT (SEQ ID NO: 1) | 58 | 48 | 122 | |
| InfA2 R | GCCATTCCATGAGAGCCTCRAGATC (SEQ ID NO: 17) | 58 | 52 | | |

-continued

Primers/Probe 3:

| Name | Sequence | T° m | % GC | Primary Amplicon (bp) | Nested Amplicon (bp) |
|---|---|---|---|---|---|
| InfA2 Pr | /5ThioMC6-D/AAT /iAmMC6T/GAATTCGGATC CAGTCTCTGCGCGATCTC GGCTTTGAG (SEQ ID NO: 37) | 63 | 58 | | 69 |

Titration of Influenza A Primers/Probe 3 resulted in amplification/labeling conditions that allowed the detection of 400 copies and even 100 copies of the synthetic Influenza A construct. Furthermore, no false-positives were observed over 3 independent experiments involving a total of 26 designated Water controls and 23 designated HeLa/MS2 controls. Furthermore, under these conditions, these primers were shown to efficiently detect the HealthScope Positive Control for InfA/H1N1.

Influenza B

Target amplicon alternatives: Segment 1 (PB2) and Segment 4 (HA)

Target Gene Segment 4 (HA)

Number of sequences analyzed: 2980

Control Construct: RTI-C3

Primers/Probe 1: Obsolete

| Name | Sequence | T° m | % GC | Primary Amplicon (bp) | Nested Amplicon (bp) |
|---|---|---|---|---|---|
| InfB F | GCACCAGGAGGACCCTAC ARAMTTGGA (SEQ ID NO: 133) | 63 | 59 | 97 | |
| InfB R | TTGGGACRGCCCAAGCCAT TGTTGCG (SEQ ID NO: 134) | 64 | 58 | | |
| InfB P | ACCTCAGGRTCTTGCCCTA ACGYTACCA (SEQ ID NO: 135) | 61 | 61 | | 70 |

In the context of the multiplex scenario, there was in general poor detection of the Influenza B control construct and confirmed Influenza B positive clinical specimens. While primary amplification appeared to be efficient (as judged by band intensity following gel electrophoresis of PCR products), loading onto beads either via hybridization following lambda Exonuclease digestion, or via a solid phase amplification procedure appeared very poor. Thus, an additional set of primers/probe was designed to allow an alternative probe sequence to be utilized (see Primers/Probe 2, below).

Primers/Probe 2:

| Name | Sequence | T° m | % GC | Primary Amplicon (bp) | Nested Amplicon (bp) |
|---|---|---|---|---|---|
| Am-InfB-2 F | /5AmMC6/TACGGTGGATT AAACAAAAGCAAGCC (SEQ ID NO: 2) | 57 | 42 | 124 | |

-continued

Primers/Probe 2:

| Name | Sequence | T° m | % GC | Primary Amplicon (bp) | Nested Amplicon (bp) |
|---|---|---|---|---|---|
| P-InfB-2 R | CAGGAGGTCTATATTTG GTTCCATTGGC (SEQ ID NO: 18) | 58 | 46 | | |
| AS InfB-2 P | /5ThioMC6-D/AAT/iAmMC6T/GAATT CGGATCCGGTGTTTTCAC CCATATTGGGCAATT (SEQ ID NO: 38) | 57 | 42 | | 64 |

Influenza A (H1N1 2009)

Target amplicon alternatives: Segment 4 (HA)

Target Gene Segment 4 (HA) of the 2009 H1N1 Pandemic strain of Influenza

Number of sequences analyzed: 4839

Control Construct: RTI-C4

Comments:

The selected primers/probe were designed to discriminate the 2009 pandemic swine flu from other swine (and human) HI subtype viruses.

| Name | Sequence | T° m | % GC | Primary Amplicon (bp) | Nested Amplicon (bp) |
|---|---|---|---|---|---|
| Am-H1N1 F | /5AmMC6/CCCAAGACAAG TTCATGGCCCAATCA (SEQ ID NO: 3) | 59 | 50 | 78 | |
| P-H1N1 R | GCTTTTTGCTCCAGCATG AGGACAT (SEQ ID NO: 19) | 58 | 48 | | |
| AS-HIN1 P | /5ThioMC6-D/AAT/iAmMC6T/GAATTC GGATCCCATGCTGCCGTT ACACCTTTGTTCG (SEQ ID NO: 39) | 59 | 55 | | 47 |

Influenza A (H5N1)

Target amplicon alternatives: Segment 4 (HA)

Target Gene Segment 4 (HA) of the H5N1 Pandemic strain of Influenza

Number of sequences analyzed: 2757

Control Construct: RTI-05

| Name | Sequence | T° m | % GC | Primary Amplicon (bp) | Nested Amplicon (bp) |
|---|---|---|---|---|---|
| Am-H5N1 F | /5AmMC6/ GCTCTGCGATCTAG ATGGAGTGAAGCC (SEQ ID NO: 4) | 61 | 56 | 128 | |
| P-H5N1 R | YCTTCTCCACTATGTAAGACC ATTCCGG (SEQ ID NO: 20) | 58 | 50 | | |
| AS -H5N1 P | /5ThioMC6-D/AAT/iAmMC6T/ GAATTCGGA TCCCCGAGGAGCCATCCAGCT ACACTAC (SEQ ID NO: 40) | 60 | 60 | | 84 |

Respiratory Syncytial Virus (Types A & B)

Target amplicon alternatives: Polymerase; Glycprotein/Fusion; Nucleoprotein

Target Gene Polymerase Gene

Number of sequences analyzed: 14

Control Construct: RTI-C18 and RTI-C19

Comments:

Highly conserved nucleoprotein and polymerase genes well suited for detection of both RSV-A and RSV-B. However, inefficient amplification using the initial primers (Primers/Probe I) targeting the nucleoprotein gene (control constructs RTI-C6 and RTI-C7) led to the re-design of primers/probe targeting the polymerase gene (control constructs RTI-C18 and RTI-C19; see Primers/Probe 2, below).

Primers/Probe 1: Nucleoprotein - Obsolete

| Name | Sequence | T° m | % GC | Primary Amplicon (bp) | Nested Amplicon (bp) |
|---|---|---|---|---|---|
| RSV F | TTGGGWGGAGAAGCWGGW TTCTACCA (SEQ ID NO: 136) | 59 | 50 | 122 | |
| RSV R | ATTATGCCTAGRCCWGCWG CATTGCC (SEQ ID NO: 137) | 62 | 54 | | |
| RSV P | ARYARTGATGCTTTTGGRTT GTTCAATAT (SEQ ID NO: 138) | 53/ 55* | 31 | | 56 |

Primers/Probe 2: Polymerase

| Name | Sequence | T° m | % GC | Primary Amplicon (bp) | Nested Amplicon (bp) |
|---|---|---|---|---|---|
| Am-RSV-3 F | /5AmMC6/ACAGTCAGTA GTAGACCATGTGAATTC (SEQ ID NO: 5) | 55 | 41 | 126 | |
| P-RSV-3 R | RTCRATATCTTCATCAC CATACTTTTCTGTTA (SEQ ID NO: 21) | 54 | 28 | | |
| AS-RSV-3 P | /5ThioMC6-D/AAT/iAmMC6T/GAATT CGGATCCGTTCTATAAG CTGGTATTGATGCAGG (SEQ ID NO: 41) | 54 | 42 | | 53 |

Human Parainfluenza Virus Type 1 (HPIV-1)

Target amplicon alternatives: HN

Target Gene: HN

Number of sequences analyzed: 30

Control Construct: RTI-C8

Comments:

While the primary amplification product using the Primers/Probe 1 sequences below appeared highly efficient from the synthetic template (as judged by gel electrophoresis), loading onto the beads and therefore solid phase detection was poor. Thus, an alternative set of Primers/Probe was designed and synthesized (Primers/Probe 2). Following primer concentration optimization, Solid Phase detection sensitivity was not dramatically enhanced using the new primers/probe set. However, Primers/Probe 2 was ultimately utilized following a direct sequence comparison of the two primer sets indicating that Primers/Probe 2 would likely detect a higher proportion of the HN database sequences analyzed.

Primers/Probe 1: Obsolete

| Name | Sequence | T° m | % GC | Primary Amplicon (bp) | Nested Amplicon (bp) |
|---|---|---|---|---|---|
| Am-Para1 F | /5AmMC6/TGGCACTC CAACCTGCAAATAGG ATCA (SEQ ID NO: 139) | 60 | 48 | 108 | |
| P-Para1 R | CCAGTTGCAGTCTTG GTTTCCTGGTCG (SEQ ID NO: 140) | 62 | 56 | | |
| AS-Para1 P | /5ThioMC6-D/AAT/iAmMC6T/GAA TTCGGATCCACAGGA CTTYATGAGGCGCCC A (SEQ ID NO: 141) | 60 | 59 | | 51 |

Primers/Probe 2:

| Name | Sequence | T° m | % GC | Primary Amplicon (bp) | Nested Amplicon (bp) |
|---|---|---|---|---|---|
| Am GB HPIV1 F | /5AmMC6/TGGTGATGCAA TATATGCGTATTCATC (SEQ ID NO: 6) | 54 | 37 | 131 | |
| P GB HPIV1 R | CCGGGTTTAAATCAGGAT ACATATCTG (SEQ ID NO: 22) | 54 | 41 | | |
| GB HPIV1 P | /5ThioMC6-D/AAT/iAmMC6T/GAATTC GGATCCCCTATATCTGCA CATCCTTGAGTGATT (SEQ ID NO: 42) | 55 | 41 | | 60 |

Human Parainfluenza Virus Type 2 (HPIV-2)

Target amplicon alternatives: FIN

Target Gene: FIN

Number of sequences analyzed: 13

Control Construct: RTI-C9

Comments:

A total of 18 sequences were aligned using the EMBL-EBI software and a highly conserved region for which there was data for 13/18 sequences was identified.

From the resulting consensus sequence, the following primers/probe sequences were identified.

| Name | Sequence | T° m | % GC | Primary Amplicon (bp) | Nested Amplicon (bp) |
|---|---|---|---|---|---|
| Am-Para2 F | /5AmMC6/CYCGTCCTGGA GTCATGCCATGCAA (SEQ ID NO: 7) | 63 | 60 | 90 | |
| P-Para2 R | CRTTAAGCGGCCACACAT CTGCGT (SEQ ID NO: 23) | 62 | 58 | | |
| AS-Para2 P | /5ThioMC6-D/AAT/iAmMC6T/GAATTC GGATCCACCCCTGTGATG CAATTAGCAGGGCA (SEq ID NO: 43) | 62 | 54 | | 52 |

Human Parainfluenza Virus Type 3 (HPIV-3)

Target amplicon alternatives: FIN

Target Gene: FIN

Number of sequences analyzed: 5 complete genome sequences and 18 HN sequences

Control Construct: RTI-C10

| Name | Sequence | T° m | % GC | Primary Amplicon (bp) | Nested Amplicon (bp) |
|---|---|---|---|---|---|
| Am-Para3 F | /5AmMC6/CAAGTTGGCAYAGCAAGTTACAATTAGGA (SEQ ID NO: 8) | 58 | 41 | 123 | |
| P-Para3 R | GTCCCCATGGACATTCATTGTTTCCTGGT (SEQ ID NO: 24) | 61 | 48 | | |
| AS-Para3 P | /5ThioMC6-D/AAT/iAmMC6T/GAATTCGGATCCAGCACATTATGCCATGTCCATTTTATCC (SEq ID NO: 44) | 56 | 39 | | 63 |

Human Parainfluenza Virus Type 4 (HPIV-4)

Target amplicon alternatives: Phosphoprotein (P) gene

Target Gene: P gene

Number of sequences analyzed: 40

Control Construct: RTI-C11

Comments:

Alignment of 40 sequences of 4a (22) and 4b (18) phosphoprotein genes with the only complete genome sequence in the NCBI database (HPIV 4b; Accession number EU627591) using the EMBL-EBI software resulted in a consensus sequence that could be used to design primers/probe.

| Name | Sequence | T° m | % GC | Primary Amplicon (bp) | Nested Amplicon (bp) |
|---|---|---|---|---|---|
| Am-Para4 F | /5AmMC6/GTTGATCAAGACAATACAATTACACTTGA (SEQ ID NO: 9) | 53 | 31 | 109 | |
| P-Para4 R | TAAGTGCATCTATACGAACRCCTGCTC (SEQ ID NO: 25) | 59* | 46* | | |
| AS-Para4 P | /5ThioMC6-D/AAT/iAmMC6T/GAATTCGGATCCGGTTCCAGAYAAWATGGGTCTTGCTA (SEq ID NO: 45) | 59* | 44* | | 75 |

*Based on EU627591

Human Metapneumovirus (hMPV)

Target amplicon alternatives: Nucleoprotein (N), Matrix (M)

Target Gene: M2 region of Matrix

Number of sequences analyzed: 74

Control Construct: RTI-C12

Comments:

A consensus sequence of the M2 gene was initially made from alignments of 12 complete genome sequences using software at EMBL-EBI, and from this primers/probe was designed. These primers were then checked against Contig 4 of the Matrix and NC_004148 assembly that assembled all hMPV matrix sequences with the hMPV reference sequence (NC_004148).

| Name | Sequence | T° m | % GC | Primary Amplicon (bp) | Nested Amplicon (bp) |
|---|---|---|---|---|---|
| Am-hMPV F | /5AmMC6/GACAAATCATMATGTCTCGYAARGCTCC (SEQ ID NO: 10) | 58 | 45 | 109 | |
| P-hMPV R | CTATCWGGCCAACTCCAGTAATTGTG (SEQ ID NO: 26) | 56 | 46 | | |
| AS-hMPV P | /5ThioMC6-D/AAT/iAmMC6T/GAATTCGGATCCTTGCCCCGYACTTCATATTTGCA (SEQ ID NO: 46) | 58 | 46 | | 80 |

Adenovirus (Types B, C and E) (AdV)

Target amplicon alternatives: Hexon

Target Gene Hexon

Number of sequences analyzed: 247 Hexon sequences and 15 complete genome sequences Control Construct: RTI-C13

| Name | Sequence | T° m | % GC | Primary Amplicon (bp) | Nested Amplicon (bp) |
|---|---|---|---|---|---|
| P-AdV F | TGCCSCARTGGKCDTACATGCACATC (SEQ ID NO: 11/12) | 62 | 54 | 82 | |

-continued

| Name | Sequence | T° m | % GC | Primary Amplicon (bp) | Nested Amplicon (bp) |
|---|---|---|---|---|---|
| AdV R | /5AmMC6/GCRCGGGCRAACTGCACCAG (SEQ ID NO: 27/28) | 64 | 70 | | |

-continued

| Name | Sequence | T° m | % GC | Primary Amplicon (bp) | Nested Amplicon (bp) |
|---|---|---|---|---|---|
| AdV B/E P | /5ThioMC6-D/AAT/iAmMC6T/GAATTCGG ATCCGCTTCGGAGTACCTGA GTCCGGGT (SEq ID NO: 47) | 63* | 63 | | 44 |
| AdV C P | /5ThioMC6-D/AAT/iAmMC6T/GAATTCGG ATCCTCGGGCCAGGACGCC TCGGAGTAC (SEQ ID NO: 48) | 64* | 63 | | 56 |

*calculated in Vector NTI

Rhinovirus/Enterovirus (RhV)

Target amplicon alternatives: 5'UTR (untranslated region)

Target Amplicon: 5'UTR

Number of sequences analyzed: 962 5'UTR sequences and 138 complete genome sequences Control Construct: RTI-C14

*Chlamidophila pneumoniae* (Cpn)

Target amplicon alternatives: MOMP

Target Gene: MOMP

Number of sequences analyzed: 19

Control Construct: RTI-C16

Comments:

primers/probe located within a highly conserved region of the Major Outer Membrane Protein (MOMP).

| Name | Sequence | T° m | % GC | Primary Amplicon (bp) | Nested Amplicon (bp) |
|---|---|---|---|---|---|
| P-Cpn F | CATGAATGGCAAGTAGGAGC CTCTC (SEQ ID NO: 15) | 57 | 52 | 122 | |
| Cpn R | /5AmMC6/AGTTTTGGCTGAGC AATGCGGATGT (SEQ ID NO: 31) | 60 | 48 | | |
| Cpn P | /5ThioMC6-D/AAT/iAmMC6T/GAATTCGGA TCCTGGTCTCGAGCAACTTTT GATGCTG (SEQ ID NO: 51) | 58 | 48 | | 53 |

| Name | Sequence | T° m* | % GC | Primary Amplicon (bp) | Nested Amplicon (bp) |
|---|---|---|---|---|---|
| truncRhi R | /5AmMC6/GAAACACGGAC ACCCAAAGTAGT (SEQ ID NO: 13) | 54 | 48 | 209 | |
| P-T7truncRhi F | ACTCACTATAGGAGCCTG CGTGGCKGCC (SEQ ID NO: 29) | 55 | 75 | | |
| Rhi P | /5ThioMC6-D/AAT/iAmMC6T/GAATTC GGATCCTCCTCCGGCCCC TGAATGYGGCTAA (SEQ ID NO: 49) | 69 | 60 | | 120 |

*Bordetella pertussis* (Beer)

Target amplicon alternatives: IS481; ptx

Target Gene Segment 4 (HA)

Number of sequences analyzed: 2980

Control Construct: RTI-C15

| Name | Sequence | T° m | % GC | Primary Amplicon (bp) | Nested Amplicon (bp) |
|---|---|---|---|---|---|
| P-Bper F | CCGGCCGGATGAACACCCA TAAGCA (SEQ ID NO: 14) | 63 | 60 | 105 | |
| Bper R | /5AmMC6/GGGCCGCTTCAGG CACACAAACTTG (SEQ ID NO: 30) | 63 | 60 | | |
| Bper P | /5ThioMC6-D/AAT/iAmMC6T/GAATTCGG ATCCTGCCCGATTGACCTTC CTACGTCGA (SEQ ID NO: 50) | 61 | 56 | | 80 |

*Mycoplasma pneumoniae* (Mpneu)

Target amplicon alternatives: P1 Cytadhesin, 16s rRNA and ATPase

Target Gene: P1 Cytadhesin

Number of sequences analyzed: 212

Control Construct: RTI-C17

Comments:

Consensus was finally derived from 5 sequences from a highly conserved region of the P1 cytadhesin gene.

| Name | Sequence | T° m | % GC | Primary Amplicon (bp) | Nested Amplicon (bp) |
|---|---|---|---|---|---|
| P-Mpneu F | GAACCGAAGCGGCTTTGACCG CATC (SEQ ID NO: 16) | 63 | 60 | 114 | |
| Mpneu R | /5AmMC6/GCGTGGGCGTTTGC GGGTTTAACTT (SEQ ID NO: 32) | 63 | 56 | | |

-continued

| Name | Sequence | T° m | % GC | Primary Amplicon (bp) | Nested Amplicon (bp) |
|---|---|---|---|---|---|
| Mpneu P | /5ThioMC6-D/AAT/iAmMC6T/GAATTCGGA TCCGGGCGCGCCTTATACGAC CTCGATT (SEQ ID NO: 52) | 63 | 60 | | 55 |

MS-2 phage (MS-2)

Target amplicon alternatives: Matrix

Target Gene Matrix

Number of sequences analyzed: 2 complete genomes

Control Construct: RTI-C1

Comments:

The MS-2 control was used to determine that in-tact RNA has been successfully extracted using the recommended nucleic acid purification procedure. Purified MS2 RNA was added to reaction tubes immediately after addition of the lysis solution within the nucleic acid extraction/purification procedure.

| Name | Sequence | T° m | % GC | Primary Amplicon (bp) | Nested Amplicon (bp) |
|---|---|---|---|---|---|
| P-MS2-2 F | GCACGCTCCTGCTACAGC CTCTTCC (SEQ ID NO: 35) | 63 | 64 | 102 | |
| MS2-2 R | /5AmMC6/CTTTTGCAGGA CTTCGGTCGACGCC (SEQ ID NO: 36) | 62 | 60 | | |
| MS2-2 P | /5ThioMC6-D/AAT/iAmMC6T/GAATTC GGATCCGAAGTGCCGCAG AACGTTGCGAACC (SEQ ID NO: 54) | 63 | 60 | | 51 |

Human

Target amplicon alternatives: MYL3, β-actin

Target Gene: MYL3

Number of sequences analyzed: 1

Control: RNase free HeLa genomic preparation (Qiagen)

Comments:

The purpose of this internal control was to establish adequate specimen amount and integrity. The MYL3 gene is a single copy gene that is expressed primarily in cardiac tissue. In contrast, the β-actin gene has multiple copies and pseudogenes, and is highly expressed in all tissues.

| Name | Sequence | T° m* | % GC | Primary Amplicon (bp) | Nested Amplicon (bp) |
|---|---|---|---|---|---|
| P-MYL3 F | GCACCCAGACAATACACA CAGGTGT (SEQ ID NO: 33) | 59 | 52 | 131 | |
| MYL3 R | /5AmMC6/ GGCGGAAGTCAG CATGTGTCTG (SEQ ID NO: 34) | 59 | 59 | | |

-continued

| Name | Sequence | T° m* | % GC | Primary Amplicon (bp) | Nested Amplicon (bp) |
|---|---|---|---|---|---|
| PapType ProbeML C_Int Oligo | /5Acryd/AAT/ iAmMC6T/AAA GGGAGGACAGCTATGGAC CAAACACAGACACAGAGA GACCCACAGACA (SEQ ID NO: 53) | 64 | 58 | | 87 |

*calculated on Vector NTI

EXAMPLE 2

Unlabeled Oligonucleotide Preparation

All oligonucleotides were ordered desalted from Integrated DNA Technologies (IDT). Following 3 rounds of ethanol precipitation, primers were dissolved in water such that a theoretical concentration of approximately 400 μM was achieved based on the datasheet provided by IDT.

Unlabeled probe oligonucleotides were ordered desalted from IDT and following 3 rounds of ethanol precipitation were dissolved in water such that a theoretical concentration of approximately 400 μM was achieved based on the datasheet provided by IDT. Unlabeled stock oligonucleotides were stored at −20° C.

EXAMPLE 3

Oligonucleotide Labeling with Bodipy-TMR and AlexaFluor647

Primer and probe oligonucleotides synthesized with an amine modification at the C6 position of an internal thymidine nucleotide were labeled overnight with a 15-fold molar excess of the succinimidyl ester of the appropriate dye (Invitrogen) in the presence of 0.1 M Carbonate Buffer pH 9.0. Oligonucleotides were then subjected to 3 rounds of ethanol precipitation to remove unconjugated dye and adjusted with unlabeled (but otherwise identical) oligonucleotides to achieve desired labeled to unlabeled oligonucleotide ratios. The final concentration and TO:FLO of labeled oligonucleotides was adjusted using the formulae below:

$$V0=V2\times C2\times((TF1/TF0)-1)/C0$$

$$Vw=(1/Ct\times((V2\times C2)+(V0\times C0)))-(V2+V0)$$

Where:

V0 Unlabeled oligo required to add

V2 Volume of Labeled oligo to be used for adjustment

C2 Conc. Of Labeled oligo to be used for adjustment

TF1 Target TO:FLO

TF0 Initial TO:FLO

C0 Conc. Of Unlabeled oligo

Vw Volume of water required to add.

Ct Target conc.

In general, for labeled primer oligonucleotides, the ratio of labeled to unlabeled oligonucleotide was 1:1.8. For labeled probe oligonucleotides designed to be conjugated to the high TMR and medium TMR beads, the ratio of labeled to unlabeled oligonucleotide was 1:2 and 1:100, respectively. TO:FLO adjusted labeled primer oligonucleotides were stored at −20° C.

EXAMPLE 4

Bead Silanization, Probe Coupling and Bead Pooling

A volume of 5 μL of bead mix prepared in this way was used per RT-PCR reaction. Silica beads (Bangs Laboratories Inc.) were washed 3 times in water and pelleted beads were then treated with 1.55M $HNO_3$ for 30 min at room temperature. Beads were then washed 5 times in water and 3 times in Isopropanol. In a round bottomed flask, approximately $1\times10^9$ beads in 95 mL Isopropanol were then brought to the boil and 0.5 mL water and 5 mL of freshly opened 3-mercaptopropyl trimethoxysilane (3 MPTS; Sigma) added. Silanization was carried out for 23-25 h under reflux after which beads were washed 3 times in Isopropanol and dried at 45° C. for 40 min in a vacuum concentrator. Dried beads were then heat cured for 16-24 h at 105° C. before being stored at room temperature under Argon gas. For probe oligonucleotide coupling, silanized beads were weighed and resuspended in 0.1M MES buffer (Sigma Aldrich) adjusted to pH 4.75 and then coupled to probe oligonucleotides (IDT) via a 5'-Acrydite (Trade Mark) modification in the presence of 1% w/v ammonium persulfate (APS) before being washed and then resuspended in Acquisition Buffer (10 mM Tris-C1, 0.5 mM EDTA, 0.0125% w/v $NaN_3$, 0.01% v/v Triton X-100). Individual bead solutions were then counted in a Z1 Coulter Particle Counter (Beckman Coulter) and adjusted to $2.1\times10^7$ beads/mL before being pooled in equimolar ratios and adjusted to a final concentration of $1.26\times10^7$ beads/mL. Specifically, bead pooling was performed by mixing equal proportions of each (18) coupled bead populations at $2.1\times10^7$ beads/mL followed by the addition of Acquisition Buffer equivalent to ⅔ the volume of the mixed beads. See Table 3.

For Example: Pooling 10 μL of each bead

18×10 μL individual beads=1804

Add ⅔×1804=1204 of Acquisition Buffer

Final Volume=180 μL+120 μL=300 μL beadpool

A volume of 5 μL of bead mix prepared in this way was used per RT-PCR reaction. It should also be noted that initial experiments involved the resuspension of pooled beads in a buffer similar to Acquisition Buffer but with reduced Triton X-100 (0.001% v/v Triton X-100). Subsequent experimental data (nv3pg8) showed equivalent results were obtained when beads were pooled in either Acquisition Buffer or the Acquisition Buffer with reduced Triton X-100 (0.001% v/v Triton X-100). Thus, for convenience and manufacturing processes more in line current protocols, beadpools were ultimately assembled in Acquisition Buffer.

Once a primer pair was decided upon, the control construct was then designed. Control constructs were obtained from GenScript in 100 ug lyophilized form in which a synthetically made DNA insert of approximately 500 bp was blunt cloned into polylinker of the in-house vector pUC57. In general, the synthetically made DNA inserts were designed with the following key features:

1) 5' T7 and T3 promoters for efficient in vitro transcription;

2) Target amplicon plus >20 bp or flanking sequence;

3) Alternative amplicons (e.g. HealthScope or other literature) with >20 bp of flanking sequence;

4) 3' Not I restriction site for linearization of template allowing transcription termination (ensuring that no internal Not I sites are present in the pathogen sequences).

TABLE 3

Volumes of 100 μM Probe Oligonucleotide Required/mg of Beads

| Probe oligo ID | Sequence | Bead Size (um) | TO: FLO | Vol (ul) or 100 uM oligo per mg beads |
|---|---|---|---|---|
| InfA2 Pr | /5ThioMC6-D/AAT/iAmMC6T/GAATTCGGATCC AGTCTCTGCGCGATCTCGGCTTTGAG | 5.66 | na | 17.5 |
| AS InfB-2 P | /5ThioMC6-D/AAT/iAmMC6T/GAATTCGGATCC GGTGTTTTCACCCATATTGGGCAATT | 5.20 | 120.00 | 34 |
| AS-H1N1 P | /5ThioMC6-D/AAT/iAmMC6T/GAATTCGGATCC CATGCTGCCGTTACACCTTTGTTCG | 3.00 | na | 73 |
| AS-H5N1 P | /5ThioMC6-D/AAT/iAmMC6T/GAATTCGGATCC CCGAGGAGCCATCCAGCTACACTAC | 5.01 | na | 34 |
| AS-RSV-3 P | /5ThioMC6-D/AAT/iAmMC6T/GAATTCGGATCC GTTCTATAAGCTGGTATTGATGCAGG | 3.77 | na | 72 |
| GB HPIV1 P | /5ThioMC6-D/AAT/iAmMC6T/GAATTCGGATCC CCTATATCTGCACATCCTTGAGTGATT | 3.77 | 2.00 | 72 |
| AS-Para2 P | /5ThioMC6-D/AAT/iAmMC6T/GAATTCGGATCC ACCCCTGTGATGCAATTAGCAGGGCA | 3.49 | 2.00 | 53 |
| AS-Para3 P | /5ThioMC6-D/AAT/iAmMC6T/GAATTCGGATCC AGCACATTATGCCATGTCCATTTTATCC | 3.00 | 2.00 | 73 |

TABLE 3-continued

Volumes of 100 μM Probe Oligonucleotide Required/mg of Beads

| Probe oligo ID | Sequence | Bead Size (um) | TO: FLO | Vol (ul) or 100 uM oligo per mg beads |
|---|---|---|---|---|
| AS-Para4 P | /5ThioMC6-D/AAT/iAmMC6T/GAATTCGGATCC GGTTCCAGAYAAWATGGGTCTTGCTA | 5.66 | 80.00 | 17.5 |
| AS-hMPV P | /5ThioMC6-D/AAT/iAmMC6T/GAATTCGGATCC TTGCCCCGYACTTCATATTTGCA | 3.77 | 75.00 | 72 |
| AdV B/E P | /5ThioMC6-D/AAT/iAmMC6T/GAATTCGGATCC GCTTCGGAGTACCTGAGTCCGGGT | 5.20 | na | 34 |
| AdV C P | /5ThioMC6-D/AAT/iAmMC6T/GAATTCGGATCC TCGGGCCAGGACGCCTCGGAGTAC | 5.20 | na | 34 |
| Rhi P | /5ThioMC6-D/AAT/iAmMC6T/GAATTCGGATCC TCCTCCGGCCCCTGAATGYGGCTAA | 5.01 | 100.00 | 34 |
| Bper P | /5ThioMC6-D/AAT/iAmMC6T/GAATTCGGATCC TGCCCGATTGACCTTCCTACGTCGA | 5.66 | 2.00 | 17.5 |
| Cpn P | /5ThioMC6-D/AAT/iAmMC6T/GAATTCGGATCC TGGTCTCGAGCAACTTTTGATGCTG | 5.20 | 1.50 | 34 |
| Mpneu P | /5ThioMC6-D/AAT/iAmMC6T/GAATTCGGATCC GGGCGCGCCTTATACGACCTCGATT | 5.01 | 2.00 | 34 |
| MS2-2 P | /5ThioMC6-D/AAT/iAmMC6T/GAATTCGGATCC GAAGTGCCGCAGAACGTTGCGAACC | 3.49 | na | 53 |
| PapType ProbeMLC Int Oligo | /5Acryd/AAT/iAmMC6T/AAAGGGAGGACAGCTATGGACCAAACACAGACACAGAGAGACCCACAGACA | 3.49 | 100.00 | 53 |

EXAMPLE 5

Control Construct Design and Construction

For the RNA viruses, particular care was taken to ensure that upon RNA transcription of the insert, the correct (genomic) sense RNA was produced.

All control constructs were designed and saved in Vector-NTI for record purposes. Hard copies of the vector diagrams were archived. The sequences as submitted to GenScript are given in FIG. 1. It should be noted that due to a necessary primer/probe re-design for respiratory syncytial virus, additional control constructs were designed and synthesized for this pathogen. Control constructs RTI-C18 and RTI-C19 encompassing portions of the RSV Polymerase gene are those templates targeted by the final RSV primers/probe.

In vitro transcription using the synthetic control construct templates was performed using the Ambion Megascript kit according to the manufacturer's instructions. Briefly, lyophilized DNA templates were dissolved in RNase free water to approximately 1 μg/μl and 10 μg linearized with the restriction enzyme Not I for 2 hours at 37° C. in 1×NEBuffer 3+BSA. Reactions were then heat inactivated for 20 min at 65° C. and the nucleic acid purified using the Qiagen gel extraction kit according to the manufacturer's instructions. DNA eluted into 100 μl of nuclease free water was then subjected to ethanol precipitation with the final DNA pellet dissolved in 12 μl of nuclease free water. An aliquot of each DNA sample was then quantified using the spectrophotometer.

In vitro transcription was performed on 1 μg of the freshly prepared DNA templates and allowed to proceed for 3 h and 30 min at 37° C. in the thermocycler. 1 μL of Turbo DNase was then added and reactions incubated for a further 15 min at 37° C. to remove all traces of the input DNA template. RNA was recovered using the RNeasy kit as per manufacturer's instructions and eluted in 50 μL of RNA Storage Solution (Ambion). RNA was quantified in triplicate using the spectrophotometer and RNA integrity and concentration confirmed by denaturing agarose gel electrophoresis. The identity of the transcribed RNA was confirmed by PCR with primers designed to amplify specific internal sequences (see FIG. 2).

In general, aliquots of the RNA stock solutions were diluted to $1\times10^9$ copies/μL in RNA Storage Solution (Ambion) and stored at −20° C. until required. Optimization of the assay was routinely performed on known amounts of RNA freshly diluted from the $1\times10^9$ copies/μL stock tubes.

No obvious degradation of the RNA stocks (stored in RNA Storage Buffer) was observed after 1 month storage at −20° C. as determined by denaturing agarose gel electrophoresis and spectrophotometry.

EXAMPLE 6

Solid Phase RT-PCR

One Step RT-PCRs were set up essentially according to the manufacturer's instructions (Qiagen). Briefly, 10 μL of a master mix containing 1× reaction buffer, dNTPs, oligonucleotides (see body text for oligonucleotide sequences) and enzyme mix were added to 5 μL of preplated beads. Sample (10 μL) was then added and plates sealed and spun at 300×g for 1 min. Trays were then subjected to incubations of 50° C. for 20 min and 95° C. for 15 min before being cycled (45 cycles) as follows: 95° C. for 30 sec, 60° C. 30 sec and 72° C. for 1 min. A final extension step of 2 min at 72° C. was included prior to initiating an hybridization profile that involved an initial incubation of 90° C. for 30 sec and then the stepwise reduction of incubation temperature by 1° C. every 15 sec for 65 cycles such that a final temperature of 25° C. was achieved.

EXAMPLE 7

Data Acquisition and Analysis

Following Solid Phase RT-PCR cycling, plates were spun for 1 min at 1000×g and pelleted beads washed 5 times in 1204 of Sheath Buffer (8 mM NaCl, 0.0001% v/v Triton X-100) with a spin at 300×g for 1 min between addition of wash buffer to pellet beads. Alternatively, plate washes were performed in a Hydrospeed platewasher (Tecan) allowing a 5 min bead settling time between cycles of gentle aspiration and dispense. Beads were finally resuspended in 80 μL to 1204 of Sheath Buffer prior to analysis on the FACSArray Flow Cytometer (BD Biosciences). Data exported as FCS 2.0 files was then analyzed using either FCS Express (De Novo Software) or customized analysis software (Genera Biosystems).

EXAMPLE 8

PCR Optimization

Annealing Temperature I. Flanking Primers (Internal Probe Oligonucleotide Absent)

The annealing temperatures for primer pairs that allowed efficient PCR amplification of target templates was initially determined using gradient PCRs and HotStar Taq in Qiagen RT-PCR buffer. PCRs were performed on 10000 copies of the target template (104 of 1000 copies/4). To ensure a broad range of annealing temperatures would be assessed a gradient of annealing temperatures from 52-70° C. was used. This translated to temperatures of 51.8° C., 52.2° C., 53.3° C., 55.0° C., 57.1° C., 59.5° C., 61.9° C., 64.3° C., 66.5° C., 68.2° C., 69.5° C. and 70.0° C. across wells within each row of the Eppendorf Mastercycler Ep S used in this experiment. PCRs were cycled as follows: 95° C. 15 min and then 40 cycles of 95° C. 30 sec, grad 52-70° C. 30 sec, 72° C. 30 sec with a final extension of 10 min.

In all cases, 5 μL of PCR product was run down a 2.5% TAE Agarose gel (run at 150V) and DNA was visualized on a UV transilluminator following staining in SYBR-safe dye (Invitrogen) for 20 min at a final 2× concentration. The annealing temperature resulting in efficient PCR amplification (as judged by band intensity) for each primer set was then determined and is shown below in Table 4, below:

TABLE 4

Annealing Temperatures for First-Generation Primers

| Pathogen | T° anneal |
|---|---|
| Influenza A* | 61.9 |
| Influenza B* | 64.3 |
| Influenza A H1N1 | 61.9 |
| Influenza A H5N1 | 66.5 |
| RSV-A* | 61.9 |
| RSV-B* | 64.3 |
| Parainfluenza 1 | 61.9 |
| Parainfluenza 2 | 66.5 |
| Parainfluenza 3 | 61.9 |
| Parainfluenza 4 | 61.9 |
| Metapneumovirus | 59.5 |
| Adenovirus | 61.9 |
| Rhinovirus* | 64.3 |
| *B. pertussis* | 61.9 |
| *C. pneumoniae* | 64.3 |
| *M. pneumoniae* | 61.9 |
| MS2 Phage* | 70 |

*results obtained on early primer pairs that are different to those used in the final assay.

Consistent with the in silico predictions, the annealing temperatures allowing maximal amplification of target templates was generally high (>59° C.) and varied from 59.5° C. to 70° C. An annealing temperature of 60° C. allowed for the efficient amplification of all targets and was therefore initially selected as the annealing temperature for the solid phase RT-PCR component of the assay. It should be reiterated that some of this data was derived from first-generation primer pairs not used in the final assay.

Multiplex PCRs: DNA Template; No Background DNA

Figure 3:
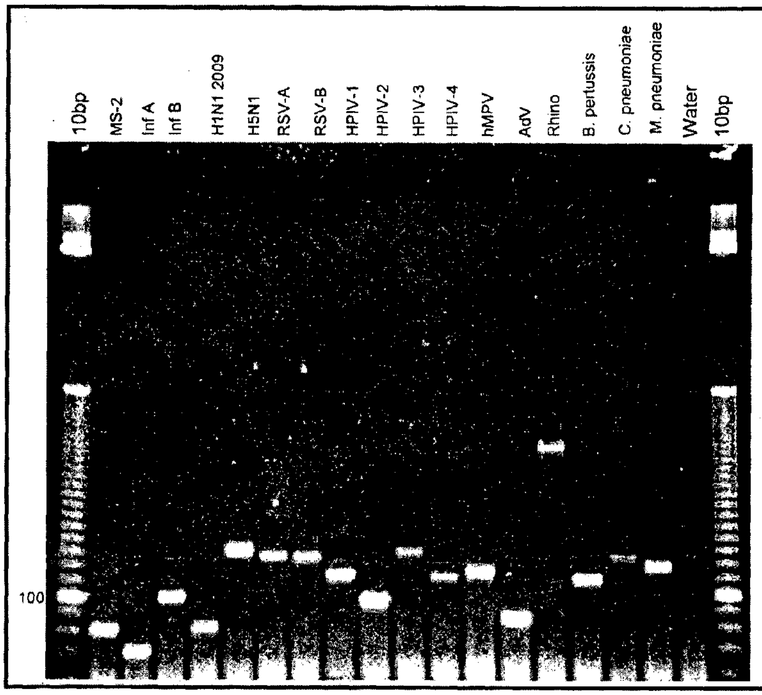
FIG. 3 is a photographical representation showing primer concentrations resulting in efficient amplification of all target DNA templates.

PCR reactions (in the absence of reverse transcription) using DNA templates were initially conducted with a primer mix containing 0.6 μM (final) concentration of each primer (as recommended by the manufacturer for use with the Qiagen One-step RT-PCR kit). Under these conditions, all targets were amplified as judged by visualizing bands following PAGE electrophoresis for 4 h at 100V through 15% w/v TBE pre-cast gels (Biorad). Poor amplification was reproducibly noted for RSV-A, hMPV and RhV. Subsequent experiments in which primer-pair concentrations within the primer mix were modulated identified primer mixes that facilitated the efficient amplification of all target analytes (see FIG. 3).

Multiplex RT-PCRs: RNA Template+/−Background DNA

Using primer concentrations established in DNA template experiments, initial RT-PCRs on 10000 copies of RNA targets showed inefficient amplification of a variety of target analytes, including MS2, RSV-A, Para3, Para4, hMPV, AdV and RhV. Optimization experiments modulating the duration (20 min vs 30 min) and temperature (40° C. vs 45° C. vs 50 vs 55 vs 60) of the RT step did not results in more efficient amplification of target templates as judged by PAGE analysis. Thus, the manufacturer's recommendation of 50° C. for 20 min was used for all subsequent reverse transcription steps.

Figure 4:
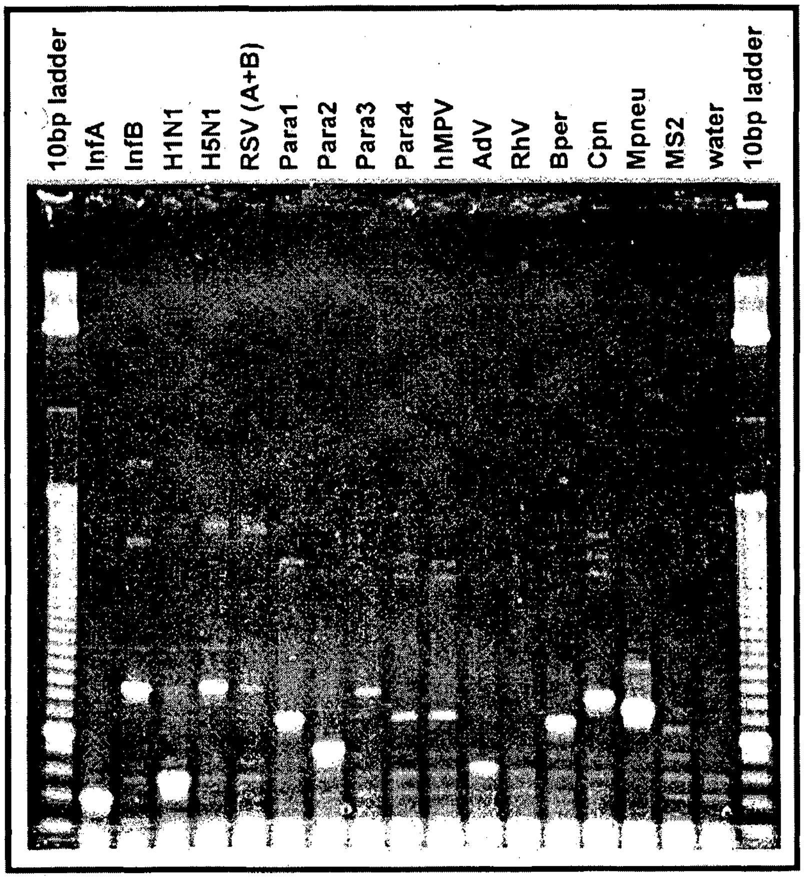
FIG. 4 is a photographical representation showing primer conditions resulting in efficient amplification of RNA and DNA templates.

Experiments in which primer-pair concentrations within the primer mix were modulated, and primers/probe combinations were redesigned for MS2 and RSV identified primer mixes that facilitated the visible amplification (by polyacrylamide gel electrophoresis) of all target analytes except RhV (see FIG. 4).

Figure 5A:
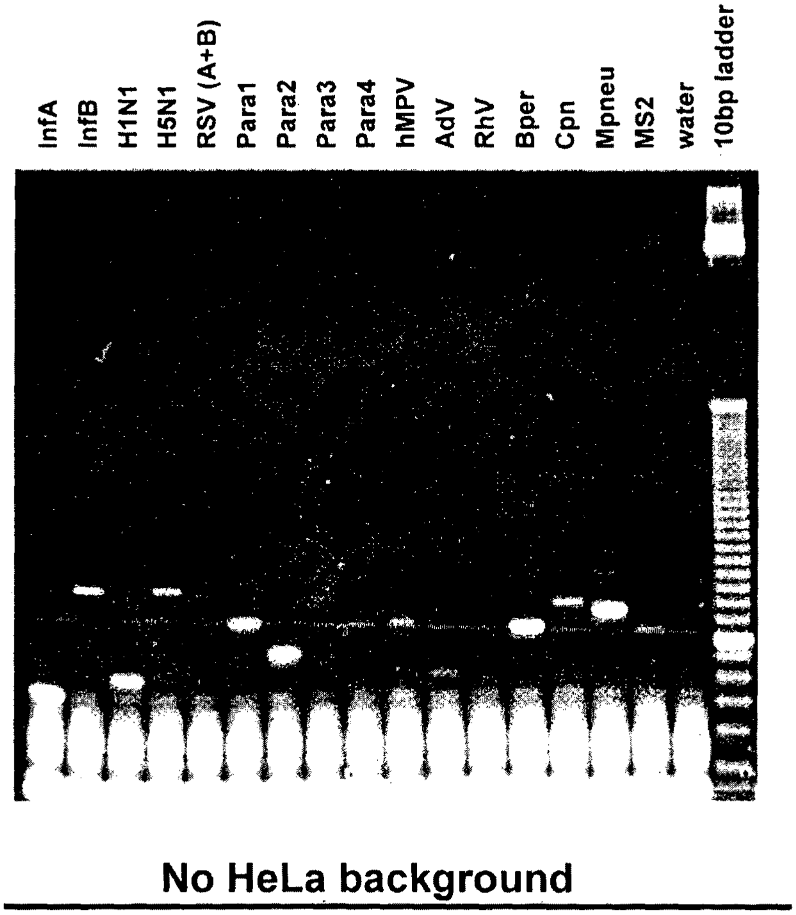
FIGS. 5A and B are photographical representations showing RT-PCR amplification profiles in the absence or presence of background human chromosomal DNA.
Figure 5B:
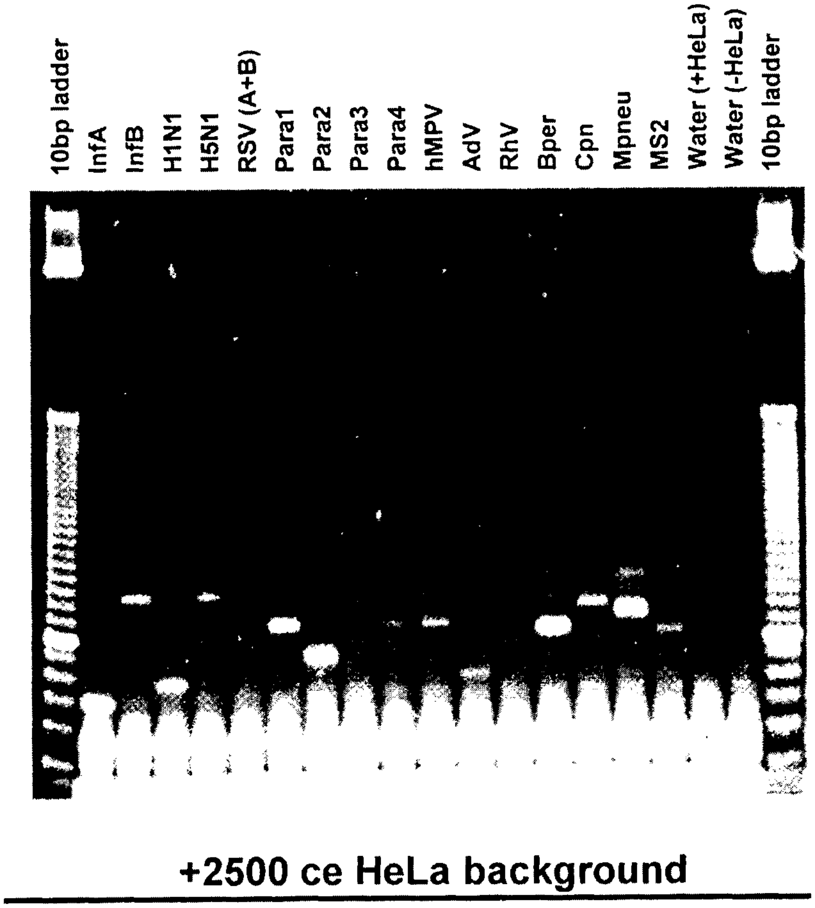

The subsequent addition of RNAse-free background HeLa chromosomal DNA (to a final concentration of approximately 2500 cell equivalents per reaction) did not significantly alter the amplification profile as judged by PAGE analysis (see FIG. 5 below).

EXAMPLE 9

Asymmetric RT-PCR

To optimize loading of PCR products onto beads during the Solid Phase RT-PCR, primers were carefully titrated in order to introduce a level of asymmetry into the amplification of target analytes. Specifically, for each analyte the unlabeled primer (of the same sense as that of the probe oligonucleotide) was serially reduced to a greater than 50-fold molar deficit when compared to the labeled primer.

The resulting asymmetric amplification profile was expected to allow an excess of the nascent strands available for subsequent successful priming with the probe oligonucleotide to accumulate. Indeed, in most cases more efficient loading onto beads was observed with decreasing amounts of the unlabeled primers. However, molar ratios of unlabeled:labeled primers that gave optimal loading of PCR products onto cognate beads ranged from 1:1 to 1:6, respectively (see Table 5, below).

TABLE 5

Primer Concentrations Directing Efficient Bead-based Detection Following RT-PCR Amplification of Target Analytes

| Primer | Final Primer Concentration (uM) | Ratio (Labeled/Unlabeled) |
|---|---|---|
| InfA2 R | 0.4 | 1.5 |
| Am-InfA2 F* | 0.6 | |
| P-InfB-2R | 0.2 | 6 |
| Am-InfB-2 F* | 1.2 | |
| P-H1N1 R | 0.4 | 1.5 |
| Am-H1N1 F* | 0.6 | |
| P-H5N1 R | 0.2 | 6 |
| Am-H5N1 F* | 1.2 | |
| P-RSV-3 R | 0.8 | 1.25 |
| Am-RSV-3 F* | 1 | |
| GB P-HPIV1 R | 1 | 1 |
| GB HP1V1 F* | 1 | |
| P-Para2 R | 0.15 | 3.33 |
| Am-Para2 F* | 0.5 | |
| Para3 R | 0.5 | 2.4 |
| Am-Para3 F* | 1.2 | |
| Para4 R | 0.7 | 1.29 |
| Am-Para4 F* | 0.9 | |
| P-hMPV R | 0.6 | 1.33 |
| Am-hMPV F* | 0.8 | |
| P-AdV F | 0.35 | 2.57 |
| AdV R* | 0.9 | |
| P-T7truncRhi F | 0.6 | 1.33 |
| truncRhi R* | 0.8 | |
| P-Bper F | 0.1 | 4 |
| Bper R* | 0.4 | |
| P-Cpn F | 0.4 | 2.5 |
| Cpn R* | 1 | |
| P-Mpneu F | 0.2 | 2 |
| Mpneu R* | 0.4 | |
| P-MS2-2 F | 0.4 | 2.5 |
| Am-MS2-2 R* | 1 | |
| hum f | 0.075 | 5.33 |
| hum R* | 0.4 | |

*AlexaFluor 647 -labeled primers

EXAMPLE 10

Analyte Detection Sensitivities

Preliminary analyte detection sensitivities were defined following amplification and detection of known amounts of synthetic control constructs using RTIplots threshold values established. Washes (×6) were conducted using 1× Sheath buffer. Unambiguous calls were successfully made for the following copies of synthetic constructs (see Table 6):

TABLE 6

Confirmed Analyte Detection Sensitivities

| Analyte | Copies Detected |
|---|---|
| Influenza A | 400 |
| Influenza B | 400 |
| H1N1 | 400 |
| H5N1 | 2000 |

TABLE 6-continued

Confirmed Analyte Detection Sensitivities

| Analyte | Copies Detected |
|---|---|
| RSV (A&B) | 2000 |
| Parainfluenza 1 | 2000 |
| Parainfluenza 2 | 2000 |
| Parainfluenza 3 | 5000 |
| Parainfluenza 4 | 2000 |
| hMPV | 2000 |
| AdV | 2000 |
| RhV | 10000 |
| *B. pertussis* | 400 |
| *C. pneumophila* | 2000 |
| *M. pneumophila* | 400 |

EXAMPLE 11

Detection Sensitivities of RSV-A vs RSV-B

Preliminary data analyzing the sensitivity of detection of RSV (RSV-A and RSV-B) involved using an equimolar mixture of both the C18 and C19 control constructs (see FIG. 1 for sequences) as a target template. Therefore, to obtain independent detection sensitivity data for both RSV-A and RSV-13, known copies of either construct was independently assessed using the multiplex assay according to the present invention. The assay allowed the successful detection of 125 copies of the RSV-A construct (C18) and 250 copies of the RSV-B construct (C19) following analysis using RTIplots software (with a threshold setting of 400 for RSV)

EXAMPLE 12

Clinical Data

Figure 6:
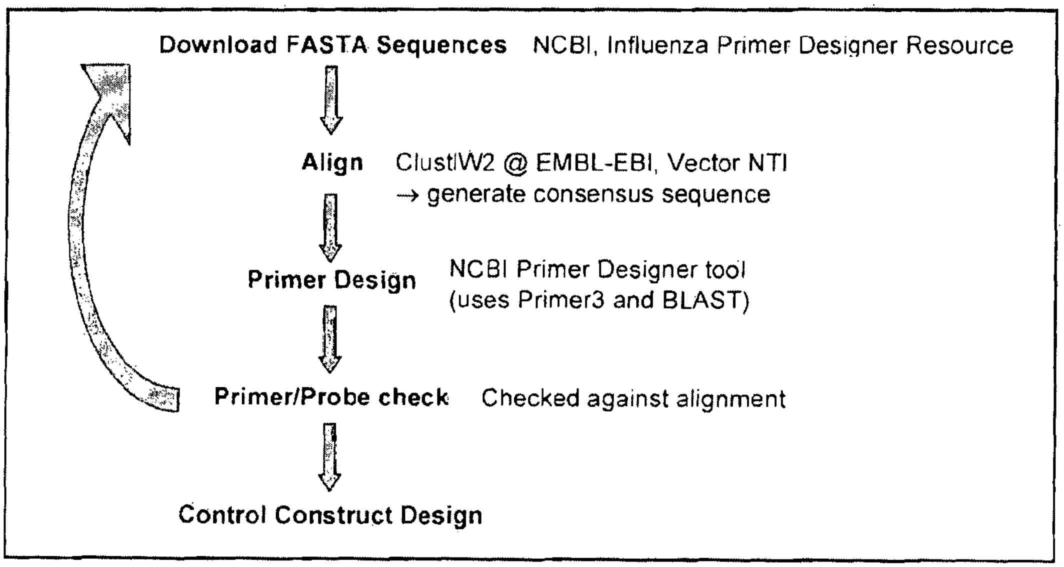
FIG. 6 is a graphical representation showing an overview of the general primer design process.

A preliminary evaluation of the assay was conducted in a blinded fashion on an enriched set of 72 archived samples (Table 7) for which data generated via viral isolation from cell culture were recorded. Samples were either stored at −80° C. as nucleic acid or as clinical specimens that required re-extraction prier to assaying. A summary of the findings of this study are shown in FIG. 6. It should be noted that the viral culture data from 3 samples indicated a coinfection; thus the total number of samples (72) is equal to the 62 analyte-positive samples plus the 13 analyte-negative samples minus 3 to account for coinfected samples.

Briefly, the data indicate a 95% concordance of the assay with cell culture data for analyte positive samples (excluding indeterminate RTIplex results from the analysis). Furthermore, of the 13 samples for which virus was unable to be isolated and/or identified following culture, the assay was able to detect pathogens in 7 (54%) of these samples. Furthermore, from these 72 clinical specimens, the assay detected a total of 24 analytes previously unreported by the cell culture techniques. Many of these additionally identified analytes have been confirmed by PCR-based methods (performed at the Department of Molecular Microbiology, Royal Women's Hospital, Melbourne, Victoria, Australia.

TABLE 7

| Cell culture data analysis on archived clinical specimens | | | | | | | |
|---|---|---|---|---|---|---|---|
| | Cell Culture | MM PCR POS | Concordant RTIplex* | % Concordance with Cell Culture | Notes | RTIplex POS; Cell Culture NEG | Unreported Cell Culture Infections/Coinfections Identified by RTIplex |
| InfA | 11 | NT | 10 | 91% | | | 0 |
| InfB | 4 | NT | 4 | 100% | | | 0 |
| H1N1 | NT | (4/7) | (8) | na | | | 0 |
| H5N1 | NT | — | — | na | | | 0 |
| RSV | 13 | NT | 12 | 92% | *RTIplex HuIC NEG (IND) | | 2 |
| Para1 | 0 | — | — | na | | | 1 |
| Para2 | 9 | NT | 7 | 78% | *RTIplex HuIC NEG (IND) | | 1 |
| Para3 | 11 | 1/1 | 11 | 100% | | | 0 |
| Para4 | NT | — | — | na | | | 0 |
| hMPV | 3 | NT | 3 | 100% | | | 0 |
| AdV | 4 | NT | 4 | 100% | | | 2 |
| RhV | NT | — | — | na | | | 9 |
| Bper | 3 | NT | 3 | 100% | | | 4 |
| Cpn | 0 | — | — | na | | | 0 |
| Mpneu | 4 | NT | 3 | 75% | | | 5 |
| Total | 62 | na | 57 | 92% | (95% if exclude INDs) | | 24 |
| No Isolation | 13 | na | 5 | na | | 7 | |

NT = Not Tested
MM = Department of Molecular Microbiology, Royal Womens Hospital, Melbourne, Victoria, Australia
IND = Indeterminant
na = not applicable
HuIC = human internal control

EXAMPLE 13

Oligonucleotide Primers and Probes Used in the Assay Method

Table 8 provides a list of primers and capture probes used in the assay method and kit for respiratory pathogens. At least two primer pairs and corresponding probes are used in the kit. By "at least two" means 2, 3, 4, 5, 6, 7, 8, 9, 10, 11, 12, 13, 14, 15, 16, 17 or 18.

Those skilled in the art will appreciate that aspects of aspects described herein are susceptible to variations and modifications other than those specifically described. It is to be understood that these aspects include all such variations and modifications. These aspects also include all of the steps, features, compositions and compounds referred to or indicated in this specification, individually or collectively, and any and all combinations of any two or more of the steps or features.

TABLE 8

| Primers and capture probes used in the assay method for rspiratory pathogens | | | | |
|---|---|---|---|---|
| Analyte | Target | Primary Amplicon Length (bp) | Oligo ID | Sequence (5'-3') |
| Influenza A | Segment 7 MP | 122 | Am-InfA2 F | /5AmMC6/CGAGGTCGAAACGTAYGTTCTYTCTAT |
| | | | InfA2 R | GCCATTCCATGAGAGCCTCRAGATC |
| | | | Acry InfA2 Pr | /5Acryd/AATTGAATTCGGATCCAGTCTCTGCGCGATCTCGGCTTTGAG |
| Influenza B | Segment 4 HA | 124 | Am-InfB-2 F | /5AmMC6/TACGGTGGATTAAACAAAAGCAAGCC |
| | | | InfB-2 R | CAGGAGGTCTATATTTGGTTCCATTGGC |
| | | | Acry AS InfB-2 P | /5Acryd/AAT/iAmMC6T/GAATTCGGATCCGGTGTTTTCACCCATATTGGGCAATT |
| Influenza A | Segment 4 HA | 78 | H1N1 R | /5AmMC6/GCTTTTTGCTCCAGCATGAGGACAT |
| H1N1 | | | H1N1 F | CCCAAGACAAGTTCATGGCCCAATCA |
| (2009) | | | Acry H1N1 P | /5Acryd/AATTGAATTCGGATCC CGAACAAAGGTGTAACGGCAGCATG |
| Influenza A | Segment 4 HA | 128 | Am-H5N1 F | /5AmMC6/GCTCTGCGATCTAGATGGAGTGAAGCC |
| H5N1 | | | H5N1 R | YCTTCTCCACTATGTAAGACCATTCCGG |
| (Avian) | | | Acry AS-H5N1 P | /5Acryd/AATTGAATTCGGATCCCCGAGGAGCCATCCAGCTACACTAC |

TABLE 8-continued

Primers and capture probes used in the assay method for rspiratory pathogens

| Analyte | Target | Primary Amplicon Length (bp) | Oligo ID | Sequence (5'-3') |
|---|---|---|---|---|
| RSV (A & B) | Poly-merase | 126 | Am-RSV-3 F | /5AmMC6/ACAGTCAGTAGTAGACCATGTGAATTC |
| | | | RSV-3 R | RTCRATATCTTCATCACCATACTTTTCTGTTA |
| | | | Acry AS-RSV-3 P | /5Acryd/AATTGAATTCGGATCCGTTCTATAAGCTGGTATTGATGCAGG |
| HPIV-1 | HN | 131 | Am GB HPIV1 F | /5AmMC6/TGGTGATGCAATATATGCGTATTCATC |
| | | | GB HPIV1 R | CCGGGTTTAAATCAGGATACATATCTG |
| | | | Acry GB HPIV1 P | /5Acryd/AAT/iAmMC6T/GAATTCGGATCCCCTATATCTGCACATCCTTGAGTGATT |
| HPIV-2 | HN | 90 | Am-Para2 F | /5AmMC6/CYCGTCCTGGAGTCATGCCATGCAA |
| | | | Para2 R | CRTTAAGCGGCCACACATCTGCGT |
| | | | Acry AS-Para2 P | /5Acryd/AAT/iAmMC6T/GAATTCGGATCCACCCCTGTGATGCAATTAGCAGGGCA |
| HPIV-3 | HN | 123 | Am-Para3 F | /5AmMC6/CAAGTTGGCAYAGCAAGTTACAATTAGGA |
| | | | Para3 R | GTCCCCATGGACATTCATTGTTTCCTGGT |
| | | | Acry AS-Para3 P | /5ThioMC6-D/AAT/iAmMC6T/ GAATTCGGATCCAGCACATTATGCCATGTCCATTTTATCC |
| HPIV-4 | Phospho-protein | 109 | Am-Para4 F | /5AmMC6/GTTGATCAAGACAATACAATTACACTTGA |
| | | | Para4 R | TAAGTGCATCTATACGAACRCCTGCTC |
| | | | Acry GB HPIV-4 Pr1 | /5Acryd/AAT/iAmMC6T/GAATTCGGATCC GGTTCCAGACAAAATGGGTCTTGCTA |
| | | | Acry GB HPIV-4 Pr2 | /5Acryd/AAT/iAmMC6T/GAATTCGGATCC GGTTCCAGATAATATGGGTCTTGCTA |
| hMPV | M2 | 109 | Am-hMPV F | /5AmMC6/GACAAATCATMATGTCTCGYAARGCTCC |
| | | | hMPV R | CTATCWGGCCAACTCCAGTAATTGTG |
| | | | Acry AS-hMPV P | /5ThioMC6-D/AAT/iAmMC6T/GAATTCGGATCCTTGCCCCGYACTTCATATTTGCA |
| AdV (B, C & E) | Hexon | 82 | AdV F | TGCCSCARTGGKCDTACATGCACATC |
| | | | AdV R | /5AmMC6/GCRCGGGCRAACTGCACCAG |
| | | | Acry AdV B/E P | /5Acryd/AATTGAATTCGGATCC GCTTCGGAGTACCTGAGTCCGGGT |
| | | | Acry AdV C P | /5Acryd/AATTGAATTCGGATCC TCGGGCCAGGACGCCTCGGAGTAC |
| RhV | 5/UTR | 209 | truncRhi R | /5AmMC6/GAAACACGGACACCCAAAGTAGT |
| | | | T7truncRhi F | ACTCACTATAGG AGCCTGCGTGGCKGCC |
| | | | Acry Rhi P | /5ThioMC6-D/AAT/iAmMC6T/GAATTCGGATCCTCCTCCGGCCCCTGAATGYGGCTAA |
| *B. pertussis* | IS481 | 105 | Bper F | CCGGCCGGATGAACACCCATAAGCA |
| | | | Bper R | /5AmMC6/GGGCCGCTTCAGGCACACAAACTTG |
| | | | Acry Bper P | /5ThioMC6-D/AAT/iAmMC6T/GAATTCGGATCCTGCCCGATTGACCTTCCTACGTCGA |
| *C. pneumoniae* | MOMP | 122 | Cpn F | CATGAATGGCAAGTAGGAGCCTCTC |
| | | | Cpn R | /5AmMC6/AGTTTTGGCTGAGCAATGCGGATGT |
| | | | Acry Cpn P | /5ThioMC6-D/AAT/iAmMC6T/GAATTCGGATCCTGGTCTCGAGCAACTTTTGATGCTG |
| *M. pneumoniae* | P1 Cytadhesin | 114 | Mpneu F | GAACCGAAGCGGCTTTGACCGCATC |
| | | | Mpneu R | /5AmMC6/GCGTGGGCGTTTGCGGGTTTAACTT |
| | | | Acry Mpneu P | /5ThioMC6-D/AAT/iAmMC6T/GAATTCGGATCCGGGCGCGCCTTATACGACCTCGATT |
| MS2 RNA Control | Matrix | 102 | MS2-2 R | /5AmMC6/CTTTTGCAGGACTTCGGTCGACGCC |
| | | | MS2-2 F | GCACGCTCCTGCTACAGCCTCTTCC |
| | | | Acry MS2-2 P | /5Acryd/AATTGAATTCGGATCC GAAGTGCCGCAGAACGTTGCGAACC |
| Human Control | MYL3 | 131 | MYL3 F | GCACCCAGACAATACACACAGGTGT |
| | | | MYL3 R | /5AmMC6/GGCGGAAGTCAGCATGTGTCTG |
| | | | PapType ProbeMLC_ Int Oligo | /5Acryd/AAT/iAmMC6T/ AAAGGGAGGACAGCTATGGACCAAACACAGACACAGAGAGACCCACAGAC A |

BIBLIOGRAPHY

Chadwick et al. (1998) *J. Virol. Methods* 70:59-70
Chan and Fox (1999) *Rev. Med. Microbiol.* 70:185-196
Compton (1991) *Nature* 350:91-92
Demidov and Broude Eds. (2004) *Horizon Bioscience*
Guatelli et al. (1990) *Proc. Natl Acad. ScI USA* 57:1874-1878
Hill (1996) *J. Clin. Ligand Assay* 7P:43-51
Kievits et al. (1991) *J. Virol. Methods* 35:273-286
Lyamichev et al. (1999) *Nat. Biotechnol.* 77:292-296
Ryan et al. (1999) *Mol. Diagn.* 4:135-144

What is claimed is:

1. A method of screening a sample for a multiplicity of respiratory pathogens to detect a particular pathogen, the method comprising:

(a) isolating nucleic acid from the sample, which nucleic acid putatively comprises nucleic acid from one or more respiratory pathogens;

(b) subjecting the nucleic acid to solid phase amplification in the presence of two or more combinations of aqueous primer pairs and corresponding oligonucleotide probes immobilized to a bead in a beadset, wherein the aqueous primer pairs comprise forward primers selected from the group consisting of SEQ ID NOs:1 to 16, 33 and 35 and corresponding reverse primers selected from the group consisting of SEQ ID NOs:17 to 32, 34 and 36, respectively, and the corresponding oligonucleotide probes are selected from the group consisting of SEQ ID NOs:37 to 54, or the primer pairs and corresponding probes are selected from two or more of the sequences listed in Table 8 (SEQ ID NOs:74 to 141); wherein an aqueous primer pair directs the amplification of a region of nucleic acid from a respiratory pathogen, the number of primer pairs being selected on the basis of the number of pathogens desired to be screened and wherein at least one member of the aqueous primer pair comprises a first optically detectable label that is incorporated into a resulting amplicon following amplification; wherein the amplicon is captured by hybridizing to an oligonucleotide probe that is complementary to a region of the amplicon and immobilized to a bead in a beadset, the beadset having subsets of beads, each subset being homogenous with respect to bead size and, optionally, intensity of a second optically detectable label, thereby creating a heterogeneous beadset based on size and/or second detectable label intensity and wherein the number of subsets corresponds to the number of respiratory pathogens to be screened;

(c) determining to which of the beads an amplicon has bound on the basis of the intensity of the first detectable label and, where amplicons are bound to multiple subsets of beads, distinguishing between the multiple subsets of beads on the basis of bead size and, optionally, on the basis of second optically detectable label intensity;

wherein binding of an amplicon to a particular subset of beads is indicative of the presence of a particular respiratory pathogen in the sample.

2. The method of claim 1 wherein the amplicon initiated by extension of the primer comprising the first optically detectable label serves as a template for hybridization and extension of an oligonucleotide comprising a second optionally detectable label, wherein the oligonucleotide is immobilized to a bead in a bead set.

3. A method of screening a sample for a multiplicity of respiratory pathogens to detect a particular pathogen, the method comprising:

(a) isolating nucleic acid from the sample, which nucleic acid putatively comprises a nucleic acid from one or more respiratory pathogens;

(b) subjecting the nucleic acid to solid phase amplification in the presence of two or more combinations of aqueous primer pairs and corresponding oligonucleotide probes immobilized to a bead in a beadset, wherein the forward primers are selected from the group consisting of SEQ ID NOs:1 to 16, 33 and 35 and corresponding reverse primers are selected from the group consisting of SEQ ID NOs:17 to 32, 34 and 36, respectively, and the corresponding oligonucleotide probes are selected from the group consisting of SEQ ID NOs:37 to 54, or the primer pairs and corresponding probes are selected from two or more of the sequences listed in Table 8 (SEQ ID NOs:74 to 141); wherein an aqueous primer pair directs the amplification of a region of nucleic acid from a respiratory pathogen, the number of primer pairs being selected on the basis of the number of pathogens desired to be screened and wherein at least one member of the primer pair comprises a first optically detectable label that is incorporated into a resulting amplicon following amplification, wherein the resulting amplicon initiated by extension of the primer comprising the first optically detectable label serves as a template for hybridization and extension of an oligonucleotide primer comprising a second optically detectable label, wherein the oligonucleotide primer is immobilized to a bead in a beadset, the beadset having subsets of beads, each subset being homogenous with respect to bead size and, optionally, intensity of a second optically detectable label, thereby creating a heterogeneous beadset based on size and/or second detectable label intensity and wherein the number of subsets corresponds to the number of respiratory pathogens to be screened;

(c) determining to which of the beads an amplicon has bound on the basis of the intensity of the first detectable label and, where amplicons are bound to multiple subsets of beads, distinguishing between the multiple subsets of beads on the basis of bead size and, optionally, on the basis of second optically detectable label intensity;

wherein binding of an amplicon to a particular subset of beads is indicative of the presence of a particular respiratory pathogen in the sample.

4. The method of claim 1 or 3 comprising distinguishing between multiple subsets of beads on the basis of second optically detectable label intensity.

5. The method of claim 1 or 3 wherein the respiratory pathogen is selected from the group consisting of Influenza A, Influenza B, Influenza A H1N1, Influenza A H5N1, Respiratory Syncytial Virus subtype A, Respiratory Syncytial Virus subtype B, Human Parainfluenza Virus 1, Human Parainfluenza Virus 2, Human Parainfluenza Virus 3, Human Parainfluenza Virus 4, Human Metapneumovirus, Human Adenovirus subtype B, Human Adenovirus subtype C, Human Adenovirus subtype E, Human Entero/Rhinovirus, *Bordetella pertussis, Haemophilus* Influenza, Human Coronavirus, Human Bocavirus types 1, 2 and 3, and microbes from the genera *Streptococcus, Haemophilus, Moraxella, Pseudomonas, Klebsiella, Stenotrophomonas, Acinetobacter, Staphylococcus, Mycoplasma, Legionella, Chlamydophila, Mycobacterium, Coxiella, Nocardia, Pneumocystis, Nocardia*, and *Aspergillus*.

6. The method of claim 1 or 3 wherein the nucleic acid from one or more respiratory pathogens is selected from the group consisting of the gene encoding Segment 7 of Influenza A matrix protein, the gene encoding Segment 4 of the Influenza B hemagglutinin, the gene encoding Segment 4 of the 2009 H1N1 pandemic strain of Influenza A, the gene encoding Segment 4 of the H5N1 pandemic strain of Influenza A, polymerase gene of the Respiratory Syncytial Virus (types A and B), the gene encoding hemagglutinin-neuraminidase glycoprotein of Human Parainfluenza Virus 1, 2 and 3, phosphoprotein gene of Human Parainfluenza Virus 4, the gene encoding the M2 region of the matrix protein of Human Metapneumovirus, the gene encoding the Hexon region of Adenovirus Types B, C and E, 5'UTR region of Human Rhinovirus/Enterovirus, the Insertion Sequence (IS) 481 of *Bordetella pertussis*, the gene encoding Major Outer Membrane Protein of *Chlamidophila pneumoniae* and the gene encoding P1 Cytadhesin of *Mycoplasma pneumoniae.*

7. The method of claim 1 wherein the second optically detectable label is attached to the oligonucleotide probe.

8. The method of claim 7 wherein the second optically detectable label is attached to the oligonucleotide probe via an amino C6 modification of an internal thymidine residue of the oligonucleotide probe.

9. The method of claim 1 or 3 wherein the oligonucleotide probe is a hemi-nested oligonucleotide.

10. The method of claim 1 or 3 wherein the oligonucleotide probe is covalently attached to the bead via a thiol or a methacryl linkage.

11. The method of claim 1 or 3 wherein the size of the beads within each subset is selected from the group consisting of 3.0 μm, 3.5 μm, 3.8 μm, 4.1 μm, 5.0 μm, 5.2 μm and 5.7 μm in diameter.

12. A kit comprising two or more combinations of aqueous primer pairs and corresponding oligonucleotide probes immobilized to a bead in a beadset, wherein the aqueous primer pairs comprise forward primers selected from the group consisting of SEQ ID NOs:1 to 16, 33 and 35 and corresponding reverse primers selected from the group consisting of SEQ ID NOs:17 to 32, 34 and 36, respectively, and the corresponding oligonucleotide probes are selected from the group consisting of SEQ ID NOs:37 to 54, or the primer pairs and corresponding oligonucleotide probes are selected from two or more of the sequences listed in Table 8 (SEQ ID NOs:74 to 141), wherein at least one member of the aqueous primer pair comprises a first optically detectable label that is incorporated into a resulting amplicon following amplification and wherein the oligonucleotide probe optionally comprises a second optically detectable label.

13. The kit of claim 12 wherein the second optically detectable label is attached to the oligonucleotide probe via an amino C6 modification of an internal thymidine residue of the oligonucleotide probe.

14. The kit of claim 12, wherein the oligonucleotide probe is immobilized to the bead in the beadset via a thiol or a methacryl linkage, the beadset having subsets of beads.

15. The kit of claim 14, wherein the size of the beads within each subset is selected from the group consisting of 3.0 μm, 3.5 μm, 3.8 μm, 4.1 μm, 5.0 μm, 5.2 μm and 5.7 μm in diameter.

* * * * *

UNITED STATES PATENT AND TRADEMARK OFFICE

CERTIFICATE OF CORRECTION

PATENT NO. : 9,738,941 B2
APPLICATION NO. : 14/349256
DATED : August 22, 2017
INVENTOR(S) : Poetter et al.

It is certified that error appears in the above-identified patent and that said Letters Patent is hereby corrected as shown below:

In the Specification

In Column 3 at Line 32, Change “Solid” to --solid--.

In Column 4 at Lines 27-28, Change “*Chlamidophila*” to --*Chlamydophila*--.

In Column 4 at Line 32, Change “NO:33” to --NOs:33--.

In Column 4 at Line 34, Change “NO:34” to --NOs:34--.

In Column 4 at Line 42, Change “NO:33” to --NOs:33--.

In Column 4 at Line 44, Change “NO:34” to --NOs:34--.

In Column 4 at Line 54, Change “NO:74” to --NOs:74--.

In Column 4 at Lines 62-63, Change “methoxyciumarin,” to --methoxycoumarin,--.

In Column 4 at Line 63, Change “Phyccerythrin” to --Phycoerythrin--.

In Column 5 at Line 13 (approx.), Change “Fluor X,” to --FluorX,--.

In Column 6 at Line 17, Change “*Chlamidophila*” to --*Chlamydophila*--.

In Column 6 at Line 37, Change “*Chlamidophila*” to --*Chlamydophila*--.

In Column 7 at Line 23 (approx.), Change “*peneumoniae*” to --*pneumoniae*--.

In Columns 9-10 at Line 32 (approx.), Change “GCGTGGGCGTITGCGGGTTTAACTT” to --GCGTGGGCGTTTGCGGGTTTAACTT--.

Signed and Sealed this
Sixteenth Day of July, 2019

Andrei Iancu
*Director of the United States Patent and Trademark Office*

In Columns 9-10 at Line 40 (approx.), Change
“GAATTCGGATCCCCCAGGAGCCAT CCAGCTACACTAC” to
--GAATTCGGATCCCCCAGGAGCCATCCAGCTACACTAC--.

In Column 25 at Line 30, Change “primer,” to --primer--.

In Column 25 at Line 65, Change “*Chlamidophila*” to --*Chlamydophila*--.

In Column 26 at Line 1, Change “*Chlamidophila*” to --*Chlamydophila*--.

In Column 26 at Line 64, Change “Chart” to --Chan--.

In Column 26 at Line 65, Change “70” to --10--.

In Column 27 at Line 39, Change “methoxyciumarin,” to --methoxycoumarin,--.

In Column 27 at Line 40, Change “Phyccerythrin” to --Phycoerythrin--.

In Column 27 at Line 57, Change “Fluor X,” to --FluorX,--.

In Column 28 at Lines 59-60, Change “900 nm5” to --900 nm,--.

In Column 28 at Line 60, Change “1.4 µm$_J$” to --1.4 µm,--.

In Column 28 at Line 64, Change “4.4 µm$_J$” to --4.4 µm,--.

In Column 28 at Line 65, Change “4.6 µm$_J$” to --4.6 µm,--.

In Column 28 at Line 67, Change “6.3 µm$_5$” to --6.3 µm,--.

In Column 29 at Line 1, Change “7.4 µm$_4$” to --7.4 µm,--.

In Column 29 at Line 4, Change “9.6 µm$_J$” to --9.6 µm,--.

In Column 30 at Line 48, Change “mean” to --means--.

In Column 33 at Lines 59-60, Change
“GAATTCGGATCCCCGAGGAGCCAT CCAGCTACACTAC” to
--GAATTCGGATCCCCGAGGAGCCATCCAGCTACACTAC--.

In Column 35 at Line 41, Change “methoxyciumarin,” to --methoxycoumarin,--.

In Column 35 at Line 42, Change “Phyccerythrin” to --Phycoerythrin--.

In Column 35 at Lines 50-51, Change “particulary” to --particularly--.

In Column 35 at Line 59, Change “Fluor X,” to --FluorX,--.

In Column 39 at Line 26, Change “Gene” to --Gene:--.

In Column 40 at Line 18, Change “Gene” to --Gene:--.

In Column 40 at Line 38 (approx.), Change “HIN1” to --H1N1--.

In Column 40 at Line 45, Change “Gene” to --Gene:--.

In Column 41 at Line 2, Change “Glycprotein” to --Glycoprotein--.

In Column 41 at Line 4, Change “Gene” to --Gene:--.

In Column 42 at Line 40, Change “FIN” to --HN--.

In Column 42 at Line 41, Change “FIN” to --HN--.

In Column 42 at Line 65, Change “(SEq” to --(SEQ--.

In Column 43 at Line 2, Change “FIN” to --HN--.

In Column 43 at Line 3, Change “FIN” to --HN--.

In Column 43 at Line 24 (approx.), Change “(SEq” to --(SEQ--.

In Columns 43-44 at Line 14 (approx., In the Table), Change “(SEq” to --(SEQ--.

In Column 44 at Line 25 (approx.), Change “Gene” to --Gene:--.

In Column 45 at Line 10, Change “(SEq” to --(SEQ--.

In Column 45 at Line 43 (approx.), Change “(Beer)” to --(Bper)--.

In Column 45 at Line 45 (approx.), Change “Gene” to --Gene:--.

In Column 46 at Line 1, Change “*Chlamidophila*” to --*Chlamydophila*--.

In Column 47 at Line 15, Change “Gene” to --Gene:--.

In Column 50 at Line 5, Change “1804” to --180 μL--.

In Column 50 at Line 6, Change “1804=1204” to --180 μL=120 μL--.

In Column 53 at Line 28, Change “I.” to --I:--.

In Column 56 at Line 49, Change “prier” to --prior--.

In Columns 57-58 at Line 1 (Table 8), Change “rspiratory” to --respiratory--.

In Columns 65-66 at Line 20 (approx.), Change “Chlamidophila” to --Chlamydophila--.

In Columns 69-70 at Line 42 (approx.), Change “Chlamidophila” to --Chlamydophila--.

In Columns 75-76 at Line 39 (approx.), Change “Chlamidophila” to --Chlamydophila--.

In the Claims

In Column 112 at Line 21 (approx.), In Claim 6, change “*Chlamidophila*” to --*Chlamydophila*--.

SEQUENCE LISTING

```
<160> NUMBER OF SEQ ID NOS: 141

<210> SEQ ID NO 1
<211> LENGTH: 27
<212> TYPE: DNA
<213> ORGANISM: artificial
<220> FEATURE:
<223> OTHER INFORMATION: Influenza A virus

<400> SEQUENCE: 1

cgaggtcgaa acgtaygttc tytctat                                          27


<210> SEQ ID NO 2
<211> LENGTH: 26
<212> TYPE: DNA
<213> ORGANISM: artificial
<220> FEATURE:
<223> OTHER INFORMATION: Influenza B virus

<400> SEQUENCE: 2

tacggtggat taaacaaaag caagcc                                           26


<210> SEQ ID NO 3
<211> LENGTH: 26
<212> TYPE: DNA
<213> ORGANISM: artificial
<220> FEATURE:
<223> OTHER INFORMATION: Influenza A virus

<400> SEQUENCE: 3

cccaagacaa gttcatggcc caatca                                           26


<210> SEQ ID NO 4
<211> LENGTH: 27
<212> TYPE: DNA
<213> ORGANISM: artificial
<220> FEATURE:
<223> OTHER INFORMATION: Influenza A virus

<400> SEQUENCE: 4

gctctgcgat ctagatggag tgaagcc                                          27


<210> SEQ ID NO 5
<211> LENGTH: 27
<212> TYPE: DNA
<213> ORGANISM: artificial
<220> FEATURE:
<223> OTHER INFORMATION: respiratory syncytial virus

<400> SEQUENCE: 5

acagtcagta gtagaccatg tgaattc                                          27


<210> SEQ ID NO 6
<211> LENGTH: 27
<212> TYPE: DNA
<213> ORGANISM: artificial
<220> FEATURE:
<223> OTHER INFORMATION: Human parainfluenza virus 1
```

<400> SEQUENCE: 6
tggtgatgca atatatgcgt attcatc 27

<210> SEQ ID NO 7
<211> LENGTH: 25
<212> TYPE: DNA
<213> ORGANISM: artificial
<220> FEATURE:
<223> OTHER INFORMATION: Human parainfluenza virus 2

<400> SEQUENCE: 7
cycgtcctgg agtcatgcca tgcaa 25

<210> SEQ ID NO 8
<211> LENGTH: 29
<212> TYPE: DNA
<213> ORGANISM: artificial
<220> FEATURE:
<223> OTHER INFORMATION: Human parainfluenza virus 3

<400> SEQUENCE: 8
caagttggca yagcaagtta caattagga 29

<210> SEQ ID NO 9
<211> LENGTH: 29
<212> TYPE: DNA
<213> ORGANISM: artificial
<220> FEATURE:
<223> OTHER INFORMATION: Human parainfluenza virus 4

<400> SEQUENCE: 9
gttgatcaag acaatacaat tacacttga 29

<210> SEQ ID NO 10
<211> LENGTH: 28
<212> TYPE: DNA
<213> ORGANISM: artificial
<220> FEATURE:
<223> OTHER INFORMATION: Human metapneumovirus

<400> SEQUENCE: 10
gacaaatcat matgtctcgy aargctcc 28

<210> SEQ ID NO 11
<211> LENGTH: 26
<212> TYPE: DNA
<213> ORGANISM: artificial
<220> FEATURE:
<223> OTHER INFORMATION: Adenovirus types B and E

<400> SEQUENCE: 11
tgccscartg gkcdtacatg cacatc 26

<210> SEQ ID NO 12
<211> LENGTH: 26
<212> TYPE: DNA
<213> ORGANISM: artificial
<220> FEATURE:
<223> OTHER INFORMATION: Adenovirus type C

<400> SEQUENCE: 12
tgccscartg gkcdtacatg cacatc 26

<210> SEQ ID NO 13
<211> LENGTH: 23

```
<212> TYPE: DNA
<213> ORGANISM: artificial
<220> FEATURE:
<223> OTHER INFORMATION: Human Rhinovirus/Enterovirus

<400> SEQUENCE: 13

gaaacacgga cacccaaagt agt                                              23


<210> SEQ ID NO 14
<211> LENGTH: 25
<212> TYPE: DNA
<213> ORGANISM: artificial
<220> FEATURE:
<223> OTHER INFORMATION: Bordetella pertussis

<400> SEQUENCE: 14

ccggccggat gaacacccat aagca                                            25


<210> SEQ ID NO 15
<211> LENGTH: 25
<212> TYPE: DNA
<213> ORGANISM: artificial
<220> FEATURE:
<223> OTHER INFORMATION: Chlamidophila pneumoniae

<400> SEQUENCE: 15

catgaatggc aagtaggagc ctctc                                            25


<210> SEQ ID NO 16
<211> LENGTH: 25
<212> TYPE: DNA
<213> ORGANISM: artificial
<220> FEATURE:
<223> OTHER INFORMATION: Mycoplasma pneumoniae

<400> SEQUENCE: 16

gaaccgaagc ggctttgacc gcatc                                            25


<210> SEQ ID NO 17
<211> LENGTH: 25
<212> TYPE: DNA
<213> ORGANISM: artificial
<220> FEATURE:
<223> OTHER INFORMATION: Influenza A virus

<400> SEQUENCE: 17

gccattccat gagagcctcr agatc                                            25


<210> SEQ ID NO 18
<211> LENGTH: 28
<212> TYPE: DNA
<213> ORGANISM: artificial
<220> FEATURE:
<223> OTHER INFORMATION: Infleunza B virus

<400> SEQUENCE: 18

caggaggtct atatttggtt ccattggc                                         28


<210> SEQ ID NO 19
<211> LENGTH: 25
<212> TYPE: DNA
<213> ORGANISM: artificial
<220> FEATURE:
<223> OTHER INFORMATION: Influenza A virus

<400> SEQUENCE: 19
```

-continued gctttttgct ccagcatgag gacat 25

<210> SEQ ID NO 20
<211> LENGTH: 28
<212> TYPE: DNA
<213> ORGANISM: artificial
<220> FEATURE:
<223> OTHER INFORMATION: Infleunza A virus

<400> SEQUENCE: 20
ycttctccac tatgtaagac cattccgg 28

<210> SEQ ID NO 21
<211> LENGTH: 32
<212> TYPE: DNA
<213> ORGANISM: artificial
<220> FEATURE:
<223> OTHER INFORMATION: Respiratory syncytial virus

<400> SEQUENCE: 21
rtcratatct tcatcaccat acttttctgt ta 32

<210> SEQ ID NO 22
<211> LENGTH: 27
<212> TYPE: DNA
<213> ORGANISM: artificial
<220> FEATURE:
<223> OTHER INFORMATION: Human parainfluenza virus 1

<400> SEQUENCE: 22
ccgggtttaa atcaggatac atatctg 27

<210> SEQ ID NO 23
<211> LENGTH: 24
<212> TYPE: DNA
<213> ORGANISM: artificial
<220> FEATURE:
<223> OTHER INFORMATION: Human parainfluenza virus 2

<400> SEQUENCE: 23
crttaagcgg ccacacatct gcgt 24

<210> SEQ ID NO 24
<211> LENGTH: 29
<212> TYPE: DNA
<213> ORGANISM: artificial
<220> FEATURE:
<223> OTHER INFORMATION: Human parainfluenza virus 3

<400> SEQUENCE: 24
gtccccatgg acattcattg tttcctggt 29

<210> SEQ ID NO 25
<211> LENGTH: 27
<212> TYPE: DNA
<213> ORGANISM: artificial
<220> FEATURE:
<223> OTHER INFORMATION: Human parainfluenza virus 4

<400> SEQUENCE: 25
taagtgcatc tatacgaacr cctgctc 27

<210> SEQ ID NO 26
<211> LENGTH: 26
<212> TYPE: DNA
<213> ORGANISM: artificial

<220> FEATURE:
<223> OTHER INFORMATION: Human metapneumovirus

<400> SEQUENCE: 26
ctatcwggcc aactccagta attgtg 26

<210> SEQ ID NO 27
<211> LENGTH: 20
<212> TYPE: DNA
<213> ORGANISM: artificial
<220> FEATURE:
<223> OTHER INFORMATION: Adenovirus types B and E

<400> SEQUENCE: 27
gcrcgggcra actgcaccag 20

<210> SEQ ID NO 28
<211> LENGTH: 20
<212> TYPE: DNA
<213> ORGANISM: artificial
<220> FEATURE:
<223> OTHER INFORMATION: Adenovirus type C

<400> SEQUENCE: 28
gcrcgggcra actgcaccag 20

<210> SEQ ID NO 29
<211> LENGTH: 28
<212> TYPE: DNA
<213> ORGANISM: artificial
<220> FEATURE:
<223> OTHER INFORMATION: Human Rhinovirus/Enterovirus

<400> SEQUENCE: 29
actcactata ggagcctgcg tggckgcc 28

<210> SEQ ID NO 30
<211> LENGTH: 25
<212> TYPE: DNA
<213> ORGANISM: artificial
<220> FEATURE:
<223> OTHER INFORMATION: Bordetella pertussis

<400> SEQUENCE: 30
gggccgcttc aggcacacaa acttg 25

<210> SEQ ID NO 31
<211> LENGTH: 25
<212> TYPE: DNA
<213> ORGANISM: artificial
<220> FEATURE:
<223> OTHER INFORMATION: Chlamidophila pneumoniae

<400> SEQUENCE: 31
agttttggct gagcaatgcg gatgt 25

<210> SEQ ID NO 32
<211> LENGTH: 25
<212> TYPE: DNA
<213> ORGANISM: artificial
<220> FEATURE:
<223> OTHER INFORMATION: Mycoplasma pneumoniae

<400> SEQUENCE: 32
gcgtgggcgt ttgcgggttt aactt 25

<210> SEQ ID NO 33
<211> LENGTH: 25
<212> TYPE: DNA
<213> ORGANISM: Homo sapiens

<400> SEQUENCE: 33
gcacccagac aatacacaca ggtgt 25

<210> SEQ ID NO 34
<211> LENGTH: 22
<212> TYPE: DNA
<213> ORGANISM: Homo sapiens

<400> SEQUENCE: 34
ggcggaagtc agcatgtgtc tg 22

<210> SEQ ID NO 35
<211> LENGTH: 25
<212> TYPE: DNA
<213> ORGANISM: Homo sapiens

<400> SEQUENCE: 35
gcacgctcct gctacagcct cttcc 25

<210> SEQ ID NO 36
<211> LENGTH: 25
<212> TYPE: DNA
<213> ORGANISM: Homo sapiens

<400> SEQUENCE: 36
cttttgcagg acttcggtcg acgcc 25

<210> SEQ ID NO 37
<211> LENGTH: 38
<212> TYPE: DNA
<213> ORGANISM: artificial
<220> FEATURE:
<223> OTHER INFORMATION: Influenza A virus

<400> SEQUENCE: 37
gaattcggat ccagtctctg cgcgatctcg gctttgag 38

<210> SEQ ID NO 38
<211> LENGTH: 38
<212> TYPE: DNA
<213> ORGANISM: artificial
<220> FEATURE:
<223> OTHER INFORMATION: Influenza B virus

<400> SEQUENCE: 38
gaattcggat ccggtgtttt cacccatatt gggcaatt 38

<210> SEQ ID NO 39
<211> LENGTH: 37
<212> TYPE: DNA
<213> ORGANISM: artificial
<220> FEATURE:
<223> OTHER INFORMATION: Influenza A virus

<400> SEQUENCE: 39
gaattcggat cccatgctgc cgttacacct ttgttcg 37

<210> SEQ ID NO 40
<211> LENGTH: 37

<212> TYPE: DNA
<213> ORGANISM: artificial
<220> FEATURE:
<223> OTHER INFORMATION: Influenza A virus

<400> SEQUENCE: 40
gaattcggat ccccgaggag ccatccagct acactac 37

<210> SEQ ID NO 41
<211> LENGTH: 38
<212> TYPE: DNA
<213> ORGANISM: artificial
<220> FEATURE:
<223> OTHER INFORMATION: Respiratory syncytial virus

<400> SEQUENCE: 41
gaattcggat ccgttctata agctggtatt gatgcagg 38

<210> SEQ ID NO 42
<211> LENGTH: 39
<212> TYPE: DNA
<213> ORGANISM: artificial
<220> FEATURE:
<223> OTHER INFORMATION: Human parainfluenza virus 1

<400> SEQUENCE: 42
gaattcggat cccctatatc tgcacatcct tgagtgatt 39

<210> SEQ ID NO 43
<211> LENGTH: 38
<212> TYPE: DNA
<213> ORGANISM: artificial
<220> FEATURE:
<223> OTHER INFORMATION: Human parainfluenza virus 2

<400> SEQUENCE: 43
gaattcggat ccacccctgt gatgcaatta gcagggca 38

<210> SEQ ID NO 44
<211> LENGTH: 40
<212> TYPE: DNA
<213> ORGANISM: artificial
<220> FEATURE:
<223> OTHER INFORMATION: Human parainfluenza virus 3

<400> SEQUENCE: 44
gaattcggat ccagcacatt atgccatgtc cattttatcc 40

<210> SEQ ID NO 45
<211> LENGTH: 38
<212> TYPE: DNA
<213> ORGANISM: artificial
<220> FEATURE:
<223> OTHER INFORMATION: Human parainfluenza virus 4

<400> SEQUENCE: 45
gaattcggat ccggttccag ayaawatggg tcttgcta 38

<210> SEQ ID NO 46
<211> LENGTH: 35
<212> TYPE: DNA
<213> ORGANISM: artificial
<220> FEATURE:
<223> OTHER INFORMATION: Human metapneumovirus

<400> SEQUENCE: 46

-continued gaattcggat ccttgccccg yacttcatat ttgca 35

<210> SEQ ID NO 47
<211> LENGTH: 36
<212> TYPE: DNA
<213> ORGANISM: artificial
<220> FEATURE:
<223> OTHER INFORMATION: Adenovirus types B and E

<400> SEQUENCE: 47
gaattcggat ccgcttcgga gtacctgagt ccgggt 36

<210> SEQ ID NO 48
<211> LENGTH: 36
<212> TYPE: DNA
<213> ORGANISM: artificial
<220> FEATURE:
<223> OTHER INFORMATION: Adenovirus type C

<400> SEQUENCE: 48
gaattcggat cctcgggcca ggacgcctcg gagtac 36

<210> SEQ ID NO 49
<211> LENGTH: 37
<212> TYPE: DNA
<213> ORGANISM: artificial
<220> FEATURE:
<223> OTHER INFORMATION: Human Rhinovirus/Enterovirus

<400> SEQUENCE: 49
gaattcggat cctcctccgg cccctgaatg yggctaa 37

<210> SEQ ID NO 50
<211> LENGTH: 37
<212> TYPE: DNA
<213> ORGANISM: artificial
<220> FEATURE:
<223> OTHER INFORMATION: Bordetella pertussis

<400> SEQUENCE: 50
gaattcggat cctgcccgat tgaccttcct acgtcga 37

<210> SEQ ID NO 51
<211> LENGTH: 37
<212> TYPE: DNA
<213> ORGANISM: artificial
<220> FEATURE:
<223> OTHER INFORMATION: Chlamidophila pneumoniae

<400> SEQUENCE: 51
gaattcggat cctggtctcg agcaactttt gatgctg 37

<210> SEQ ID NO 52
<211> LENGTH: 37
<212> TYPE: DNA
<213> ORGANISM: artificial
<220> FEATURE:
<223> OTHER INFORMATION: Mycoplasma pneumoniae

<400> SEQUENCE: 52
gaattcggat ccgggcgcgc cttatacgac ctcgatt 37

<210> SEQ ID NO 53
<211> LENGTH: 51
<212> TYPE: DNA
<213> ORGANISM: Homo sapiens

<400> SEQUENCE: 53
aaagggagga cagctatgga ccaaacacag acacagagag acccacagac a 51

<210> SEQ ID NO 54
<211> LENGTH: 37
<212> TYPE: DNA
<213> ORGANISM: Homo sapiens

<400> SEQUENCE: 54
gaattcggat ccgaagtgcc gcagaacgtt gcgaacc 37

<210> SEQ ID NO 55
<211> LENGTH: 407
<212> TYPE: DNA
<213> ORGANISM: artificial
<220> FEATURE:
<223> OTHER INFORMATION: MS-2 phase

<400> SEQUENCE: 55
taatacgact cactataggg agaaattaac cctcactaaa gggagagttt cggcttctcc 60
ctcgacgcac gctcctgcta cagcctcttc cctgtaagcc aaaacttgac ttacatcgaa 120
gtgccgcaga acgttgcgaa ccgggcgtcg accgaagtcc tgcaaaaggt cacccagggt 180
aattttaacc ttggtgttgc tttagcagag gccaggtcga cagcctcaca actcgcgacg 240
caaaccattg cgctcgtgaa ggcgtacact gccgctcgtc gcggtaattg gcgccaggcg 300
ctccgctacc ttgccctaaa cgaagatcga aagtttcgat caaaacacgt ggccggcagg 360
tggttggagt tgcagttcgg ttggttacca ctaatgagtg cggccgc 407

<210> SEQ ID NO 56
<211> LENGTH: 407
<212> TYPE: DNA
<213> ORGANISM: artificial
<220> FEATURE:
<223> OTHER INFORMATION: Infleunza A virus

<400> SEQUENCE: 56
taatacgact cactataggg agaaattaac cctcactaaa gggagacttt ggccccatgg 60
aatgttatct cccttttaag cttcctatac agtttaactg ctctgtccat gttatttgga 120
tccccattcc catttagggc attttggaca aagcgtctac gctgcagtcc tcgctcactg 180
ggcacggtga gcgtgaacac aaatcctaaa atccccttag tcagaggtga caggattggt 240
cttgtcttta gccattccat gagagcctca agatctgtgt tcttccctgc aaagacatct 300
tcaagtctct gcgcgatctc ggctttgagg gggcctgacg ggacgataga gagaacgtac 360
gtttcgacct cggttagaag actcatcttt caatatctag cggccgc 407

<210> SEQ ID NO 57
<211> LENGTH: 454
<212> TYPE: DNA
<213> ORGANISM: artificial
<220> FEATURE:
<223> OTHER INFORMATION: Infleunza B virus

<400> SEQUENCE: 57
taatacgact cactataggg agaaattaac cctcactaaa gggagacttc taagaaacca 60
gcaatagctc cgaagaaacc cctttccttt aatagttttg caggaggtct atatttggtt 120
ccattggcaa gcttcaaagg tgttttcacc catattgggc aatttcctat ggcttttgca 180

```
tgttctcctg tgtagtaagg cttgcttttg tttaatccac cgtatttttc gtgaaggcaa    240

tctgcttaat ttggtcttct ccttctgtac aaatgtatgg tacttctact gttagtggat    300

tcgttgctgt tttgttgttg tcgttctttg ggacagccca agccattgtt gcgaaaaatc    360

cgtttctact ggtaacgtta gggcaagatc ctgaggttcc aagtctgtag ggtcctcctg    420

gtgccttttc tgcattgata acgttagcgg ccgc                                454


<210> SEQ ID NO 58
<211> LENGTH: 514
<212> TYPE: DNA
<213> ORGANISM: artificial
<220> FEATURE:
<223> OTHER INFORMATION: Influenza A virus (H1N1 2009)

<400> SEQUENCE: 58

taatacgact cactataggg agaaattaac cctcactaaa gggagattta tcattaatgt     60

aggatttgct gagctttggg tatgaatttc ctttttaac tagccatatt aaatttttgt     120

agaagctttt tgctccagca tgaggacatg ctgccgttac acctttgttc gagtcatgat    180

tgggccatga acttgtcttg gggaatatct caaacctttc aaatgatgac actgagctca    240

attgctctct tagctcctca taatcgatga aatctcctgg gtaacacgtt ccattgtctg    300

aactagatgt ttccacaatg taggaccatg agcttgctgt ggagagtgat tcacactctg    360

gatttcccag gatccagcca gcaatgttac atttacccaa atgcaatggg gctacccctc    420

ttagtttgca tagtttcccg ttatgcttgt cttctagaag gttaacagag tgtgttactg    480

ttacattctt ttctagtact gtgtctgcgg ccgc                                514


<210> SEQ ID NO 59
<211> LENGTH: 406
<212> TYPE: DNA
<213> ORGANISM: artificial
<220> FEATURE:
<223> OTHER INFORMATION: Influenza A virus (H5N1)

<400> SEQUENCE: 59

aatacgactc actataggga gaaattaacc ctcactaaag ggagacacaa atttaaatgc     60

aaattctgca ttgtaacgat ccattggagc acatccataa agatagacca gccaccatga    120

ttgccagtgc tagggaactc gccactgttg aataaattga cagtatttgg taagttccta    180

ttgattccaa ttttatttca gttcttcata gtcgttgaaa ttccctgggt aacagaggtc    240

attggctgga ttggccttct ccactatgta agaccattcc ggcacattga tgaattcgtc    300

acacattggg tttccgagga gccatccagc tacactacaa tctcttaaaa ttagaggctt    360

cactccatct agatcgcaga gcttcccgtt gtgtgtctgc ggccgc                   406


<210> SEQ ID NO 60
<211> LENGTH: 529
<212> TYPE: DNA
<213> ORGANISM: artificial
<220> FEATURE:
<223> OTHER INFORMATION: Respiratory syncytial virus

<400> SEQUENCE: 60

taatacgact cactataggg agaaattaac cctcactaaa gggagataga aaatgtcttt     60

atgattccac gatttttatt ggatgctgta catttagttt tgccatagca tgacacaatg    120

gctcctagag atgtgataac ggagctgctt acatctgttt ttgaagtcat aattttgcaa    180

tcatatgtgt acctctgtat tctcccatta tgcctaggcc agcagcattg cctaatacta    240
```

cactggagaa gtgaggaaat tgagtcaaag acaataatga tgcttttggg ttgttcaata 300
tatggtagaa ccctgcttct ccacccaatt tttgggcata ttcatatgct ccgttggatg 360
gtgtatttgc tggatgacag aagttgatct ttgttgagtg tatcattcaa cttgactttg 420
ctaagagcca tttttgtatt tgccccatct ttcatcttat gtctctcctt aattttaaat 480
tactataatt ttcaggctcc atttgaacta tggagtgtgg tgcggccgc 529

<210> SEQ ID NO 61
<211> LENGTH: 564
<212> TYPE: DNA
<213> ORGANISM: artificial
<220> FEATURE:
<223> OTHER INFORMATION: Respiratory syncytial virus

<400> SEQUENCE: 61
taatacgact cactataggg agaaattaac cctcactaaa gggagaataa tcccacgatt 60
tttgttggat gcagtgcatt tagttttacc atagcatgac actatagctc caagagaagt 120
aattactgag ctgcttatgt ctgtttttga tgtcatatac tctcccatta tgcctagacc 180
tgctgcattg cctaggacca cacttgagaa gttaggaaat tgagttaatg acagcaatga 240
tgcttttgga ttgttcaata tatggtagaa tccagcttct cctcccaact tctgtgcata 300
ctcataattg ggagtgtcaa tattatctcc tgtactacgt tgaatagtgt atttgctgga 360
tgacagcagc tgatccttat ttaatgtatc atttaacttg actttgctaa gagccatctt 420
tgtatttgcc ccaatttatg ttattggctt tacttttatt tttaattact aaaacggatt 480
agctccttct taactattga gcattgttgt ttgaggaata gcttggtttg gttgggttgg 540 tttttttgt tggaatgcgg ccgc 564

<210> SEQ ID NO 62
<211> LENGTH: 454
<212> TYPE: DNA
<213> ORGANISM: artificial
<220> FEATURE:
<223> OTHER INFORMATION: Human parainfluenza virus 1

<400> SEQUENCE: 62
taatacgact cactataggg agaaattaac cctcactaaa gggagattga accagttgca 60
gtctgggttt cctggtcgcg acaggacttt atgaggcgcc caattaatgg tcatggggtt 120
gttgatatct aatgatccta tttgcaggtt ggagtgccaa cctgaacccc ttgttcctgc 180
agctattaca gaacatgatt tcctgttgtc gttgatgtca taggtatgag aaattaccgg 240
gtttaaatca ggatacatat ctgaatttaa ggatatgtaa cctaattgta aaacctgata 300
tgacttccct atatctgcac atccttgagt gattaagttt gatgaatacg catatattgc 360
atcaccaatt gataatgaag gtagtctaac acatcctgaa attgtggtgg atccagaaag 420
tagacttggt ccaggtaata atgagagcgg ccgc 454

<210> SEQ ID NO 63
<211> LENGTH: 427
<212> TYPE: DNA
<213> ORGANISM: artificial
<220> FEATURE:
<223> OTHER INFORMATION: Human parainfluenza virus 2

<400> SEQUENCE: 63
taatacgact cactataggg agaaattaac cctcactaaa gggagacatt aagcggccac 60

-continued

```
acatctgcgt acacccctgt gatgcaatta gcagggcaaa aacttgttgc attgcatggc    120

atgactccag gacgaggaac ttgataggac ggtacccatt gagcctcaat gatcggagct    180

gcaggattga ttgtggccca ctgccctgtt gtatttggaa gagatatgac tctttcaata    240

aaggtatcat tataataata gaaagcaagt ctcagttcag ctagatcagt cgtggcataa    300

tcttcttttt cagaccttgt agctacatag caatacaaga cacaacctcc tggtatagca    360

gtgactgaac agcttttgcg attgattcca tcacttaggt aaatggtttt catagtcctg    420

cggccgc                                                               427
```

<210> SEQ ID NO 64
<211> LENGTH: 344
<212> TYPE: DNA
<213> ORGANISM: artificial
<220> FEATURE:
<223> OTHER INFORMATION: Human parainfluenza virus 3

<400> SEQUENCE: 64

```
taatacgact cactataggg agaaattaac cctcactaaa gggagatgga catgaatgtc     60

cccatggaca ttcattgttt cctggtcttg atagcacatt atgccatgtc cattttatcc    120

ttatatcact gtagtcagta atgtcaatta ttcctaattg taacttgctg tgccaacttg    180

tagatcttgt atatataaag tatgagagat cctgggattt aagtcaggta ccaagtctga    240

gtttacagtt attatcccta tctgtaatac ttgatatgat tttcctatat cctgacaacc    300

tcgagtaatt agatttgagg tgtaagcata aatcaggcgg ccgc                      344
```

<210> SEQ ID NO 65
<211> LENGTH: 428
<212> TYPE: DNA
<213> ORGANISM: artificial
<220> FEATURE:
<223> OTHER INFORMATION: Human parainfluenza virus 4

<400> SEQUENCE: 65

```
taatacgact cactataggg agaaattaac cctcactaaa gggagactgt tattttaagt     60

gcatctatac gaacacctgc tcgtctctca tcggtttttt gtttggttcc agataatatg    120

ggtcttgcta atgagtcaag tgtaattgta ttgtcttgat caacaaattt tgagacgtct    180

ccgttaccag taacaattat aggaacttgt tctgattctt tgtttaaact cctgagactt    240

acttttgatg ggactccagg atccattatt ttcattgttg tgattaagcc ctcaattgtg    300

gcaagtgaac ctttgatttg ttgagtgtca ttctttgttt gctgaattgt attttgagta    360

agcataattt tgtcaacttt cccttcaatc ctgtctagtc tcacttctaa tgccttaatt    420

gcggccgc                                                              428
```

<210> SEQ ID NO 66
<211> LENGTH: 477
<212> TYPE: DNA
<213> ORGANISM: artificial
<220> FEATURE:
<223> OTHER INFORMATION: Human metapneumovirus

<400> SEQUENCE: 66

```
taatacgact cactataggg agaaattaac cctcactaaa gggagaggac catgctcact     60

gcacttgatt agtgctttca ctgtcttgca gggcatatga agagtcattg tcagcgcctg    120

ctgataagtc ctatctggcc aactccagta attgtggtta aacttgcact cacttcctct    180

gttgcatttg ccccgcactt catatttgca tggagccttg cgagacatta tgatttgtca    240
```

```
tcctagagct gtgctaatat attgtattcc tatttctgca gcatatttgt aatcagtatg    300

tttagcatat agaatttctc cacacaaaag tgttatttct tgttgcaatg atgagggtgt    360

cactgcagtt gttgtgccta catctctttt tattgtgtac tgagactctt ttaatatagc    420

atgcttgtat gatagatcac tcaggtgaat cccttgaaga gacattttcg cggccgc       477


<210> SEQ ID NO 67
<211> LENGTH: 461
<212> TYPE: DNA
<213> ORGANISM: artificial
<220> FEATURE:
<223> OTHER INFORMATION: Adenovirus types B, C and E

<400> SEQUENCE: 67

taatacgact cactataggg agaaattaac cctcactaaa gggagaatgg ccaccccatc     60

gatgctgccc caatgggcat acatgcacat cgccggacag gatgcttcgg agtacctgag    120

tccgggtctg gtgcagttcg cccgcgccac agacacctac ttcaatctgg gaaataagtt    180

tagaaatccc accgtagcgc cgacccacga tgtgaccacc gaccgtagcc agcggctcat    240

gttgcgcttc gtgacttggg acagaatatg ctctatgcca actcagctca tgctctggac    300

atgacctttg aggtggatcc catggatgag cccaccctgc tttatcttct cttcgaagtt    360

ttcgacgtgg tcagagtgca tcagccacac cgcggcatca tcgaggcagt ctacctgcgt    420

acaccgttct cggccggtaa cgctaccacg taagcggccg c                        461


<210> SEQ ID NO 68
<211> LENGTH: 413
<212> TYPE: DNA
<213> ORGANISM: artificial
<220> FEATURE:
<223> OTHER INFORMATION: Human Rhinovirus/Enterovirus

<400> SEQUENCE: 68

taatacgact cactataggg agaaattaac cctcactaaa gggagacaat agtagacctg     60

gcagatgagg ctagaaattc cccactggcg acagtgttct agcctgcgtg gctgcctgca    120

cacccctttt tgggctgtga agccatatat ttgacaaggt gtgaagagcc ccgtgtgctc    180

acttttgagt cctccggccc ctgaatgtgg ctaaccttaa ccctgcagcc attgcacaca    240

atccagtgtg tatctggtcg taatgagcaa ttgcgggatg ggaccaacta ctttgggtgt    300

ccgtgtttca tttttttcc ttttatattt tgcttatggt gacaatgtat atatagtata    360

tatatatttg tcatcatggg cgctcaggta tctagacaga atgttgcggc cgc           413


<210> SEQ ID NO 69
<211> LENGTH: 414
<212> TYPE: DNA
<213> ORGANISM: artificial
<220> FEATURE:
<223> OTHER INFORMATION: Bordetella pertussis

<400> SEQUENCE: 69

taatacgact cactataggg agaaattaac cctcactaaa gggagactag gtgtgaagat     60

tcaataggtt gtatgcatgg ttcatccgaa ccggatttga gaaactggaa atcgccaacc    120

ccccagttca ctcaaggagc ccggccggat gaacacccat aagcatgccc gattgacctt    180

cctacgtcga ctcgaaatgg tccagcaatt gatcgcccat caagtttgtg tgcctgaagc    240

ggcccgcttg ctcaccgaca atggctcggc ctttcgcagc cgcgccttcg ccgcgctgtg    300
```

ccatgagctg ggcatcaagc accgctttac ccgaccttac cgcccacaga ccaatggcaa 360
ggccgaacgc ttcatccagt cggccttgcg tgagtgggct tacgctgcgg ccgc 414

<210> SEQ ID NO 70
<211> LENGTH: 423
<212> TYPE: DNA
<213> ORGANISM: artificial
<220> FEATURE:
<223> OTHER INFORMATION: Chlamidophila pneumoniae

<400> SEQUENCE: 70
taatacgact cactataggg agaaattaac cctcactaaa gggagacttg cgctacttgg 60
tgcgacgcta ttagcttacg tgctggattt tacggagact atgttttcga ccgtatctta 120
aaagtagatg cacctaaaac attttctatg ggagccaacg ctggcgtagc aacagctact 180
ggaacaaagt ctgcgaccat caattatcat gaatggcaag taggagcctc tctatcttac 240
agactaaact ctttagtgcc atacattgga gtacaatggt ctcgagcaac ttttgatgct 300
gataacatcc gcattgctca gccaaaacta cctacagctg ttttaaactt aactgcatgg 360
aacccttctt tactaggaaa tgccacagca ttgtctacta ctgattcgtt ctcaggcggc 420
cgc 423

<210> SEQ ID NO 71
<211> LENGTH: 461
<212> TYPE: DNA
<213> ORGANISM: artificial
<220> FEATURE:
<223> OTHER INFORMATION: Mycoplasma pneumoniae

<400> SEQUENCE: 71
taatacgact cactataggg agaaattaac cctcactaaa gggagagcca gcaatttagc 60
tacacccgcc ctgacgaggt cgcgctgcgc cacaccaatg ccatcaaccc gcgcttaacc 120
ccgtgaacgt atcgtaacac gagcttttcc tccctccccc tcacgggtga aaatcccggg 180
gcgtgggcct tagtgcgcga caacagcgct aagggcatca ctgccggcag tggcagtcaa 240
caaaccacgt atgatcccac ccgaaccgaa gcggctttga ccgcatcaac cacctttgcg 300
ttacgccggt atgacctcgc cgggcgcgcc ttatacgacc tcgatttttc gaagttaaac 360
ccgcaaacgc ccacgcgcga ccaaaccggg cagatcacct ttaacccctt tggcggcttt 420
ggtttgagtg gggctgcacc ccaacagtga aacgcggccg c 461

<210> SEQ ID NO 72
<211> LENGTH: 354
<212> TYPE: DNA
<213> ORGANISM: artificial
<220> FEATURE:
<223> OTHER INFORMATION: Respiratory syncytial virus

<400> SEQUENCE: 72
taatacgact cactataggg agaaattaac cctcactaaa gggagaaata attctgttag 60
gacatacatt agtaaattgt tctactactg acattaagct aaggccaaag cttatacagt 120
tttggaatac tatatcaata tcttcatcac catacttttc tgttaatatg cgattaatag 180
ggctagtatc aaagtgataa tttgtagttc tataagctgg tattgatgca gggaattcac 240
atggtctact actgactgta aggcgatgca aatagttaac acttaaatat tgtggaaata 300
attttttggc tttctcatat gttaacccaa gaattcctat gctaaggcgg ccgc 354

<210> SEQ ID NO 73
<211> LENGTH: 354
<212> TYPE: DNA
<213> ORGANISM: artificial
<220> FEATURE:
<223> OTHER INFORMATION: Respiratory syncytial virus

<400> SEQUENCE: 73
taatacgact cactataggg agaaattaac cctcactaaa gggagaataa ttctattagg 60
acatatgttt gtgaattgtt ccacaaccga catcaggcta agaccaaaac ttatgcaatt 120
ttgaaacaca atgtcgatat cttcatctcc atacttttct gttaatacat gattgatagg 180
actagtatcg aaatgataat ttgttgttct ataagctggt attgatgcag ggaattcaca 240
tggtctacta ctgactgtta aacggtgtaa ataattgaca cttagatatt gtggaaacaa 300
ctttttggct ttttcatatg acagtccaag tgttccagta ctcagtgcgg ccgc 354

<210> SEQ ID NO 74
<211> LENGTH: 27
<212> TYPE: DNA
<213> ORGANISM: artificial
<220> FEATURE:
<223> OTHER INFORMATION: Am-InfA2 F

<400> SEQUENCE: 74
cgaggtcgaa acgtaygttc tytctat 27

<210> SEQ ID NO 75
<211> LENGTH: 25
<212> TYPE: DNA
<213> ORGANISM: artificial
<220> FEATURE:
<223> OTHER INFORMATION: InfA2 R

<400> SEQUENCE: 75
gccattccat gagagcctcr agatc 25

<210> SEQ ID NO 76
<211> LENGTH: 42
<212> TYPE: DNA
<213> ORGANISM: artificial
<220> FEATURE:
<223> OTHER INFORMATION: Acry InfA2 Pr

<400> SEQUENCE: 76
aattgaattc ggatccagtc tctgcgcgat ctcggctttg ag 42

<210> SEQ ID NO 77
<211> LENGTH: 26
<212> TYPE: DNA
<213> ORGANISM: artificial
<220> FEATURE:
<223> OTHER INFORMATION: Am-InfB-2 F

<400> SEQUENCE: 77
tacggtggat taaacaaaag caagcc 26

<210> SEQ ID NO 78
<211> LENGTH: 28
<212> TYPE: DNA
<213> ORGANISM: artificial
<220> FEATURE:
<223> OTHER INFORMATION: InfB-2 R

<400> SEQUENCE: 78

-continued caggaggtct atatttggtt ccattggc 28

<210> SEQ ID NO 79
<211> LENGTH: 38
<212> TYPE: DNA
<213> ORGANISM: artificial
<220> FEATURE:
<223> OTHER INFORMATION: Acry AS InfB-2 P

<400> SEQUENCE: 79
gaattcggat ccggtgtttt cacccatatt gggcaatt 38

<210> SEQ ID NO 80
<211> LENGTH: 25
<212> TYPE: DNA
<213> ORGANISM: artificial
<220> FEATURE:
<223> OTHER INFORMATION: H1N1 R

<400> SEQUENCE: 80
gctttttgct ccagcatgag gacat 25

<210> SEQ ID NO 81
<211> LENGTH: 26
<212> TYPE: DNA
<213> ORGANISM: artificial
<220> FEATURE:
<223> OTHER INFORMATION: N1N1 F

<400> SEQUENCE: 81
cccaagacaa gttcatggcc caatca 26

<210> SEQ ID NO 82
<211> LENGTH: 41
<212> TYPE: DNA
<213> ORGANISM: artificial
<220> FEATURE:
<223> OTHER INFORMATION: Acry H1N1 P

<400> SEQUENCE: 82
aattgaattc ggatcccgaa caaaggtgta acggcagcat g 41

<210> SEQ ID NO 83
<211> LENGTH: 27
<212> TYPE: DNA
<213> ORGANISM: artificial
<220> FEATURE:
<223> OTHER INFORMATION: Am-H5N1 F

<400> SEQUENCE: 83
gctctgcgat ctagatggag tgaagcc 27

<210> SEQ ID NO 84
<211> LENGTH: 28
<212> TYPE: DNA
<213> ORGANISM: artificial
<220> FEATURE:
<223> OTHER INFORMATION: H5N1 R

<400> SEQUENCE: 84
ycttctccac tatgtaagac cattccgg 28

<210> SEQ ID NO 85
<211> LENGTH: 41
<212> TYPE: DNA
<213> ORGANISM: artificial

```
<220> FEATURE:
<223> OTHER INFORMATION: Acry AS-HFN1 P

<400> SEQUENCE: 85

aattgaattc ggatccccga ggagccatcc agctacacta c                          41


<210> SEQ ID NO 86
<211> LENGTH: 27
<212> TYPE: DNA
<213> ORGANISM: artificial
<220> FEATURE:
<223> OTHER INFORMATION: Am-RSV-3 F

<400> SEQUENCE: 86

acagtcagta gtagaccatg tgaattc                                          27


<210> SEQ ID NO 87
<211> LENGTH: 32
<212> TYPE: DNA
<213> ORGANISM: artificial
<220> FEATURE:
<223> OTHER INFORMATION: RSV-3 R

<400> SEQUENCE: 87

rtcratatct tcatcaccat acttttctgt ta                                    32


<210> SEQ ID NO 88
<211> LENGTH: 42
<212> TYPE: DNA
<213> ORGANISM: artificial
<220> FEATURE:
<223> OTHER INFORMATION: Acry AS-RSV-3 P

<400> SEQUENCE: 88

aattgaattc ggatccgttc tataagctgg tattgatgca gg                         42


<210> SEQ ID NO 89
<211> LENGTH: 27
<212> TYPE: DNA
<213> ORGANISM: artificial
<220> FEATURE:
<223> OTHER INFORMATION: Am GB HPIV1 F

<400> SEQUENCE: 89

tggtgatgca atatatgcgt attcatc                                          27


<210> SEQ ID NO 90
<211> LENGTH: 27
<212> TYPE: DNA
<213> ORGANISM: artificial
<220> FEATURE:
<223> OTHER INFORMATION: GB HPIV1 R

<400> SEQUENCE: 90

ccgggtttaa atcaggatac atatctg                                          27


<210> SEQ ID NO 91
<211> LENGTH: 39
<212> TYPE: DNA
<213> ORGANISM: artificial
<220> FEATURE:
<223> OTHER INFORMATION: Acry GB HPIV1 P

<400> SEQUENCE: 91

gaattcggat cccctatatc tgcacatcct tgagtgatt                             39
```

<210> SEQ ID NO 92
<211> LENGTH: 25
<212> TYPE: DNA
<213> ORGANISM: artificial
<220> FEATURE:
<223> OTHER INFORMATION: Am-Para2 F

<400> SEQUENCE: 92
cycgtcctgg agtcatgcca tgcaa 25

<210> SEQ ID NO 93
<211> LENGTH: 24
<212> TYPE: DNA
<213> ORGANISM: artificial
<220> FEATURE:
<223> OTHER INFORMATION: Para2 R

<400> SEQUENCE: 93
crttaagcgg ccacacatct gcgt 24

<210> SEQ ID NO 94
<211> LENGTH: 38
<212> TYPE: DNA
<213> ORGANISM: artificial
<220> FEATURE:
<223> OTHER INFORMATION: Acry AS-Para2 P

<400> SEQUENCE: 94
gaattcggat ccacccctgt gatgcaatta gcagggca 38

<210> SEQ ID NO 95
<211> LENGTH: 29
<212> TYPE: DNA
<213> ORGANISM: artificial
<220> FEATURE:
<223> OTHER INFORMATION: Am-Para3 F

<400> SEQUENCE: 95
caagttggca yagcaagtta caattagga 29

<210> SEQ ID NO 96
<211> LENGTH: 29
<212> TYPE: DNA
<213> ORGANISM: artificial
<220> FEATURE:
<223> OTHER INFORMATION: Para3 R

<400> SEQUENCE: 96
gtccccatgg acattcattg tttcctggt 29

<210> SEQ ID NO 97
<211> LENGTH: 40
<212> TYPE: DNA
<213> ORGANISM: artificial
<220> FEATURE:
<223> OTHER INFORMATION: Acry AS-Para3 P

<400> SEQUENCE: 97
gaattcggat ccagcacatt atgccatgtc cattttatcc 40

<210> SEQ ID NO 98
<211> LENGTH: 29
<212> TYPE: DNA
<213> ORGANISM: artificial
<220> FEATURE:
<223> OTHER INFORMATION: am-Para4 F

<400> SEQUENCE: 98
gttgatcaag acaatacaat tacacttga 29

<210> SEQ ID NO 99
<211> LENGTH: 27
<212> TYPE: DNA
<213> ORGANISM: artificial
<220> FEATURE:
<223> OTHER INFORMATION: Para4 R

<400> SEQUENCE: 99
taagtgcatc tatacgaacr cctgctc 27

<210> SEQ ID NO 100
<211> LENGTH: 38
<212> TYPE: DNA
<213> ORGANISM: artificial
<220> FEATURE:
<223> OTHER INFORMATION: Acry GB HPIV-4 Pr1

<400> SEQUENCE: 100
gaattcggat ccggttccag acaaaatggg tcttgcta 38

<210> SEQ ID NO 101
<211> LENGTH: 38
<212> TYPE: DNA
<213> ORGANISM: artificial
<220> FEATURE:
<223> OTHER INFORMATION: Acry GB HPIV-4 Pr2

<400> SEQUENCE: 101
gaattcggat ccggttccag ataatatggg tcttgcta 38

<210> SEQ ID NO 102
<211> LENGTH: 28
<212> TYPE: DNA
<213> ORGANISM: artificial
<220> FEATURE:
<223> OTHER INFORMATION: Am-hMPV F

<400> SEQUENCE: 102
gacaaatcat matgtctcgy aargctcc 28

<210> SEQ ID NO 103
<211> LENGTH: 26
<212> TYPE: DNA
<213> ORGANISM: artificial
<220> FEATURE:
<223> OTHER INFORMATION: hMPV R

<400> SEQUENCE: 103
ctatcwggcc aactccagta attgtg 26

<210> SEQ ID NO 104
<211> LENGTH: 35
<212> TYPE: DNA
<213> ORGANISM: artificial
<220> FEATURE:
<223> OTHER INFORMATION: Acry AS-hMPV P

<400> SEQUENCE: 104
gaattcggat ccttgccccg yacttcatat ttgca 35

<210> SEQ ID NO 105

-continued

<211> LENGTH: 26
<212> TYPE: DNA
<213> ORGANISM: artificial
<220> FEATURE:
<223> OTHER INFORMATION: AdV F

<400> SEQUENCE: 105
tgccscartg gkcdtacatg cacatc 26

<210> SEQ ID NO 106
<211> LENGTH: 20
<212> TYPE: DNA
<213> ORGANISM: artificial
<220> FEATURE:
<223> OTHER INFORMATION: AdV R

<400> SEQUENCE: 106
gcrcgggcra actgcaccag 20

<210> SEQ ID NO 107
<211> LENGTH: 40
<212> TYPE: DNA
<213> ORGANISM: artificial
<220> FEATURE:
<223> OTHER INFORMATION: Acry AdV B/E P

<400> SEQUENCE: 107
aattgaattc ggatccgctt cggagtacct gagtccgggt 40

<210> SEQ ID NO 108
<211> LENGTH: 40
<212> TYPE: DNA
<213> ORGANISM: artificial
<220> FEATURE:
<223> OTHER INFORMATION: Acry AdV C P

<400> SEQUENCE: 108
aattgaattc ggatcctcgg gccaggacgc ctcggagtac 40

<210> SEQ ID NO 109
<211> LENGTH: 23
<212> TYPE: DNA
<213> ORGANISM: artificial
<220> FEATURE:
<223> OTHER INFORMATION: truncRhi R

<400> SEQUENCE: 109
gaaacacgga cacccaaagt agt 23

<210> SEQ ID NO 110
<211> LENGTH: 28
<212> TYPE: DNA
<213> ORGANISM: artificial
<220> FEATURE:
<223> OTHER INFORMATION: T7truncRhi F

<400> SEQUENCE: 110
actcactata ggagcctgcg tggckgcc 28

<210> SEQ ID NO 111
<211> LENGTH: 37
<212> TYPE: DNA
<213> ORGANISM: artificial
<220> FEATURE:
<223> OTHER INFORMATION: Acry Rhi P

<400> SEQUENCE: 111
gaattcggat cctcctccgg cccctgaatg yggctaa 37

<210> SEQ ID NO 112
<211> LENGTH: 25
<212> TYPE: DNA
<213> ORGANISM: artificial
<220> FEATURE:
<223> OTHER INFORMATION: Bper F

<400> SEQUENCE: 112
ccggccggat gaacacccat aagca 25

<210> SEQ ID NO 113
<211> LENGTH: 25
<212> TYPE: DNA
<213> ORGANISM: artificial
<220> FEATURE:
<223> OTHER INFORMATION: Bper R

<400> SEQUENCE: 113
gggccgcttc aggcacacaa acttg 25

<210> SEQ ID NO 114
<211> LENGTH: 37
<212> TYPE: DNA
<213> ORGANISM: artificial
<220> FEATURE:
<223> OTHER INFORMATION: Acry Bper P

<400> SEQUENCE: 114
gaattcggat cctgcccgat tgaccttcct acgtcga 37

<210> SEQ ID NO 115
<211> LENGTH: 25
<212> TYPE: DNA
<213> ORGANISM: artificial
<220> FEATURE:
<223> OTHER INFORMATION: Cpn F

<400> SEQUENCE: 115
catgaatggc aagtaggagc ctctc 25

<210> SEQ ID NO 116
<211> LENGTH: 25
<212> TYPE: DNA
<213> ORGANISM: artificial
<220> FEATURE:
<223> OTHER INFORMATION: Cpn R

<400> SEQUENCE: 116
agttttggct gagcaatgcg gatgt 25

<210> SEQ ID NO 117
<211> LENGTH: 37
<212> TYPE: DNA
<213> ORGANISM: artificial
<220> FEATURE:
<223> OTHER INFORMATION: Acry Cpn P

<400> SEQUENCE: 117
gaattcggat cctggtctcg agcaactttt gatgctg 37

<210> SEQ ID NO 118
<211> LENGTH: 25
<212> TYPE: DNA

<213> ORGANISM: artificial
<220> FEATURE:
<223> OTHER INFORMATION: Mpneu F

<400> SEQUENCE: 118
gaaccgaagc ggctttgacc gcatc 25

<210> SEQ ID NO 119
<211> LENGTH: 25
<212> TYPE: DNA
<213> ORGANISM: artificial
<220> FEATURE:
<223> OTHER INFORMATION: Mpneu R

<400> SEQUENCE: 119
gcgtgggcgt ttgcgggttt aactt 25

<210> SEQ ID NO 120
<211> LENGTH: 37
<212> TYPE: DNA
<213> ORGANISM: artificial
<220> FEATURE:
<223> OTHER INFORMATION: Acry Mpneu P

<400> SEQUENCE: 120
gaattcggat ccgggcgcgc cttatacgac ctcgatt 37

<210> SEQ ID NO 121
<211> LENGTH: 25
<212> TYPE: DNA
<213> ORGANISM: artificial
<220> FEATURE:
<223> OTHER INFORMATION: MS2-2 R

<400> SEQUENCE: 121
cttttgcagg acttcggtcg acgcc 25

<210> SEQ ID NO 122
<211> LENGTH: 25
<212> TYPE: DNA
<213> ORGANISM: artificial
<220> FEATURE:
<223> OTHER INFORMATION: MS2-2 F

<400> SEQUENCE: 122
gcacgctcct gctacagcct cttcc 25

<210> SEQ ID NO 123
<211> LENGTH: 41
<212> TYPE: DNA
<213> ORGANISM: artificial
<220> FEATURE:
<223> OTHER INFORMATION: Acry MS2-2 P

<400> SEQUENCE: 123
aattgaattc ggatccgaag tgccgcagaa cgttgcgaac c 41

<210> SEQ ID NO 124
<211> LENGTH: 25
<212> TYPE: DNA
<213> ORGANISM: artificial
<220> FEATURE:
<223> OTHER INFORMATION: MYL3 F

<400> SEQUENCE: 124
gcacccagac aatacacaca ggtgt 25

<210> SEQ ID NO 125
<211> LENGTH: 22
<212> TYPE: DNA
<213> ORGANISM: artificial
<220> FEATURE:
<223> OTHER INFORMATION: MYL3 R

<400> SEQUENCE: 125
ggcggaagtc agcatgtgtc tg 22

<210> SEQ ID NO 126
<211> LENGTH: 51
<212> TYPE: DNA
<213> ORGANISM: artificial
<220> FEATURE:
<223> OTHER INFORMATION: Pap Type ProbeMLC_Int Oligo

<400> SEQUENCE: 126
aaagggagga cagctatgga ccaaacacag acacagagag acccacagac a 51

<210> SEQ ID NO 127
<211> LENGTH: 26
<212> TYPE: DNA
<213> ORGANISM: artificial
<220> FEATURE:
<223> OTHER INFORMATION: Forward primer Am-InfA

<400> SEQUENCE: 127
trggrtttgt gttcacgctc accgtg 26

<210> SEQ ID NO 128
<211> LENGTH: 26
<212> TYPE: DNA
<213> ORGANISM: artificial
<220> FEATURE:
<223> OTHER INFORMATION: Reverse primer P-InfA

<400> SEQUENCE: 128
gggcattttg gacaaagcgt ctacgc 26

<210> SEQ ID NO 129
<211> LENGTH: 34
<212> TYPE: DNA
<213> ORGANISM: artificial
<220> FEATURE:
<223> OTHER INFORMATION: AS InfA

<400> SEQUENCE: 129
gaattcggat cctgcagtcc tcgctcactg ggca 34

<210> SEQ ID NO 130
<211> LENGTH: 27
<212> TYPE: DNA
<213> ORGANISM: artificial
<220> FEATURE:
<223> OTHER INFORMATION: Forward primer alt Am-InfA

<400> SEQUENCE: 130
gacaagacca atcctgtcac ctctgac 27

<210> SEQ ID NO 131
<211> LENGTH: 26
<212> TYPE: DNA
<213> ORGANISM: artificial
<220> FEATURE:

<223> OTHER INFORMATION: Reverse primer P-InfA

<400> SEQUENCE: 131
gggcattttg gacaaagcgt ctacgc 26

<210> SEQ ID NO 132
<211> LENGTH: 34
<212> TYPE: DNA
<213> ORGANISM: artificial
<220> FEATURE:
<223> OTHER INFORMATION: AS InfA

<400> SEQUENCE: 132
gaattcggat cctgcagtcc tcgctcactg ggca 34

<210> SEQ ID NO 133
<211> LENGTH: 27
<212> TYPE: DNA
<213> ORGANISM: artificial
<220> FEATURE:
<223> OTHER INFORMATION: Forward primer InfB

<400> SEQUENCE: 133
gcaccaggag gaccctacar amttgga 27

<210> SEQ ID NO 134
<211> LENGTH: 26
<212> TYPE: DNA
<213> ORGANISM: artificial
<220> FEATURE:
<223> OTHER INFORMATION: Reverse primer InfB

<400> SEQUENCE: 134
ttgggacrgc ccaagccatt gttgcg 26

<210> SEQ ID NO 135
<211> LENGTH: 28
<212> TYPE: DNA
<213> ORGANISM: artificial
<220> FEATURE:
<223> OTHER INFORMATION: InfB

<400> SEQUENCE: 135
acctcaggrt cttgccctaa cgytacca 28

<210> SEQ ID NO 136
<211> LENGTH: 26
<212> TYPE: DNA
<213> ORGANISM: artificial
<220> FEATURE:
<223> OTHER INFORMATION: Forward primer RSV

<400> SEQUENCE: 136
ttgggwggag aagcwggwtt ctacca 26

<210> SEQ ID NO 137
<211> LENGTH: 26
<212> TYPE: DNA
<213> ORGANISM: artificial
<220> FEATURE:
<223> OTHER INFORMATION: Reverse primer RSV

<400> SEQUENCE: 137
attatgccta grccwgcwgc attgcc 26

-continued

```
<210> SEQ ID NO 138
<211> LENGTH: 29
<212> TYPE: DNA
<213> ORGANISM: artificial
<220> FEATURE:
<223> OTHER INFORMATION: RSV

<400> SEQUENCE: 138

aryartgatg cttttggrtt gttcaatat                                   29


<210> SEQ ID NO 139
<211> LENGTH: 27
<212> TYPE: DNA
<213> ORGANISM: artificial
<220> FEATURE:
<223> OTHER INFORMATION: Forward primer Am-Para1

<400> SEQUENCE: 139

tggcactcca acctgcaaat aggatca                                     27


<210> SEQ ID NO 140
<211> LENGTH: 27
<212> TYPE: DNA
<213> ORGANISM: artificial
<220> FEATURE:
<223> OTHER INFORMATION: Reverse primer P-Para1

<400> SEQUENCE: 140

ccagttgcag tcttggtttc ctggtcg                                     27


<210> SEQ ID NO 141
<211> LENGTH: 34
<212> TYPE: DNA
<213> ORGANISM: artificial
<220> FEATURE:
<223> OTHER INFORMATION: AS-Para1

<400> SEQUENCE: 141

gaattcggat ccacaggact tyatgaggcg ccca                             34
```